US010781166B2

(12) United States Patent
Das et al.

(10) Patent No.: US 10,781,166 B2
(45) Date of Patent: Sep. 22, 2020

(54) BIOCOMPOSITIONS FOR 3D PRINTING

(71) Applicant: 3D-Biomaterials, LLC, Peapack, NJ (US)

(72) Inventors: Sajal Das, Bedmister, NJ (US); Patrick Shipman, Stirling, NJ (US); Scott Shuler, Morristown, NJ (US)

(73) Assignee: 3D-Biomaterials, LLC, Peapack, NJ (US)

( * ) Notice: Subject to any disclaimer, the term of this patent is extended or adjusted under 35 U.S.C. 154(b) by 0 days.

(21) Appl. No.: 16/290,397

(22) Filed: Mar. 1, 2019

(65) Prior Publication Data

US 2019/0194123 A1  Jun. 27, 2019

Related U.S. Application Data

(62) Division of application No. 16/110,639, filed on Aug. 23, 2018, now Pat. No. 10,590,066.

(60) Provisional application No. 62/566,120, filed on Sep. 29, 2017.

(51) Int. Cl.
| | |
|---|---|
| *C08G 63/193* | (2006.01) |
| *C07C 233/46* | (2006.01) |
| *C07C 235/52* | (2006.01) |
| *C08F 220/36* | (2006.01) |
| *C07C 235/34* | (2006.01) |
| *A61L 27/18* | (2006.01) |
| *C07C 271/22* | (2006.01) |
| *C07C 237/22* | (2006.01) |
| *C08F 220/60* | (2006.01) |
| *C07C 237/20* | (2006.01) |
| *C08L 33/10* | (2006.01) |
| *C08L 67/06* | (2006.01) |
| *C08L 77/12* | (2006.01) |

(51) Int. Cl.
| | |
|---|---|
| *A61K 9/00* | (2006.01) |
| *B33Y 70/00* | (2020.01) |

(52) U.S. Cl.
CPC ............ *C07C 233/46* (2013.01); *A61L 27/18* (2013.01); *C07C 235/34* (2013.01); *C07C 235/52* (2013.01); *C07C 237/20* (2013.01); *C07C 237/22* (2013.01); *C07C 271/22* (2013.01); *C08F 220/36* (2013.01); *C08F 220/60* (2013.01); *C08G 63/193* (2013.01); *C08L 33/10* (2013.01); *C08L 67/06* (2013.01); *C08L 77/12* (2013.01); *A61K 9/0024* (2013.01); *B33Y 70/00* (2014.12); *C08F 220/365* (2020.02); *C08F 220/603* (2020.02); *C08L 2201/06* (2013.01); *C08L 2203/02* (2013.01)

(58) Field of Classification Search
CPC ..... C07C 233/46; C08G 63/193; C08L 33/10; C08L 67/06; C08L 77/12; B33Y 70/00
See application file for complete search history.

(56) References Cited

U.S. PATENT DOCUMENTS

2011/0294760 A1* 12/2011 Bahulekar ............ A61K 9/1647
514/154

FOREIGN PATENT DOCUMENTS

WO   2017064145 A1   4/2017

OTHER PUBLICATIONS

International Search Report and Written Opinion, dated Feb. 15, 2019.

* cited by examiner

*Primary Examiner* — Ling Siu Choi
*Assistant Examiner* — David L Miller
(74) *Attorney, Agent, or Firm* — Charney IP Law LLC; Thomas M. Finetti

(57) ABSTRACT

The present disclosure is directed to resins and to polymers, copolymers, and blends formed therefrom.

20 Claims, 4 Drawing Sheets

BIOCOMPOSITIONS FOR 3D PRINTING

CROSS REFERENCE TO RELATED APPLICATIONS

The present application claims the benefit of the filing date of U.S. Provisional Patent Application 62/566,120 filed Sep. 29, 2017, the disclosure of which is hereby incorporated by reference herein in its entirety.

BACKGROUND OF THE DISCLOSURE

Three-dimensional printing is a type of computer-based printing that creates a three-dimensional object by progressively depositing material onto a substrate (i.e., a printable surface). The concept of three-dimensional printing has been around for over thirty years, but availability of the technology has been limited commercially until the last several years. In many current three-dimensional printing systems, an ink-jet-type printer is used to serially print a material such as a thermoplastic, a metal alloy, or a plaster as layers of particles or three-dimensional dots on the substrate. Computer-control of the location and number of such layers can direct so-called "additive manufacturing" of a designed article.

Additive manufacturing (AM) process defines a process wherein digital 3-D design data is utilized to deposit materials one layer at a time to build up a component. The term "3-D printing" is frequently used as a synonym for AM. 3-D printing techniques are considered AM processes because they involve the application of successive layers of materials. Current commercial 3-D printers can selectively extrude thermoplastic, cure photosensitive resins, and sinter metallic, ceramic or polymer powders into designs that can be drawn with a computer-aided design program. The material selection combined with hardware (printer) and software is key for rapid prototyping and cost-effective manufacturing. Thermoset materials used in 3-D printing often require curing and post curing. Extrusion printer technology forces thermoplastics through a heated zone to build 3-D structures. 3-D printing structures are frequently formed using Stereolithographic technology (also known as optical fabrication, photo-solidification, solid free-form fabrication, solid imaging and Resin printing), producing models, prototypes, patterns, and production parts. Stereolithography is an additive manufacturing process that uses photosensitive thermoset resins or photo-reactive resins that are cured with a UV laser or similar power source. However, this process has been found to be too slow and expensive for 3-D printing and is not compatible with compositions that contain light-scattering particles fillers, pigment, waxes etc.

Currently, various materials are being used in three-dimensional (3D) printers. Various materials may include, for example, plastic (for example, an acrylonitrile-butadiene-styrene (ABS) resin or acrylic materials), metal (for examples, stainless steel or silver), rubber, ceramic materials, or biomaterials, or food (for examples, chocolate or powder). Also, even the same material may have different properties, for example, a thermal resistance that is a degree to which materials resist heat, a durability that is a degree to which materials endure, or a low-temperature resistance that is a degree to which materials resist a low temperature.

BRIEF SUMMARY OF THE DISCLOSURE

In one aspect of the present disclosure are compounds having the structure of Formula (IA):

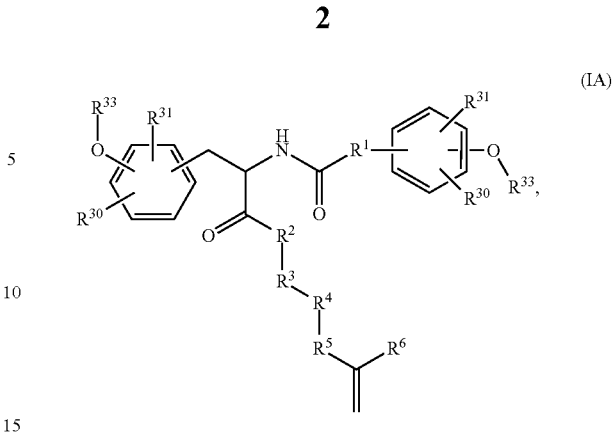

(IA)

wherein
$R^1$ is a saturated or unsaturated, straight chain or branched alkyl group having between 0 and 12 carbon atoms;
$R^2$ is —O—, —NR$^s$— where R$^s$ is H or a $C_1$-$C_4$ alkyl group, or —S—;
$R^3$ is a straight chain or branched alkyl group having up to 10 carbon atoms, a straight chain or branched alkylaryl group having up to 20 carbon atoms, or a siloxane group;
$R^4$ is —O—, —NR$^s$— where R$^s$ is H or a C1-$C_4$ alkyl group, —S—, —CH$_2$—;
$R^5$ is —C(O)—, —CH$_2$—, —C(H)(Ph)- where Ph may include one or more substituents selected from —OH, a halogen, $C_1$-$C_4$ alkyl, or —NR$^s$— where R$^s$ is H or a $C_1$-$C_4$ alkyl group;
$R^6$ is H or a straight chain or branched alkyl group having up to 18 carbons atoms;
each of $R^{30}$ and $R^{31}$ are independently selected from I or H; and
each $R^{33}$ is independently H, —CN, 4-hydroxybenzene, 3-iodo-4-hydroxybenzene, or 3,5-diiodo-4-hydroxybenzene.

In another aspect of the present disclosure is a reaction product of a compound of Formula (IA) and a diacid, a diisocyanate, or a cyanate ester. In some embodiments, the reaction product may be polymerized and/or crosslinked.

In another aspect of the present disclosure is a medical device comprising a material derived from a reaction product of a compound of Formula (IA) and a diacid, a diisocyanate, or a cyanate ester.

In another aspect of the present disclosure is a compound have the structure of Formula (IC):

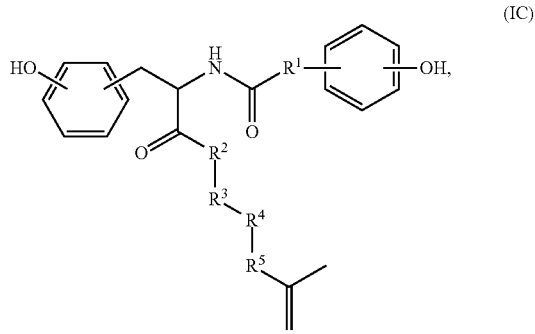

(IC)

wherein
$R^1$ is —CH=CH— or (—CH$_2$-)$_n$;
$R^2$ is —O—, —NR$^s$—, where R$^s$ is H or a $C_1$-$C_4$ alkyl group, or —S—;

$R^3$ is a straight chain or branched alkyl group having up to 10 carbon atoms, a straight chain or branched alkylaryl group having up to 20 carbon atoms, or a siloxane group;

$R^4$ is —O—, —$NR^s$—, where $R^s$ is H or a $C_1$-$C_4$ alkyl group, —S—, —$CH_2$—;

$R^5$ is —C(O)—, —$CH_2$— or —C(H)(Ph)-;

n is 0 or an integer ranging from 1 to 8.

In some embodiments, $R^1$ is —$CH_2CH_2CH_2$—. In some embodiments, $R^1$ is —$CH_2CH_2$—. In some embodiments, $R^1$ is —$CH_2$—.

In some embodiments, at least two of $R^2$, $R^4$, and $R^5$ are O. In some embodiments, at least one of $R^2$ or $R^4$ is —O—; $R^3$ is a straight chain or branched $C_1$-$C_6$ alkyl group; and $R^1$ is a $C_1$-$C_6$ alkyl group. In some embodiments, both of $R^2$ and $R^4$ are —O—; $R^3$ is a straight chain or branched $C_1$-$C_6$ alkyl group; and $R^1$ is a $C_1$-$C_6$ alkyl group. In some embodiments, both of $R^2$ and $R^4$ are —O—; $R^3$ is a straight chain or branched $C_1$-$C_6$ alkyl group; $R^1$ is a $C_1$-$C_6$ alkyl group; and $R^5$ is C=O. In some embodiments, both of $R^2$ and $R^4$ are —O—; $R^3$ is a straight chain or branched $C_1$-$C_6$ alkyl group; $R^1$ is a $C_1$-$C_6$ alkyl group; and $R^5$ is —$CH_2$—. In some embodiments, $R^5$ is C=O or —$CH_2$—.

In another aspect of the present disclosure is a reaction product of a compound of Formula (IC) and a diacid, a diisocyanate, or a cyanate ester. In some embodiments, the reaction product may be polymerized and/or crosslinked.

In another aspect of the present disclosure is a medical device comprising a material derived from a reaction product of a compound of Formula (IC) and a diacid, a diisocyanate, or a cyanate ester.

In another aspect of the present disclosure are compound having the structure of Formula (IIA):

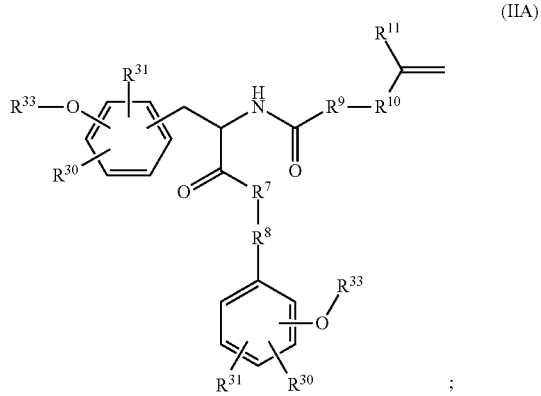

(IIA)

wherein $R^7$ is —O—, —$NR^s$— where $R^s$ is H or a $C_1$-$C_4$ alkyl group, —S—, —$CH_2$—;

$R^s$ is a saturated or unsaturated, substituted or unsubstituted, straight chain or branched alkyl group having between 1 and 20 carbon atoms;

$R^9$ is a bond, —O—, —$(CH_2)_m$—;

$R^{10}$ is a bond; a straight chain or branched alkyl group having up to 10 carbon atoms; a straight chain or branched alkylaryl group having up to 20 carbon atoms; —($CR^aR^b$—$CR^aR^bO)_o$—, —($CR^aR^b$—$CR^aR^b$—O$)_o$—C(O)— wherein $R^a$ and $R^b$ are independently H or a $C_1$-$C_4$ alkyl group; or a siloxane group;

$R^{11}$ is H or a straight chain or branched alkyl group having up to 18 carbons;

each of $R^{30}$ and $R^{31}$ are independently selected from I or H;

each $R^{33}$ is independently H, —CN, 4-hydroxybenzene, 3-iodo-4-hydroxybenzene, or 3,5-diiodo-4-hydroxybenzene;

m is 0 or an integer ranging from 1 to 8; and o is an integer ranging from 1 to 500.

In another aspect of the present disclosure is a reaction product of a compound of Formula (IIA) and a diacid, a diisocyanate, or a cyanate ester. In some embodiments, the reaction product may be polymerized and/or crosslinked.

In another aspect of the present disclosure is a medical device comprising a material derived from a reaction product of a compound of Formula (IIA) and a diacid, a diisocyanate, or a cyanate ester.

In another aspect of the present disclosure is compound having the structure of Formula (IIC):

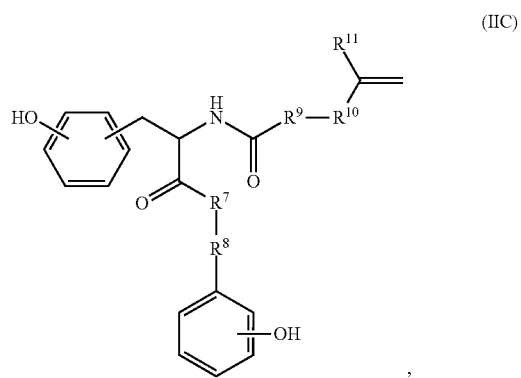

(IIC)

wherein $R^1$ is —O—, —$NR^s$—, where $R^s$ is H or a $C_1$-$C_4$ alkyl group, —S—, —$CH_2$—;

$R^8$ is -CH=CH— or —$(CH_2)_n$—;

$R^9$ is a bond, —O— or (—$CH_2$-$)_m$;

$R^{10}$ is a bond, —($CH_2CH_2O)_o$—, —($CH_2CH_2O)_oC(O)$—, a straight chain or branched alkyl group having up to 10 carbon atoms, a straight chain or branched alkylaryl group having up to 20 carbon atoms, or a siloxane group;

$R^{11}$ is H or a straight chain or branched alkyl group having up to 18 carbons;

m and n are independently 0 or an integer ranging from 1 to 8; and each o is independently 0 or an integer ranging from 1 to 500.

In some embodiments, $R^7$ is —NH—, and $R^8$ is —$(CH_2)_n$—. In some embodiments, $R^7$ is —NH—, and $R^8$ is —$(CH_2)_n$—, where n is an integer ranging from 1 to 4. In some embodiments, $R^7$ is —NH—, and $R^8$ is —$(CH_2)_n$—, where n is an integer ranging from 1 to 2. In some embodiments, $R^{11}$ is a $C_1$-$C_6$ alkyl group. In some embodiments, $R^{11}$ is a $C_1$-$C_4$ alkyl group. In some embodiments, $R^{11}$ is a $C_1$-$C_2$ alkyl group. In some embodiments, both $R^9$ and $R^{10}$ are bonds.

In another aspect of the present disclosure is a reaction product of a compound of Formula (IIC) and a diacid, a diisocyanate, or a cyanate ester. In some embodiments, the reaction product may be polymerized and/or crosslinked.

In another aspect of the present disclosure is a medical device comprising a material derived from a reaction product of a compound of Formula (IIC) and a diacid, a diisocyanate, or a cyanate ester.

In another aspect of the present disclosure are compounds having the structure of Formula (VIIA):

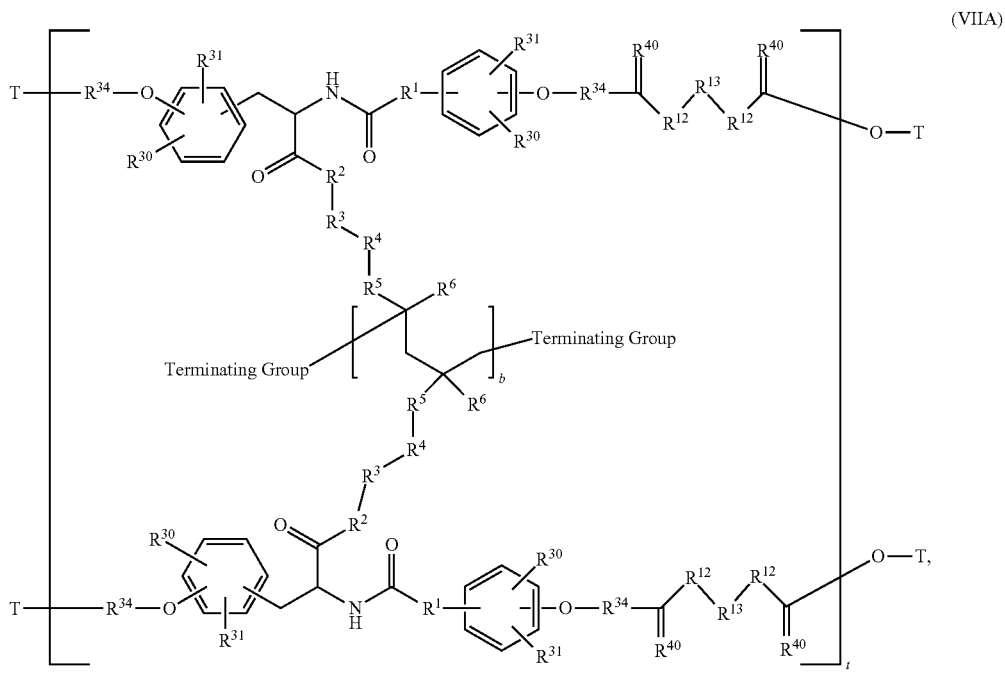

wherein
$R^1$ is —CH=CH— or (—CH$_2$—);
$R^2$ is —O—, —NR$^s$—, where R$^s$ is H or a $C_1$-$C_4$ alkyl group, or —S—;
$R^3$ is a straight chain or branched alkyl group having up to 10 carbon atoms, a straight chain or branched alkylaryl group having up to 20 carbon atoms, or siloxane group;
$R^4$ is —O—, —NR$^s$—, where R$^s$ is H or a $C_1$-$C_4$ alkyl group, —S—, —CH$_2$—;
$R^5$ is C=O, —CH$_2$—, a benzyl group, or a substituted benzyl group;
$R^6$ is H or a straight chain or branched alkyl group having up to 18 carbons atoms;
each $R^{12}$ is independently a bond, —CH$_2$—, —O—, or —NR$^s$—, where R$^s$ is H or a $C_1$-$C_4$ alkyl group;
$R^{13}$ is a substituted or unsubstituted aliphatic group having between 1 and 5000 carbon atoms and optionally including one or more heteroatoms selected from O, N, or S; —(CH$_2$—O—(CH$_2$—O)$_v$—CH$_2$)—; or a substituted or unsubstituted aromatic group having between 6 and 280 carbon atoms;

each of $R^{30}$ and $R^{31}$ is independently selected from I or H;

each $R^{34}$ is independently a bond, 4-hydroxybenzene, 3-iodo-4-hydroxybenzene, or 3,5-diiodo-4-hydroxybenzene;

each $R^{40}$ is independently O or NH;

T is H;

the terminating group is derived from an initiator;

b is an integer ranging from 0 to 1000;

n is 0 or an integer ranging from 1 to 8;

t is an integer ranging from 1 to 1000; and v is 0 or an integer ranging from 1 to 5000.

In another aspect of the present disclosure are compounds having the structure of Formula (VIIIA):

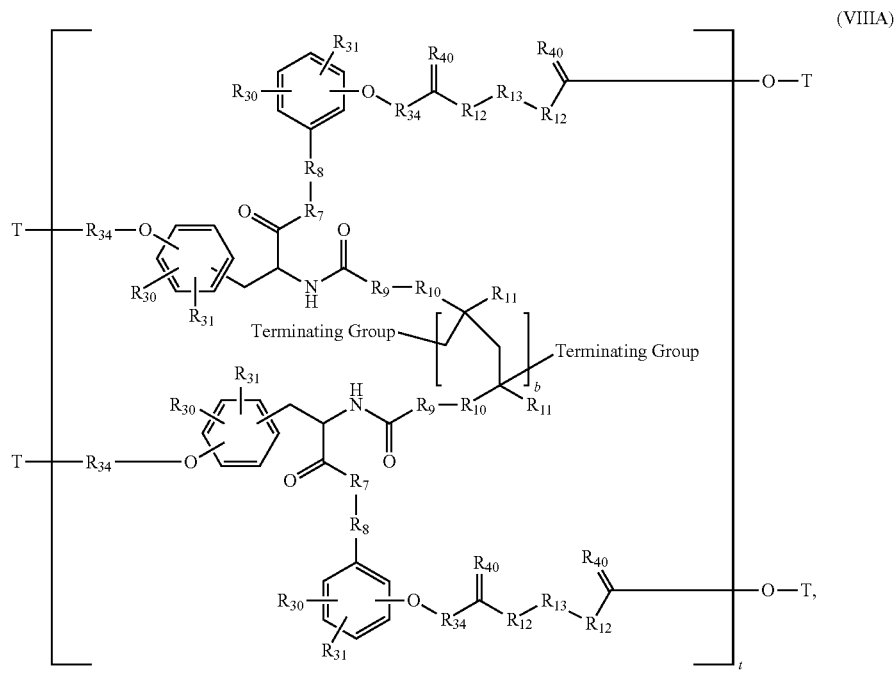

(VIIIA)

wherein
$R^7$ is —O—, —$NR^s$—, where $R^s$ is H or a $C_1$-$C_4$ alkyl group, —S—, —$CH_2$—;
$R^8$ is a saturated or unsaturated, substituted or unsubstituted, straight chain or branched alkyl group having between 1 and 20 carbon atoms;
$R^9$ is a bond, —O—, —$(CH_2)_m$—;
$R^{10}$ is a bond; a straight chain or branched alkyl group having up to 10 carbon atoms; a straight chain or branched alkylaryl group having up to 20 carbon atoms; —($CR^aR^b$—$CR^aR^bO)_p$—, —($CR^aR^b$—$CR^aR^b$—O$)_o$—C(O)— wherein $R^a$ and $R^b$ are independently H or a $C_1$-$C_4$ alkyl group; or a siloxane group;
$R^{11}$ is H or a straight chain or branched alkyl group having up to 18 carbons;
each $R^{12}$ is independently a bond, —$CH_2$—, —O—, or —$NR^{s\text{-}}$, where $R^s$ is H or a $C_1$-$C_4$ alkyl group;
$R^{13}$ is a substituted or unsubstituted aliphatic group having between 1 and 5000 carbon atoms and optionally including one or more heteroatoms selected from O, N, or S; —($CH_2$—O—($CH_2$—O$)_v$—$CH_2$)—; or a substituted or unsubstituted aromatic group having between 6 and 280 carbon atoms;
each of $R^{30}$ and $R^{31}$ is independently selected from I or H;
each $R^{34}$ is independently a bond, 4-hydroxybenzene, 3-iodo-4-hydroxybenzene, or 3,5-diiodo-4-hydroxybenzene;
each $R^{40}$ is independently O or NH;
T is H;
the terminating group is derived from an initiator;
b is an integer ranging from 0 to 1000;
m is 0 or an integer ranging from 1 to 8;
o is an integer ranging from 1 to 500;
t is an integer ranging from 1 to 1000; and
v is 0 or an integer ranging from 1 to 5000.

DETAILED DESCRIPTION

Figure 1:
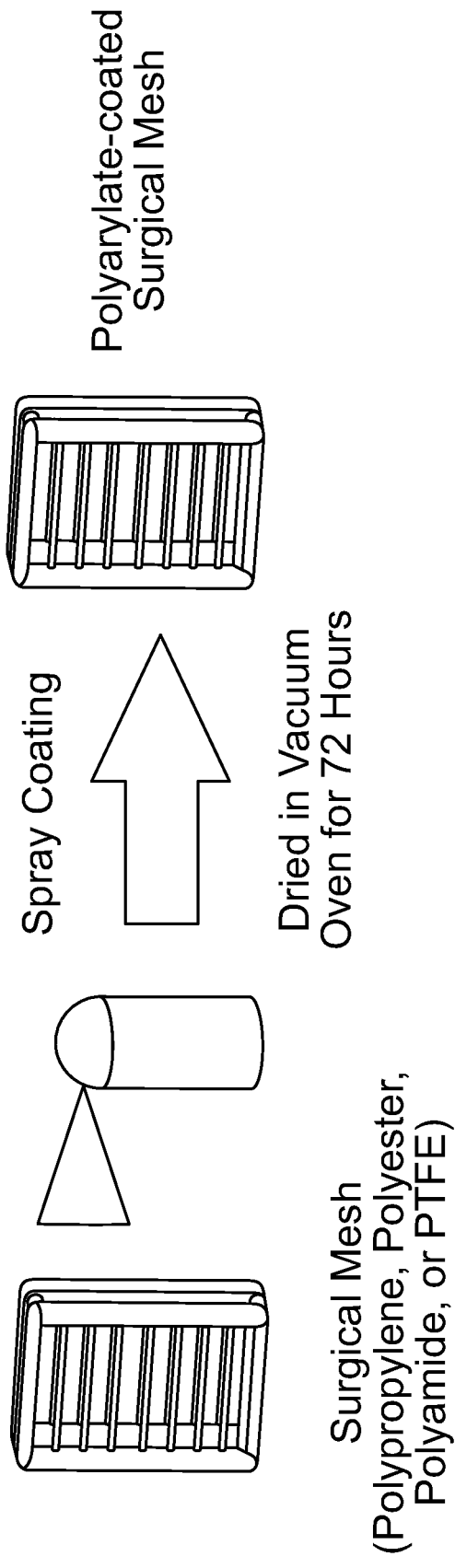
FIG. 1 illustrates a method of coating a medical device, e.g. a surgical mesh with a polyarylate resin, whereby the medical device is coating using a spray coating process. The polyarylate resin can be a combination of polyarylate and active pharmaceutical ingredients, e.g. antibiotics such as rifampin or minocycline, which can be solvated in suitable solvents, such as tetrahydrofuran, methanol, etc. The liquid resin is then spray coated onto a surgical mesh made from polypropylene, polyester, polytetrafluoroethylene, or polyamide, such that a minimum of 10 milligrams of the polymer/drug mixture is on each side of the surgical mesh. The coated mesh is then dried for a minimum of 72 hours in a vacuum oven prior to use.
Figure 2:
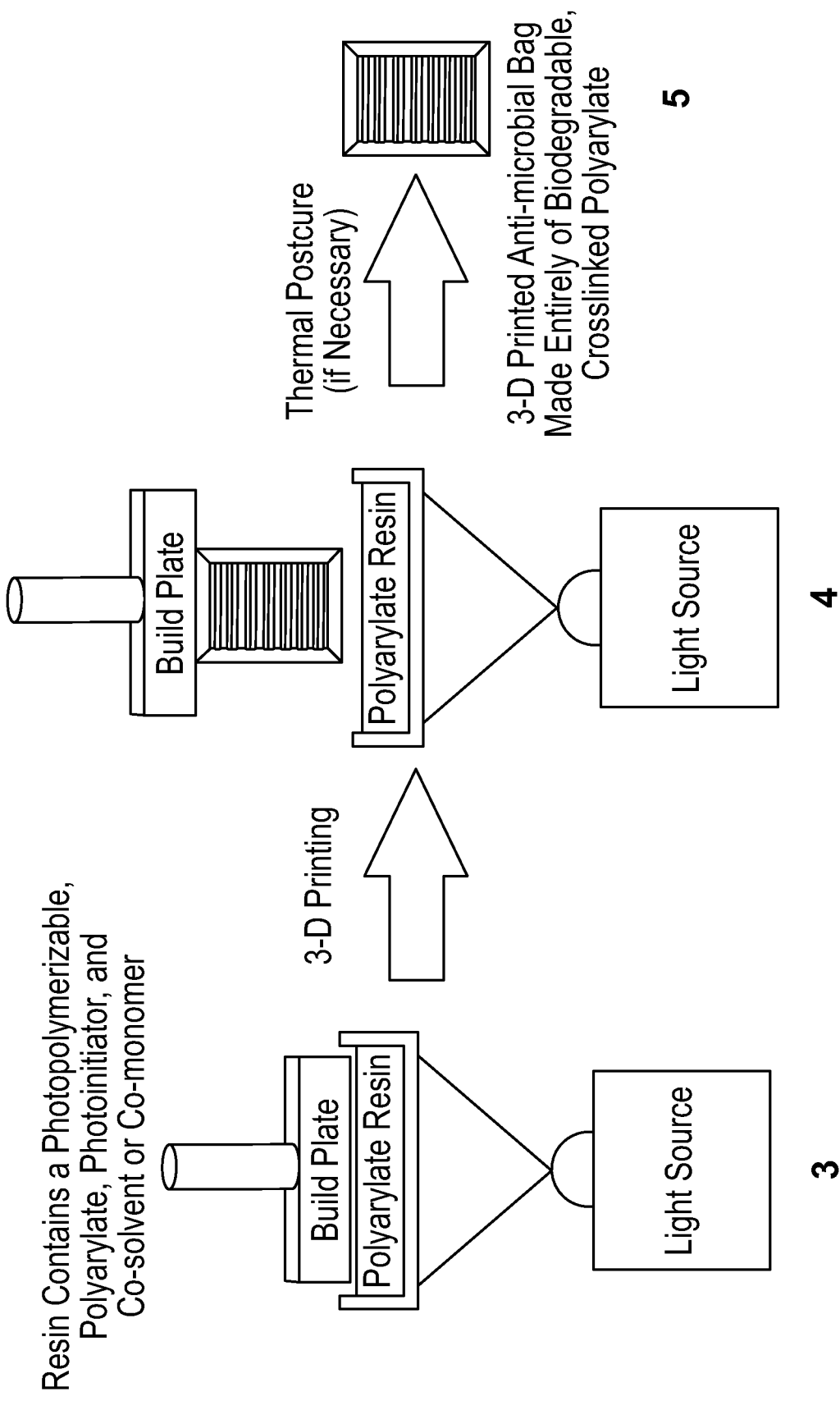
FIG. 2 illustrates a method of forming a medical device made of a polyarylate resin, whereby the medical device is made according to a 3D printing process. The medical device is composed entirely of the 3D printed polyarylate resin. The resin is composed of a novel 3D-printable polyarylate, photo initiator, and an active pharmaceutical ingredient, e.g. an antibiotic, which is dissolved in a solvent or co-monomer. The resin is then transferred into the reservoir of a DLP-style 3D printer, and the medical device is constructed entirely from photopolymerization of the resin, according to specifications of the 3D printing software.
Figure 3:
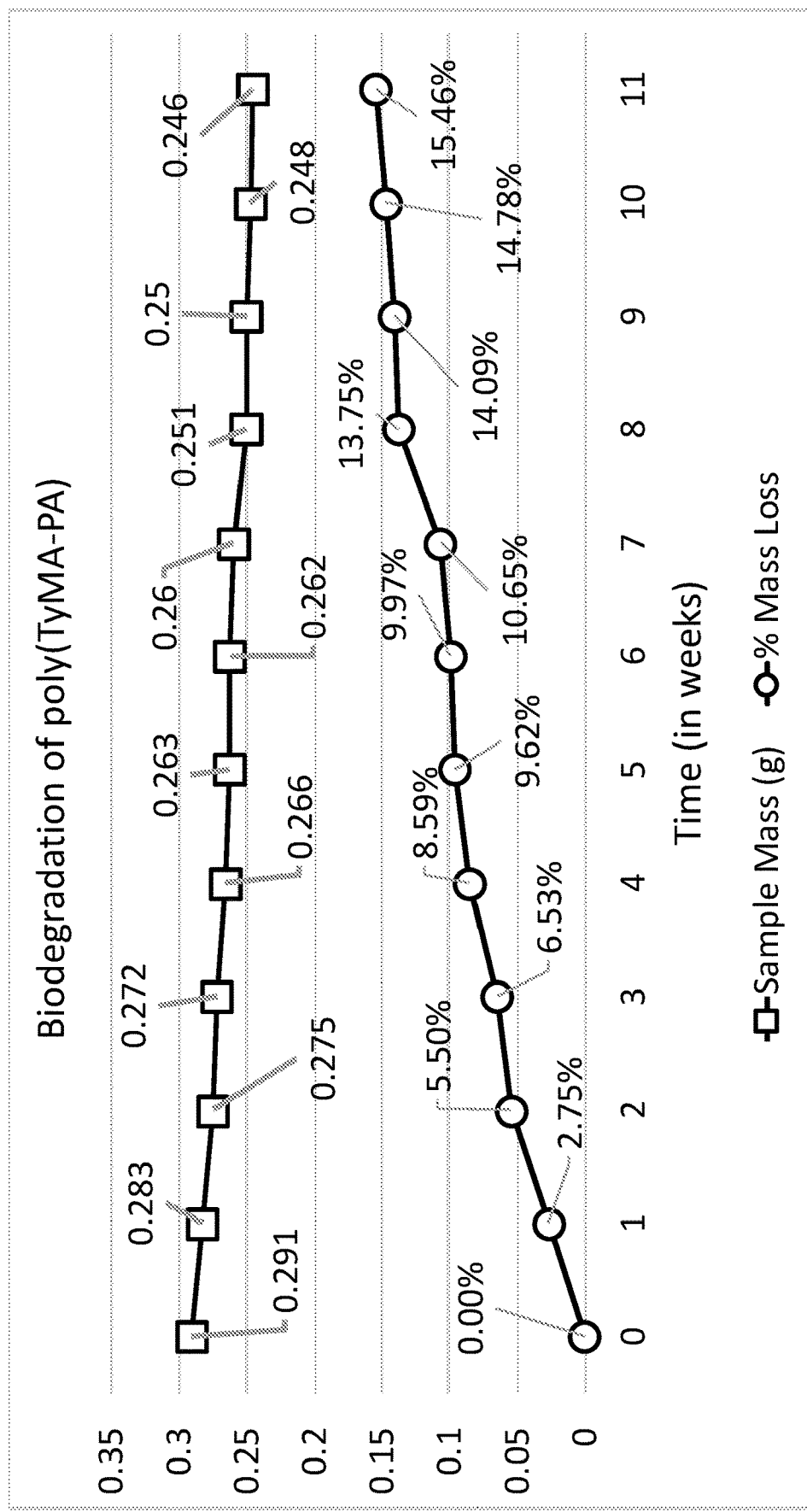
FIG. 3 provides graphs showing the biodegradation of poly(TyMA-PA) (see Example 7) over a time period of about 11 weeks.
Figure 4:
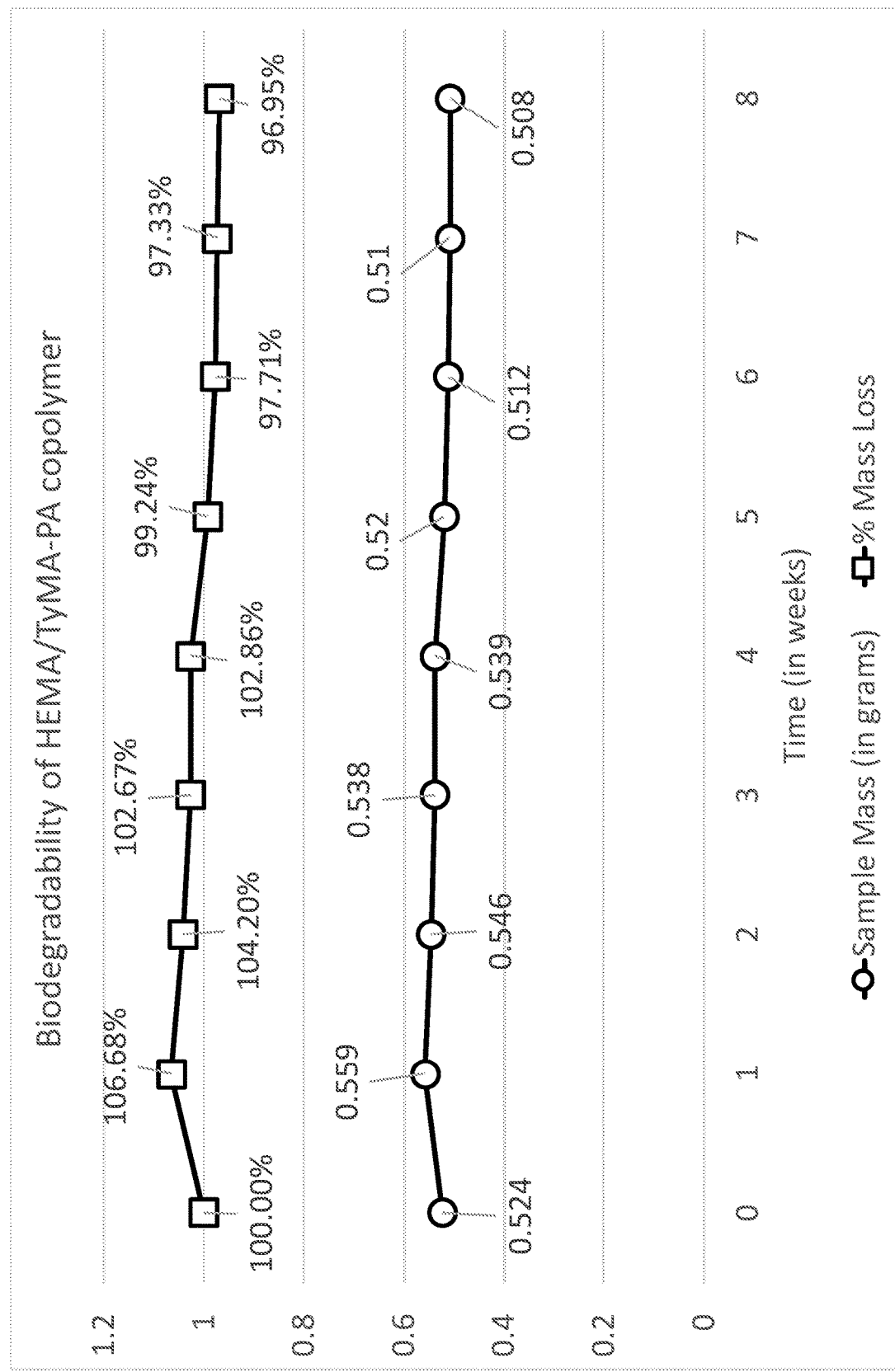
FIG. 4 provides graphs showing the biodegradation of a HEMA/TyMA-PA copolymer (see Example 8) over a time period of about 8 weeks.

An object of the disclosure is to provide biodegradable 3D printable resins, such as 3D printable polyarylate resins.

Definitions

It should also be understood that, unless clearly indicated to the contrary, in any methods claimed herein that include more than one step or act, the order of the steps or acts of the method is not necessarily limited to the order in which the steps or acts of the method are recited. It should also be understood that where a variable (e.g. "w") is used more than once in any formula or chemical structure, that each use of the variable in the formula or chemical structure is independent from any other use, unless explicitly noted otherwise. For example, if the variable "w" is used twice within the same formula, each "w'" may be the same or different, i.e. if "w" is defined as 0 or an integer ranging from 1 to 150, each "w" may independently be selected from 0 or an integer ranging from 1 to 150. Likewise, and again by way of example, if the moiety "$R^5$" is defined as —CH— or —C—$R^{12}$, then each time $R^5$ is used in a formula or chemical structure, each $R^5$ may independently be selected from —CH— or —C—$R^2$.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein in the specification and in the claims, the terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of."

As used herein, the term "alkyl" refers to a straight or branched hydrocarbon chain that comprises a fully saturated (no double or triple bonds) hydrocarbon group. By way of example only, the alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). As noted further herein, the alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, the term "alkenyl" refers to an alkyl group that contains in the straight or branched hydrocarbon chain one or more double bonds. An alkenyl group may be unsubstituted or substituted.

As used herein, the term "aryl" means an aromatic carbocyclic radical or a substituted carbocyclic radical containing preferably from 6 to 10 carbon atoms, such as phenyl or naphtyl or phenyl or naphtyl, optionally substituted by at least one of the substituents selected in the group constituted by alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acylamino, aroylamino, carbamoyl, alkylcarbamoyl, dialkylcarbamoyl, alkylthio, arylthio, alkylene or —NYY' where Y and Y' are independently hydrogen, alkyl, aryl, or aralkyl.

As used herein, the term "blend" refers, in some embodiments, to a mixture of two or more different species of resins or a resin and another polymer or copolymer.

As used herein, the terms "cure" or "curing" refer to processes of hardening a resin material.

As used herein, "cycloalkyl" of like terms (e.g. a cyclic alkyl group) refer to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl or aryl group, or the total number of carbon atoms and heteroatoms in a heteroalkyl, heterocyclyl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, the terms "halogen atom" or "halogen" mean any one of the radio-stable atoms of column 7 of the Periodic Table of the Elements, such as, fluorine, chlorine, bromine and iodine.

As used herein, the term "polymer" is defined as being inclusive of homopolymers, copolymers, interpenetrating networks, and oligomers. Thus, the term polymer may be used interchangeably herein with the term homopolymers, copolymers, interpenetrating polymer networks, etc. The term "homopolymer" is defined as a polymer derived from a single species of monomer. The term "copolymer" is defined as a polymer derived from more than one species of monomer, including copolymers that are obtained by copolymerization of two monomer species, those obtained from three monomers species ("terpolymers"), those obtained from four monomers species ("quaterpolymers"), etc. The term "oligomer" is defined as a low molecular weight polymer in which the number of repeating units does not exceed twenty. The term "copolymer" is further defined as being inclusive of random copolymers, alternating copolymers, graft copolymers, and block copolymers. Copolymers, as that term is used generally, include interpenetrating polymer networks. The term "random copolymer" is defined as a copolymer comprising macromolecules in which the probability of finding a given monomeric unit at any given site in the chain is independent of the nature of the adjacent units. In a random copolymer, the sequence distribution of monomeric units follows Bernoullian statistics. The term "alternating copolymer" is defined as a copolymer comprising macromolecules that include two species of monomeric units in alternating sequence.

Whenever a group or moiety is described as being "substituted" or "optionally substituted" (or "optionally having" or "optionally comprising") that group may be unsubstituted or substituted with one or more of the indicated substituents. Likewise, when a group is described as being "substituted or unsubstituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, cyanate, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, ether, amino (e.g. a mono-substituted amino group or a di-substituted amino group), and protected derivatives thereof. Any of the above groups may include one or more heteroatoms, including O, N, or S. For example, where a moiety is substituted with an alkyl group, that alkyl group may comprise a heteroatom selected from O, N, or S (e.g. —$(CH_2$—$CH_2$—O—$CH_2$—$CH_2)$—).

3D Printable Biocompositions

In some embodiments, the compounds of the present disclosure have the structure of Formula (IA):

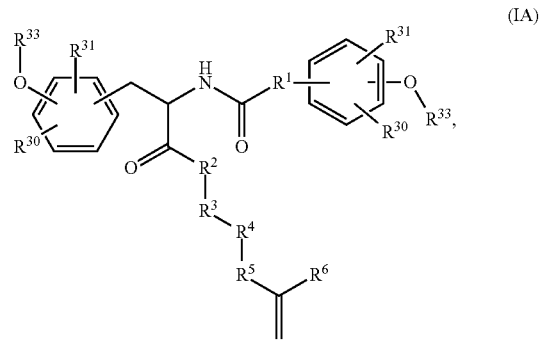

(IA)

wherein
$R^1$ is a saturated or unsaturated, straight chain or branched alkyl group having between 0 and 12 carbon atoms;
$R^2$ is —O—, —$NR^s$— where $R^s$ is H or a $C_1$-$C_4$ alkyl group, or —S—;
$R^3$ is a straight chain or branched alkyl group having up to 10 carbon atoms, a straight chain or branched alkylaryl group having up to 20 carbon atoms, or a siloxane group;
$R^4$ is —O—, —$NR^s$— where $R^s$ is H or a $C_1$-$C_4$ alkyl group, —S—, —$CH_2$—;
$R^5$ is —C(O)—, —$CH_2$—, —C(H)(Ph)- where Ph may include one or more substituents selected from —OH, a halogen, $C_1$-$C_4$ alkyl, or —$NR^s$— where $R^s$ is H or a $C_1$-$C_4$ alkyl group;
$R^6$ is H or a straight chain or branched alkyl group having up to 18 carbons atoms;
each of $R^{30}$ and $R^{31}$ are independently selected from I or H; and
each $R^{33}$ is independently H, —CN, 4-hydroxybenzene, 3-iodo-4-hydroxybenzene, or 3,5-diiodo-4-hydroxybenzene.

In some embodiments, $R^1$ is —CH=CH— or (—$CH_2$-$)_n$, wherein n ranges from 1 to 8. In some embodiments, n ranges from to 1 to 4. In other embodiments, $R^1$ is —$CH_2CH_2CH_2CH_2$—. In other embodiments, $R^1$ is —$CH_2CH_2CH_2$—. In yet other embodiments, $R^1$ is —$CH_2CH_2$—. In further embodiments, $R^1$ is —$CH_2$—.

In some embodiments, $R^3$ is a $C_1$-$C_8$ straight chain or branched alkyl group. In other embodiments, $R^3$ is a $C_1$-$C_6$ straight chain or branched alkyl group. In yet other embodiments, $R^3$ is a $C_1$-$C_4$ straight chain or branched alkyl group.

In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 16 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 12 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 9 carbon atoms.

In some embodiments, the siloxane group has the structure of —$(R''')(R'')$—Si—O—Si—$(R'')(R''')$—, or —$(R''')(R'')$—Si—[O—Si—$(R'')(R''')$]$_h$—O—Si—$(R'')(R''')$—, wherein $R'''$ and $R''$ are independently selected from $C_1$-$C_4$ alkyl, C6 aryl, or H, and wherein h ranges from 1 to 2000. In some embodiments, h ranges from 1 to 1500. In other embodiments, h ranges from 1 to 1000. In yet other embodiments, h ranges from 1 to 750. In further embodiments, h ranges from 1 to 500. In yet further embodiments, h ranges from 1 to 250.

In some embodiments, $R^3$ is 2,2,-dimethyl propane or sec-butane. In other embodiments, $R^3$ is derived from 2,2-diphenyl propane. In some embodiments, $R^3$ is derived from poly(dimethylsiloxane) having a molecular weight ranging from about 70 to about 100,000; or derived from poly(diarylsiloxane) having a molecular weight ranging from about 190 to about 100,000.

In some embodiments, $R^5$ is —C(O)—, —$CH_2$— or —C(H)(Ph)-. In some embodiments, $R^5$ is —$CH_2$—. In some embodiments, $R^5$ is —C(O)—.

In some embodiments, $R^6$ is H. In other embodiments, $R^6$ is a $C_1$-$C_8$ straight chain or branched alkyl group. In other embodiments, $R^6$ is a $C_1$-$C_6$ straight chain or branched alkyl group. In yet other embodiments, $R^6$ is a $C_1$-$C_4$ straight chain or branched alkyl group. In further embodiments, $R^6$ is methyl.

In some embodiments, each $R^{30}$ and each $R^{31}$ is H. In some embodiments, each $R^{33}$ is —CN. In some embodiments, each $R^{30}$, $R^{31}$, and $R^{33}$ is H.

The skilled artisan will appreciate that the compounds of Formula (IA) and any compound derived from or based thereon, may include the chirality depicted in the structures set forth below:

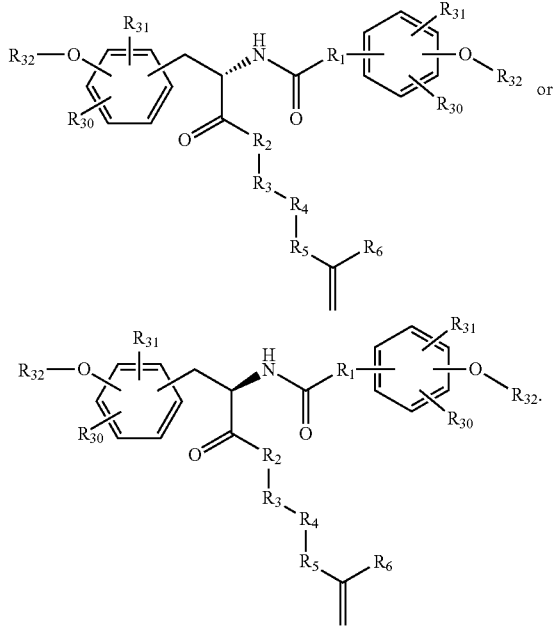

In some embodiments, the compounds of the present disclosure have the structure of Formula (IB):

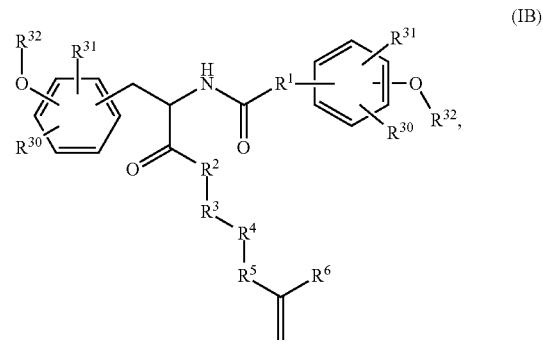

wherein
$R^1$ is —CH=CH— or (—$CH_2$—);
$R^2$ is —O—, —$NR^s$—, where $R^s$ is H or a $C_1$-$C_4$ alkyl group, or —S—;
$R^3$ is a straight chain or branched alkyl group having up to 10 carbon atoms, a straight chain or branched alkylaryl group having up to 20 carbon atoms, or siloxane group;
$R^4$ is —O—, —$NR^s$—, where $R^s$ is H or a C1-$C_4$ alkyl group, —S—, —$CH_2$—;
$R^5$ is —C(O)—, —$CH_2$—, —C(H)(Ph)- where Ph may include one or more substituents selected from —OH, a halogen, $C_1$-$C_4$ alkyl, or —$NR^s$— where $R^s$ is H or a $C_1$-$C_4$ alkyl group;
$R^6$ is H or a straight chain or branched alkyl group having up to 18 carbons atoms;
each of $R^{30}$ and $R^{31}$ are independently selected from I or H;
each $R^{32}$ is independently H, 4-hydroxybenzene, 3-iodo-4-hydroxybenzene, or 3,5-diiodo-4-hydroxybenzene; and
n is 0 or an integer ranging from 1 to 8.

In some embodiments, $R^1$ is —$CH_2CH_2CH_2CH_2$—. In other embodiments, $R^1$ is —$CH_2CH_2CH_2$—. In yet other embodiments, $R^1$ is —$CH_2CH_2$—. In further embodiments, $R^1$ is —$CH_2$—.

In some embodiments, $R^3$ is a $C_1$-$C_8$ straight chain or branched alkyl group. In other embodiments, $R^3$ is a $C_1$-$C_6$ straight chain or branched alkyl group. In yet other embodiments, $R^3$ is a $C_1$-$C_4$ straight chain or branched alkyl group.

In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 16 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 12 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 9 carbon atoms.

In some embodiments, the siloxane group has the structure of —$(R''')(R'')$—Si—O—Si—$(R'')(R''')$—, or —$(R''')(R'')$—Si—[O—Si—$(R'')(R''')$]$_h$—O—Si—$(R'')(R''')$—, wherein $R'''$ and $R''$ are independently selected from $C_1$-$C_4$ alkyl, $C_6$ aryl, or H and wherein h ranges from 1 to 2000. In some embodiments, h ranges from 1 to 1500. In other embodiments, h ranges from 1 to 1000. In yet other embodiments, h ranges from 1 to 750. In further embodiments, h ranges from 1 to 500. In yet further embodiments, h ranges from 1 to 250.

In some embodiments, $R^3$ is 2,2,-dimethyl propane or sec-butane. In other embodiments, $R^3$ is derived from 2,2-diphenyl propane. In some embodiments, $R^3$ is derived from poly(dimethylsiloxane) having a molecular weight ranging from about 70 to about 100,000; or derived from poly (diarylsiloxane) having a molecular weight ranging from about 190 to about 100,000. In some embodiments, $R^6$ is H. In other embodiments, $R^6$ is a $C_1$-$C_8$ straight chain or branched alkyl group. In other embodiments, $R^6$ is a $C_1$-$C_6$ straight chain or branched alkyl group. In yet other embodiments, $R^6$ is a $C_1$-$C_4$ straight chain or branched alkyl group. In further embodiments, $R^6$ is methyl.

In some embodiments, $R^5$ is —C(O)—, —CH$_2$— or —C(H)(Ph)-. In some embodiments, $R^5$ is —CH$_2$—. In some embodiments, $R^5$ is —C(O)—.

In some embodiments, each $R^{30}$ and each $R^{31}$ is H.

Examples of compounds having Formula (IB) include:

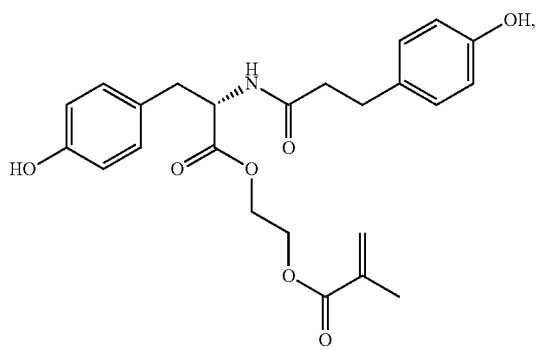

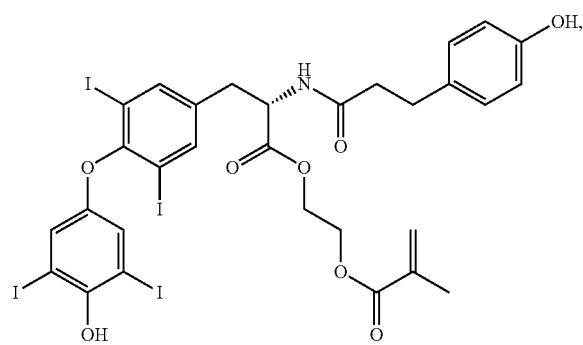

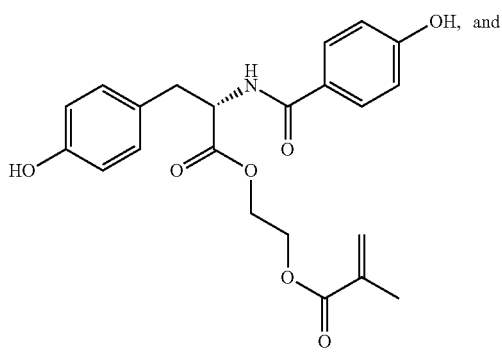

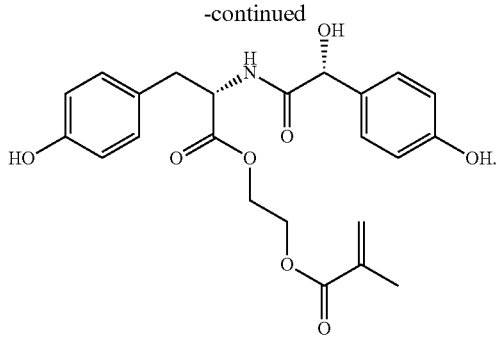

In some embodiments, the compounds of the present disclosure have the structure of Formula (IC):

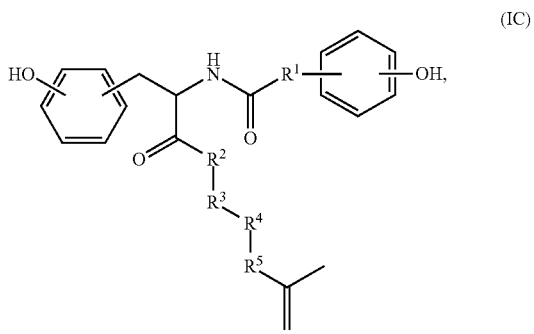

(IC)

$R^1$ is —CH=CH— or (—CH$_2$-)$_n$;

$R^2$ is —O—, —NR$^s$—, where $R^s$ is H or a $C_1$-$C_4$ alkyl group, or —S—;

$R^3$ is a straight chain or branched alkyl group having up to 10 carbon atoms, a straight chain or branched alkylaryl group having up to 20 carbon atoms, or a siloxane group;

$R^4$ is —O—, —NR$^s$—, where $R^s$ is H or a $C_1$-$C_4$ alkyl group, —S—, —CH$_2$—;

R is —C(O)—, —CH$_2$— or —C(H)(Ph)-;

n ranges from 1 to 8.

In some embodiments, $R^1$ is —CH$_2$CH$_2$CH$_2$—. In yet other embodiments, $R^1$ is —CH$_2$CH$_2$—. In further embodiments, $R^1$ is —CH$_2$—.

In some embodiments, at least one of $R^2$ or $R^4$ is —O—; $R^3$ is a straight chain or branched $C_1$-$C_6$ alkyl group; and $R^1$ is a $C_1$-$C_6$ alkyl group. In other embodiments, both of $R^2$ and $R^4$ are —O—; $R^3$ is a straight chain or branched $C_1$-$C_6$ alkyl group; and $R^1$ is a $C_1$-$C_6$ alkyl group. In yet other embodiments, both of $R^2$ and $R^4$ are —O—; $R^3$ is a straight chain or branched $C_1$-$C_6$ alkyl group; $R^1$ is a $C_1$-$C_6$ alkyl group; and $R^5$ is C=O. In further embodiments, both of $R^2$ and $R^4$ are —O—; $R^3$ is a straight chain or branched $C_1$-$C_6$ alkyl group; $R^1$ is a $C_1$-$C_6$ alkyl group; and R is —CH$_2$—.

In some embodiments, R is C=O or —CH$_2$—.

In some embodiments, the compounds of the present disclosure have the structure of Formula (ID):

(ID)

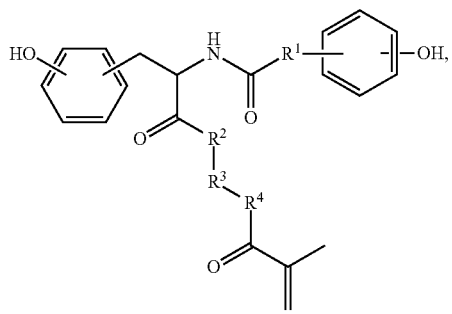

$R^1$ is —CH=CH— or (—CH$_2$—)$_n$;
$R^2$ is —O—, —NR$^s$—, where R$^s$ is H or a C$_1$-C$_4$ alkyl group, or —S—;
$R^3$ is a straight chain or branched alkyl group having up to 10 carbon atoms, a straight chain or branched alkylaryl group having up to 20 carbon atoms, or a siloxane group;
$R^4$ is —O—, —NR$^s$—, where R$^s$ is H or a C1-C$_4$ alkyl group, —S—, —CH$_2$—; and
n ranges from 1 to 8.

In some embodiments, at least one of $R^2$ or $R^4$ is —O—.

In some embodiments, $R^3$ is a straight chain or branched C$_1$-C$_6$ alkyl group. In other embodiments, $R^3$ is a straight chain or branched C$_1$-C$_4$ alkyl group.

In some embodiments, at least one of $R^2$ or $R^4$ is —O—; $R^3$ is a straight chain or branched C$_1$-C$_4$ alkyl group; and $R^1$ is a C$_1$-C$_4$ alkyl group. In other embodiments, both of $R^2$ and $R^4$ are —O—; $R^3$ is a straight chain or branched C$_1$-C$_4$ alkyl group; and $R^1$ is a C$_1$-C$_4$ alkyl group. In yet other embodiments, both of $R^2$ and $R^4$ are —O—; $R^3$ is a straight chain or branched C$_1$-C$_4$ alkyl group; and $R^1$ is a C$_1$-C$_4$ alkyl group, provided that at least one of $R^1$ or $R^3$ is —CH$_2$—.

In some embodiments, the compounds of the present disclosure have the structure of Formula (IE):

(IE)

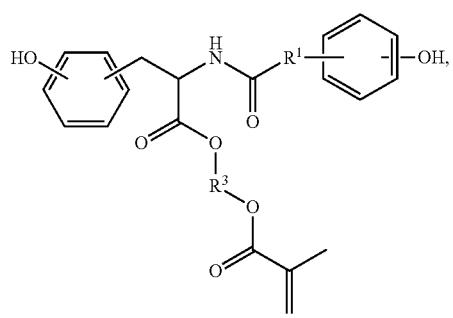

$R^1$ is —CH=CH— or (—CH$_2$—)$_n$;
$R^3$ is a straight chain or branched alkyl group having up to 10 carbon atoms, a straight chain or branched alkylaryl group having up to 20 carbon atoms, or a siloxane group; and
n ranges from 1 to 8.

In some embodiments, $R^3$ is a C$_1$-C$_4$ alkyl group. In some embodiments, $R^3$ is —CH$_2$—CH$_2$—. In some embodiments, $R^3$ is —CH$_2$—.

In some embodiments, at least one or R or $R^3$ is —CH$_2$—. In some embodiments, at least one or R or $R^3$ is —CH$_2$— and another of $R^1$ or $R^3$ is —CH$_2$CH$_2$—. In some embodiments, both $R^1$ and $R^3$ are —CH$_2$—.

In some embodiments, the compounds of the present disclosure have the structure of Formula (IIA):

(IIA)

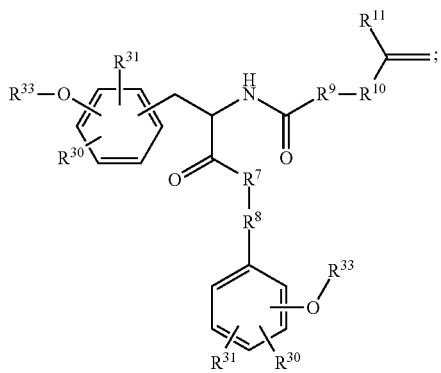

wherein
$R^1$ is —O—, —NR$^s$— where R$^s$ is H or a C$_1$-C$_4$ alkyl group, —S—, —CH$_2$—;
$R^8$ is a saturated or unsaturated, substituted or unsubstituted, straight chain or branched alkyl group having between 1 and 20 carbon atoms;
$R^9$ is a bond, —O—, —(CH$_2$)$_m$—;
$R^{10}$ is a bond; a straight chain or branched alkyl group having up to 10 carbon atoms; a straight chain or branched alkylaryl group having up to 20 carbon atoms; —(CR$^a$R$^b$—CR$^a$R$^b$O)$_o$—, —(CR$^a$R$^b$—CR$^a$R$^b$—O)$_o$C(O)— wherein R$^a$ and R$^b$ are independently H or a C$_1$-C$_4$ alkyl group; or a siloxane group;
$R^{11}$ is H or a straight chain or branched alkyl group having up to 18 carbons;
each of $R^{30}$ and $R^{31}$ are independently selected from I or H;
each $R^{33}$ is independently H, —CN, 4-hydroxybenzene, 3-iodo-4-hydroxybenzene, or 3,5-diiodo-4-hydroxybenzene;
m is 0 or an integer ranging from 1 to 8; and
each o is an integer ranging from 1 to 500.

In some embodiments, o is an integer ranging from 1 to 400. In other embodiments, o is an integer ranging from 1 to 300. In yet other embodiments, o is an integer ranging from 1 to 200. In further embodiments, o is an integer ranging from 1 to 100. In yet further embodiments, o is an integer ranging from 1 to 50.

In some embodiments, $R^8$ is —CH=CH— or (—CH$_2$—)$_n$, wherein n ranges from 1 to 20. In some embodiments, n ranges from to 1 to 16. In other embodiments, n ranges from to 1 to 16. In yet other embodiments, n ranges from to 1 to 12. In further embodiments, n ranges from to 1 to 8. In even further embodiments, n ranges from to 1 to 6. In some embodiments, $R^8$ is —CH$_2$CH$_2$CH$_2$CH$_2$—. In other embodiments, $R^8$ is —CH$_2$CH$_2$CH$_2$—. In yet other embodiments, $R^8$ is —CH$_2$CH$_2$—. In further embodiments, $R^8$ is —CH$_2$—.

In some embodiments, $R^{10}$ is —(CH$_2$)$_p$—, where p ranges from 1 to 12. In some embodiments, p ranges from 1 to 6. In other embodiments, p ranges from 1 to 4. In yet other embodiments, p is 1 or 2.

In some embodiments, $R^{10}$ is —(CH$_2$CH$_2$O)$_o$—, —(CH$_2$CH$_2$O)$_o$C(O)—, where o ranges from 1 to 250. In some embodiments, $R^{10}$ is —(CH$_2$CH$_2$O)$_o$—, —(CH$_2$CH$_2$O)$_o$C(O)—, where o ranges from 1 to 100. In some embodiments, $R^{10}$ is —(CH$_2$CH$_2$O)$_o$—, —(CH$_2$CH$_2$O)$_o$C(O)—, where o ranges from 1 to 50. In some embodiments, R$^{10}$ is —(CH$_2$CH$_2$O)$_o$—, —(CH$_2$CH$_2$O)$_o$C(O)—, where o ranges from 1 to 10. In other embodiments, R$^{10}$ is —(CH$_2$CH$_2$O)$_o$—, —(CH$_2$CH$_2$O)$_o$C(O)—, where o ranges from 1 to 6.

In some embodiments, R$^{11}$ is H. In other embodiments, R$^{11}$ is methyl.

In some embodiments, each R$^{33}$ is —CN.

The skilled artisan will appreciate that the compounds of Formula (IIA) and any compound derived from or based thereon, may include the chirality depicted in the structure set forth below:

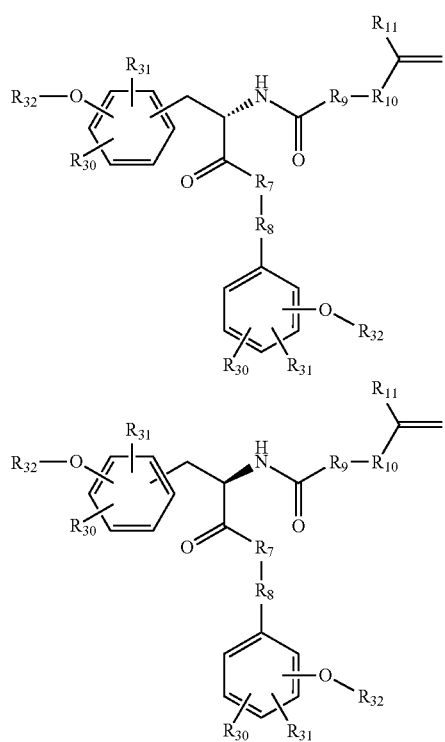

In some embodiments, the compounds of the present disclosure have the structure of Formula (IIB):

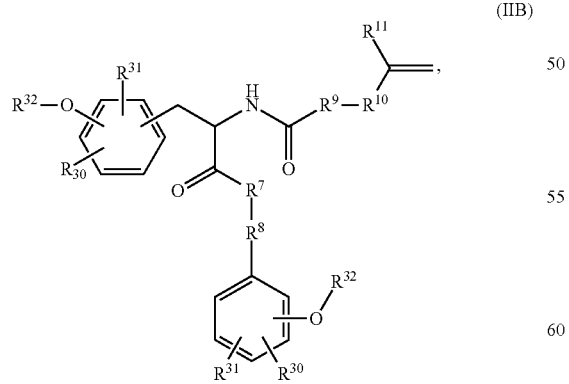

wherein
R$^7$ is —O—, —NR$^s$—, where R$^s$ is H or a C$_1$-C$_4$ alkyl group, —S—, —CH$_2$—;
R$^8$ is —CH=CH— or (—CH$_2$—);

R$^9$ is a bond, —O— or (—CH$_2$-)$_m$;
R$^{10}$ is a bond, —(CH$_2$CH$_2$O)$_o$—, —(CH$_2$CH$_2$O)$_o$C(O)—, a straight chain or branched alkyl group having up to 10 carbon atoms, a straight chain or branched alkylaryl group having up to 20 carbon atoms, or a siloxane group;

R$^{11}$ is H or a straight chain or branched alkyl group having up to 18 carbons;

each of R$^{30}$ and R$^{31}$ are independently selected from I or H;

each R$^{32}$ is independently H, 4-hydroxybenzene, 3-iodo-4-hydroxybenzene, or 3,5-diiodo-4-hydroxybenzene; and m and n are independently 0 or an integer ranging from 1 to 8; and each o is independently 0 or an integer ranging from 1 to 500.

In some embodiments, R$^7$ is —NH—, and R$^8$ is —(CH$_2$)$_n$—. In some embodiments, R$^7$ is —NH—, and R$^8$ is —(CH$_2$)$_n$—, where n is an integer ranging from 1 to 4. In other embodiments, R$^1$ is —NH—, and R$^8$ is —(CH$_2$)$_n$— where n is an integer ranging from 1 to 2.

In some embodiments, R$^{10}$ is —(CH$_2$)$_p$—, where p is an integer ranging from 1 to 8. In some embodiments, R$^{10}$ is —CH$_2$CH$_2$CH$_2$CH$_2$—. In other embodiments, R$^{10}$ is —CH$_2$CH$_2$CH$_2$—. In yet other embodiments, R$^{10}$ is —CH$_2$CH$_2$—. In further embodiments, R$^{10}$ is —CH$_2$—.

In some embodiments, R$^{11}$ is a C$_1$-C$_6$ alkyl group. In some embodiments, R$^{11}$ is a C$_1$-C$_4$ alkyl group. In some embodiments, R$^{11}$ is a C$_1$-C$_6$ alkyl group. In some embodiments, R$^{11}$ is a C$_1$-C$_3$ alkyl group. In some embodiments, R$^{11}$ is a C$_1$-C$_6$ alkyl group. In some embodiments, R$^{11}$ is a C$_1$-C$_2$ alkyl group. In some embodiments, R$^{11}$ is methyl.

In some embodiments, both R$^9$ and R$^{10}$ are bonds.

Examples of compounds having Formula (IIB) include:

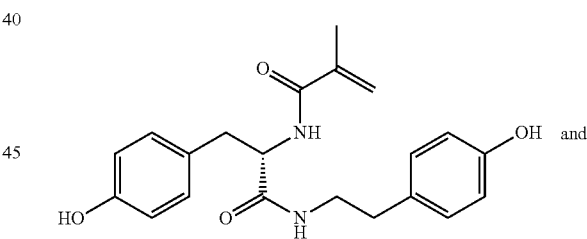

and

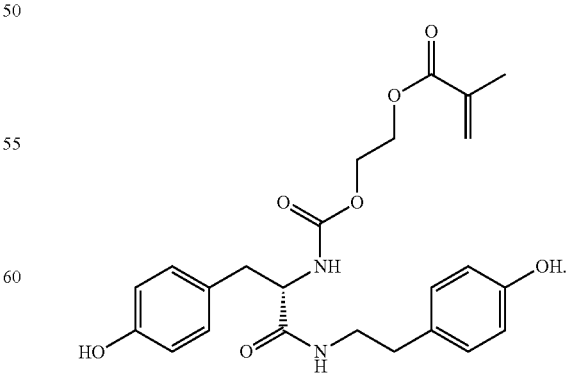

In some embodiments, the compounds of the present disclosure have the structure of Formula (IIC):

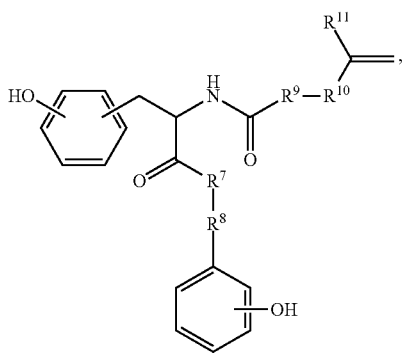

(IIC)

wherein
$R^7$ is —O—, —$NR^s$—, where $R^s$ is H or a $C_1$-$C_4$ alkyl group, —S—, —$CH_2$—;
$R^8$ is -CH=CH— or —$(CH_2)_n$—;
$R^9$ is a bond, —O— or (—$CH_2$-$)_m$;
$R^{10}$ is a bond, —$(CH_2CH_2O)_o$—, —$(CH_2CH_2O)_oC(O)$—, a straight chain or branched alkyl group having up to 10 carbon atoms, a straight chain or branched alkylaryl group having up to 20 carbon atoms, or a siloxane group;
$R^{11}$ is H or a straight chain or branched alkyl group having up to 18 carbons;
m and n are independently 0 or an integer ranging from 1 to 8; and
each o is independently 0 or an integer ranging from 1 to 500.

In some embodiments, $R^7$ is —NH—, and $R^8$ is —$(CH_2)_n$—. In some embodiments, $R^7$ is —NH—, and $R^8$ is —$(CH_2)_n$—, where n is an integer ranging from 1 to 4. In other embodiments, $R^1$ is —NH—, and $R^8$ is —$(CH_2)_n$— where n is an integer ranging from 1 to 2.

In some embodiments, $R^{11}$ is a $C_1$-$C_6$ alkyl group. In some embodiments, $R^{11}$ is a $C_1$-$C_4$ alkyl group. In some embodiments, $R^{11}$ is a $C_1$-$C_6$ alkyl group. In some embodiments, $R^{11}$ is a $C_1$-$C_3$ alkyl group. In some embodiments, $R^{11}$ is a $C_1$-$C_6$ alkyl group. In some embodiments, $R^{11}$ is a $C_1$-$C_2$ alkyl group. In some embodiments, $R^{11}$ is methyl.

In some embodiments, both $R^9$ and $R^{10}$ are bonds.
In some embodiments, the compounds of the present disclosure have the structure of Formula (IID):

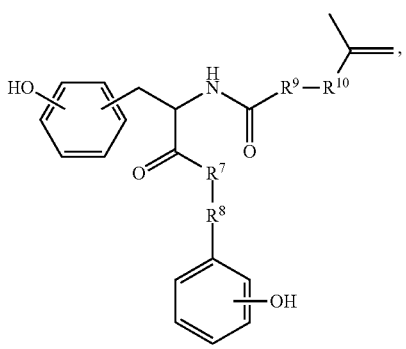

(IID)

wherein
$R^7$ is —O—, —$NR^s$—, where $R^s$ is H or a $C_1$-$C_4$ alkyl group, —S—, —$CH_2$—;
$R^8$ is -CH=CH— or —$(CH_2)_n$—;

$R^9$ is a bond, —O— or (—$CH_2$-$)_m$;
$R^{10}$ is a bond, —$(CH_2CH_2O)_o$—, —$(CH_2CH_2O)_oC(O)$—, a straight chain or branched alkyl group having up to 10 carbon atoms, a straight chain or branched alkylaryl group having up to 20 carbon atoms, or a siloxane group;
m and n are independently 0 or an integer ranging from 1 to 8; and
each o is independently 0 or an integer ranging from 1 to 500.

In some embodiments, $R^7$ is —NH—, and $R^8$ is —$(CH_2)_n$—. In some embodiments, $R^7$ is —NH—, and $R^8$ is —$(CH_2)_n$—, where n is an integer ranging from 1 to 4. In other embodiments, $R^7$ is —NH—, and $R^8$ is —$(CH_2)_n$—, where n is an integer ranging from 1 to 2.

In some embodiments, both $R^9$ and $R^{10}$ are bonds.
In some embodiments, the compounds of the present disclosure have the structure of Formula (IIE):

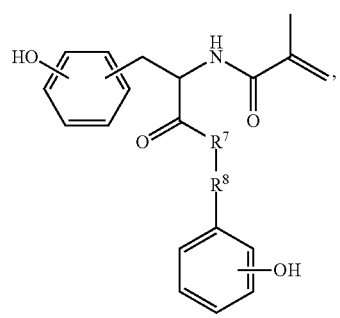

(IIE)

$R^7$ is —O—, —$NR^s$—, where $R^s$ is H or a $C_1$-$C_4$ alkyl group, —S—, —$CH_2$—;
$R^8$ is -CH=CH— or (—$CH_2$-$)_n$; and
n is independently 0 or an integer ranging from 1 to 8.

In some embodiments, $R^7$ is —NH—, and $R^8$ is —$(CH_2)_n$—. In some embodiments, $R^7$ is —NH—, and $R^8$ is —$(CH_2)_n$—, where n is an integer ranging from 1 to 4. In other embodiments, $R^7$ is —NH—, and $R^8$ is —$(CH_2)_n$, where n is an integer ranging from 1 to 2.

In some embodiments, the compounds of the present disclosure have the structure of Formula (IIF):

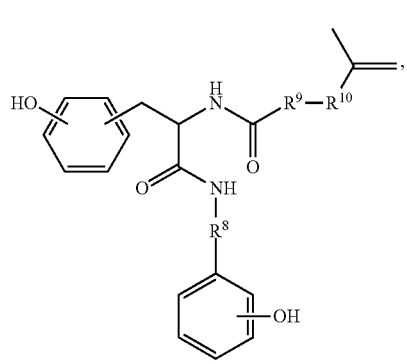

(IIF)

wherein
$R^8$ is -CH=CH— or (—$CH_2$-$)_n$;
$R^9$ is a bond, —O— or (—$CH_2$-$)_m$;
$R^{10}$ is a bond, —$(CH_2CH_2O)_o$—, —$(CH_2CH_2O)_oC(O)$—, a straight chain or branched alkyl group having up to 10 carbon atoms, a straight chain or branched alkylaryl group having up to 20 carbon atoms, or a siloxane group;

m and n are independently 0 or an integer ranging from 1 to 8; and each o is independently 0 or an integer ranging from 1 to 500.

In some embodiments, $R^8$ is —$(CH_2)_n$—. In some embodiments, $R^8$ is —$(CH_2)_n$—, where n is an integer ranging from 1 to 4. In other embodiments, $R^8$ is —$(CH_2)_n$—, where n is an integer ranging from 1 to 2.

Reaction Products of the Compounds of Formulas (IA)-(IE) and (IIA)-(IIF)

In some embodiments, the compounds of Formulas (IA), (IB), (IC), (ID), (IE), (IIA), (IIB), (IIC), (IID), (IIE), and (IIF) may be reacted with a diacid, a diisocyanate, or a cyanate ester to provide at least the compounds of Formulas (IIIA), (IVA), (VA), and (VIA), herein.

Reaction Products of the Compounds of Formulas (IA), (IB), (IC), (ID), and (IE) with a Diacid or Diisocyanate In some embodiments, the compounds of Formulas (IA), (IB), (IC), (ID), and (IE), are reacted with a diacid or a diisocyanate to provide the compounds of any of Formulas (IIIA) to (IIIG). Suitable diacids for reaction with the compounds of Formulas (IA)-(IE) and (IIA)-(IIF) include, but are not limited to, maleic acid, fumaric acid, malic acid, oxalic acid, malonic acid, succinic acid, adipic acid, butaneioic acid, decanedioic acid, itaconic acid, citric acid, glutaric acid, pimelic acid, suberic acid, sebacic acid, phthalic acid, terephthalic acid, isophthalic acid, and malonic acid.

Suitable diisocyanates for reaction with the compounds of Formulas (IA)-(IE) and (IIA)-(IIF) include, but are not limited to, toluene diisocyanate (TDI), methylenediphenyl isocyanate (MDI), isophorone diisocyanate (IPDI), methylene dicyclohexyl diisocyanate (commonly referred to as hydrogenated MDI or HMDI), and hexamethylene diisocyanate (HDI).

In some embodiments, the compounds of the present disclosure have the structure of Formula (IIIA):

$R^6$ is H or a straight chain or branched alkyl group having up to 18 carbons atoms;

each $R^{12}$ is independently a bond, —$CH_2$—, —O—, or —$NR^s$—, where $R^s$ is H or a $C_1$-$C_4$ alkyl group;

$R^{13}$ is a substituted or unsubstituted aliphatic group having between 1 and 5000 carbon atoms and optionally including one or more heteroatoms selected from O, N, or S; —$(CH_2$—O—$(CH_2$—O$)_v$—$CH_2)$—; or a substituted or unsubstituted aromatic group having between 6 and 280 carbon atoms;

each of $R^{30}$ and $R^{31}$ is independently selected from I or H;

each $R^{34}$ is independently a bond, 4-hydroxybenzene, 3-iodo-4-hydroxybenzene, or 3,5-diiodo-4-hydroxybenzene;

each $R^{40}$ is independently O or NH;

T is H;

n is 0 or an integer ranging from 1 to 8;

t is an integer ranging from 1 to 1000; and v is 0 or an integer ranging from 1 to 5000.

In some embodiments, $R^1$ is —CH=CH— or (—$CH_2$-$)_n$, wherein n ranges from 1 to 8. In some embodiments, n ranges from to 1 to 4. In other embodiments, $R^1$ is —$CH_2CH_2CH_2CH_2$—. In other embodiments, $R^1$ is —$CH_2CH_2CH_2$—. In yet other embodiments, $R^1$ is —$CH_2CH_2$—. In further embodiments, $R^1$ is —$CH_2$—.

In some embodiments, $R^3$ is a $C_1$-$C_8$ straight chain or branched alkyl group. In other embodiments, $R^3$ is a $C_1$-$C_6$ straight chain or branched alkyl group. In yet other embodiments, $R^3$ is a $C_1$-$C_4$ straight chain or branched alkyl group.

In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 16 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 12 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 9 carbon atoms.

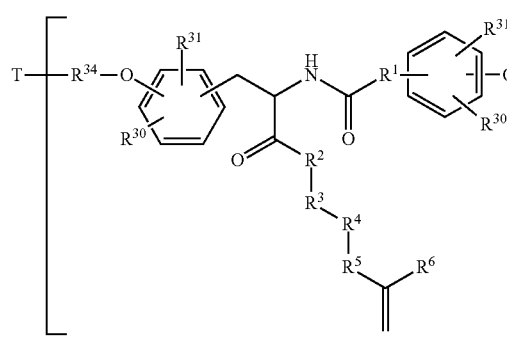

(IIIA)

wherein $R^1$ is —CH=CH— or (—$CH_2$-$)_n$;

$R^2$ is —O—, —$NR^s$—, where $R^s$ is H or a $C_1$-$C_4$ alkyl group, or —S—;

$R^3$ is a straight chain or branched alkyl group having up to 10 carbon atoms, a straight chain or branched alkylaryl group having up to 20 carbon atoms, or siloxane group;

$R^4$ is —O—, —$NR^s$—, where $R^s$ is H or a $C_1$-$C_4$ alkyl group, —S—, —$CH_2$—;

$R^5$ is C=O, —$CH_2$—, a benzyl group, or a substituted benzyl group;

In some embodiments, the siloxane group has the structure of —$(R^m)(R^n)$—Si—O—Si—$(R^n)(R^m)$—, or —$(R^m)(R^n)$—Si—[O—Si—$(R^n)(R^m)]_h$—O— Si—$(R^n)(R^m)$—, wherein $R^m$ and $R^n$ are independently selected from $C_1$-$C_4$ alkyl, $C_6$ aryl, or H and wherein h ranges from 1 to 2000. In some embodiments, h ranges from 1 to 1500. In other embodiments, h ranges from 1 to 1000. In yet other embodiments, h ranges from 1 to 750. In further embodiments, h ranges from 1 to 500. In yet further embodiments, h ranges from 1 to 250.

In some embodiments, $R^3$ is 2,2-dimethyl propane or sec-butane. In other embodiments, $R^3$ is derived from 2,2-diphenyl propane. In some embodiments, $R^3$ is derived from poly(dimethylsiloxane) having a molecular weight ranging from about 70 to about 100,000; or derived from poly(diarylsiloxane) having a molecular weight ranging from about 190 to about 100,000.

In some embodiments, $R^5$ is —C(O)—, —CH$_2$— or —C(H)(Ph)-. In some embodiments, $R^5$ is —CH$_2$—. In some embodiments, $R^5$ is —C(O)—.

In some embodiments, $R^6$ is H. In other embodiments, $R^6$ is a $C_1$-$C_8$ straight chain or branched alkyl group. In other embodiments, $R^6$ is a $C_1$-$C_6$ straight chain or branched alkyl group. In yet other embodiments, $R^6$ is a $C_1$-$C_4$ straight chain or branched alkyl group. In further embodiments, $R^6$ is methyl.

In some embodiments, $R^{13}$ is —(CH$_2$)$_u$—, where u is 0 or an integer ranging from 1 to 5000; or a group —(C$_6$H$_4$—O—(C$_6$H$_4$—O)$_w$—C$_6$H$_4$—, where w is 0 or an integer ranging from 1 to 40.

Non-limiting examples of the compounds of Formula (IIIA) include the following:

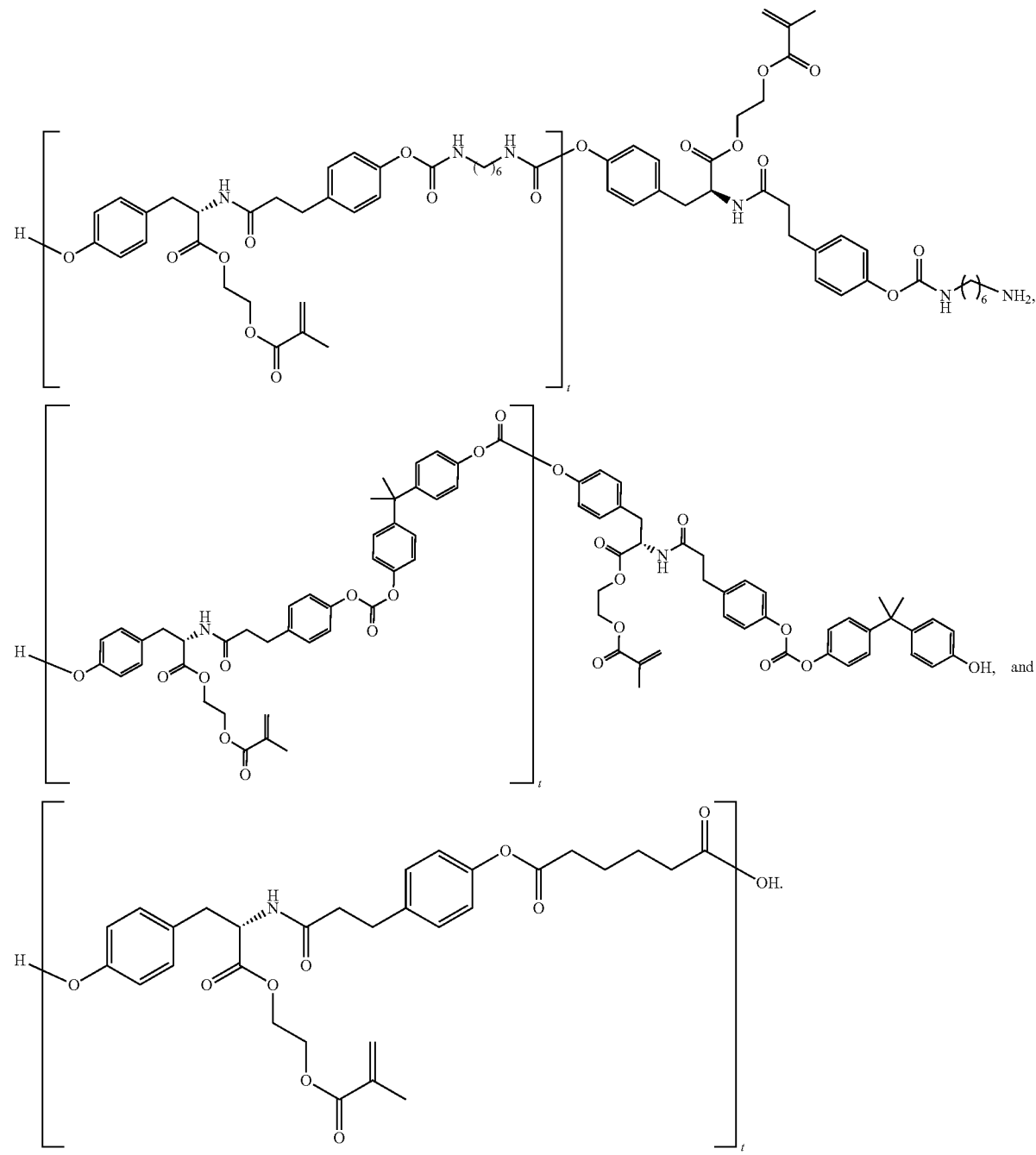

In some embodiments, the compounds of the present disclosure have the structure of Formula (IIIB):

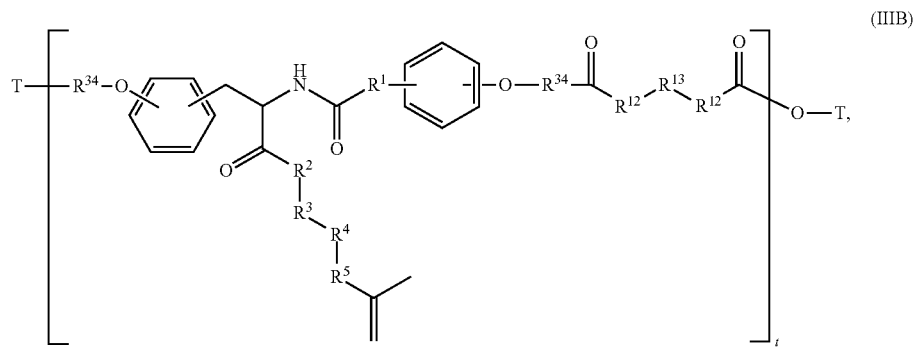

wherein
$R^1$ is —CH=CH— or (—CH$_2$-)$_R$;
$R^2$ is —O—, —NR$^s$—, where $R^s$ is H or a $C_1$-$C_4$ alkyl group, or —S—;
$R^3$ is a straight chain or branched alkyl group having up to 10 carbon atoms, a straight chain or branched alkylaryl group having up to 20 carbon atoms, or siloxane group;
$R^4$ is —O—, —NR$^s$—, where $R^s$ is H or a $C_1$-$C_4$ alkyl group, —S—, —CH$_2$—;
$R^5$ is C=O, —CH$_2$—, a benzyl group, or a substituted benzyl group;
each $R^{12}$ is independently a bond, —CH$_2$—, —O—, or —NR$^s$—, where $R^s$ is H or a $C_1$-$C_4$ alkyl group;
$R^{13}$ is a substituted or unsubstituted aliphatic group having between 1 and 5000 carbon atoms and optionally including one or more heteroatoms selected from O, N, or S; —(CH$_2$—O—(CH$_2$—O)$_v$—CH$_2$)—; or a substituted or unsubstituted aromatic group having between 6 and 280 carbon atoms;
each $R^{34}$ is independently a bond, 4-hydroxybenzene, 3-iodo-4-hydroxybenzene, or 3,5-diiodo-4-hydroxybenzene;
n is 0 or an integer ranging from 1 to 8;
t is an integer ranging from 1 to 1000; and
v is 0 or an integer ranging from 1 to 5000.
In some embodiments, $R^1$ is —CH$_2$CH$_2$CH$_2$CH$_2$—. In other embodiments, $R^1$ is —CH$_2$CH$_2$CH$_2$—. In yet other embodiments, $R^1$ is —CH$_2$CH$_2$—. In further embodiments, $R^1$ is —CH$_2$—.
In some embodiments, $R^3$ is a $C_1$-$C_8$ straight chain or branched alkyl group. In other embodiments, $R^3$ is a $C_1$-$C_6$ straight chain or branched alkyl group. In yet other embodiments, $R^3$ is a $C_1$-$C_4$ straight chain or branched alkyl group.
In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 16 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 12 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 9 carbon atoms.
In some embodiments, the siloxane group has the structure of —(R''')(R'')—Si—O—Si—(R'')(R''')—, or —(R''')(R'')—Si—[O—Si—(R'')(R''')]$_h$—O— Si—(R'')(R''')—, wherein R''' and R'' are independently selected from $C_1$-$C_4$ alkyl, $C_6$ aryl, or H and herein h ranges from 1 to 2000. In some embodiments, h ranges from 1 to 1500. In other embodiments, h ranges from 1 to 1000. In yet other embodiments, h ranges from 1 to 750. In further embodiments, h ranges from 1 to 500. In yet further embodiments, h ranges from 1 to 250.
In some embodiments, $R^3$ is 2,2-dimethyl propane or sec-butane. In other embodiments, $R^3$ is derived from 2,2-diphenyl propane. In some embodiments, $R^3$ is derived from poly(dimethylsiloxane) having a molecular weight ranging from about 70 to about 100,000; or derived from poly(diarylsiloxane) having a molecular weight ranging from about 190 to about 100,000. In some embodiments, $R^6$ is H. In other embodiments, $R^6$ is a $C_1$-$C_8$ straight chain or branched alkyl group. In other embodiments, $R^6$ is a $C_1$-$C_6$ straight chain or branched alkyl group. In yet other embodiments, $R^6$ is a $C_1$-$C_4$ straight chain or branched alkyl group. In further embodiments, $R^6$ is methyl.
In some embodiments, $R^5$ is —C(O)—, —CH$_2$— or —C(H)(Ph)-. In some embodiments, $R^5$ is —CH$_2$—. In some embodiments, $R^5$ is —C(O)—.
In some embodiments, $R^{13}$ is —(CH$_2$)$_u$—, where u is 0 or an integer ranging from 1 to 5000; or a group —(C$_6$H$_4$—O—(C$_6$H$_4$—O)$_w$—C$_6$H$_4$—, where w is 0 or an integer ranging from 1 to 40.
In some embodiments, the compounds of the present disclosure have the structure of Formula (IIIC):

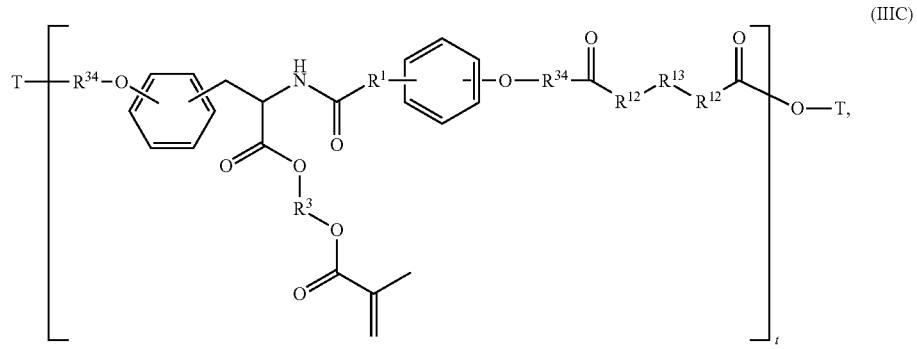

(IIIC)

wherein
$R^1$ is —CH=CH— or (—CH$_2$-)$_n$;
$R^3$ is a straight chain or branched alkyl group having up to 10 carbon atoms, a straight chain or branched alkylaryl group having up to 20 carbon atoms, or siloxane group;
each $R^{12}$ is independently a bond, —CH$_2$—, —O—, or —NR$^{s}$-, where $R^s$ is H or a $C_1$-$C_4$ alkyl group;
$R^{13}$ is a substituted or unsubstituted aliphatic group having between 1 and 5000 carbon atoms and optionally including one or more heteroatoms selected from O, N, or S; —(CH$_2$—O—(CH$_2$—O)$_v$—CH$_2$)—; or a substituted or unsubstituted aromatic group having between 6 and 280 carbon atoms;

each $R^{34}$ is independently a bond, 4-hydroxybenzene, 3-iodo-4-hydroxybenzene, or 3,5-diiodo-4-hydroxybenzene;

n is 0 or an integer ranging from 1 to 8;

t is an integer ranging from 1 to 1000; and v is 0 or an integer ranging from 1 to 5000.

In some embodiments, each $R^{34}$ is a bond.

In some embodiments, compounds of the present disclosure have the structure of any of Formulas (IIID), (IIIE), (IIIF), or (IIIG):

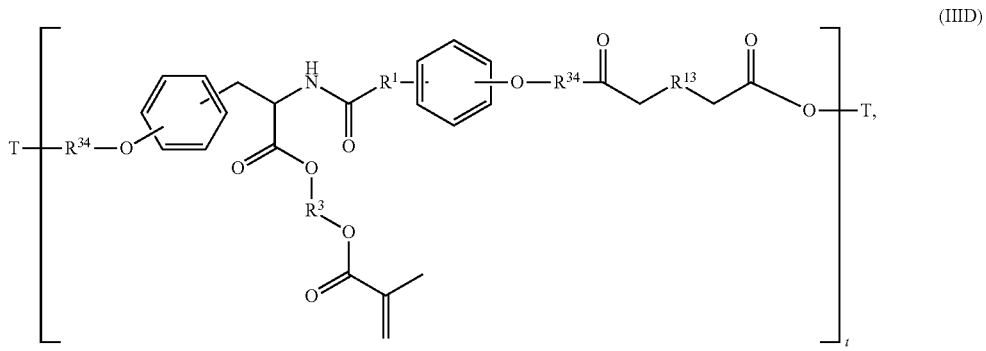

(IIID)

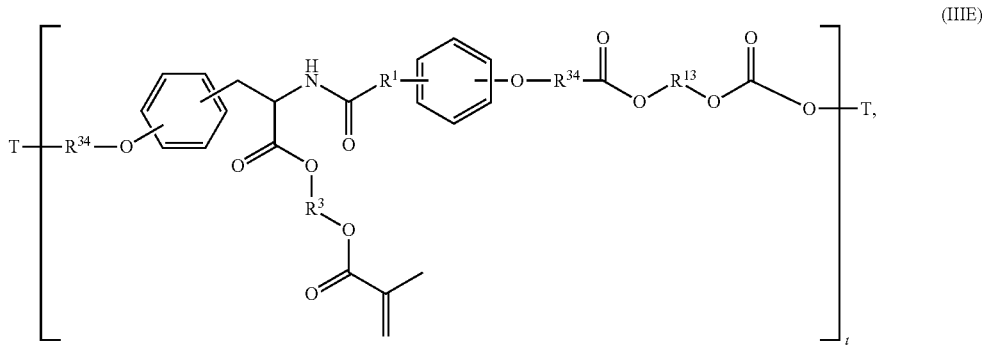

(IIIE)

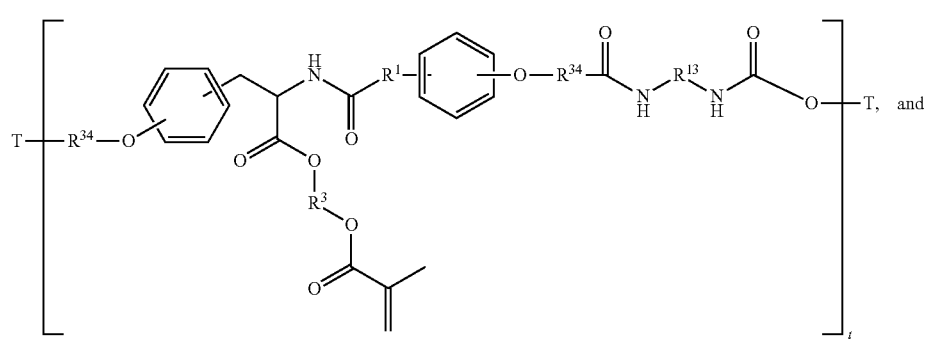
(IIIF)

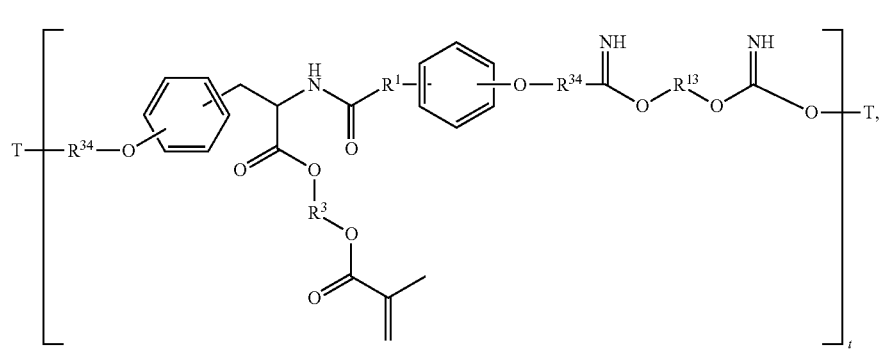
(IIIG)

wherein $R^1$ is —CH=CH— or (—CH$_2$—)$_n$;

$R^3$ is a straight chain or branched alkyl group having up to 10 carbon atoms, a straight chain or branched alkylaryl group having up to 20 carbon atoms, or siloxane group;

$R^{13}$ is a substituted or unsubstituted aliphatic group having between 1 and 5000 carbon atoms and optionally including one or more heteroatoms selected from O, N, or S; —(CH$_2$—O—(CH$_2$—O)$_v$—CH$_2$)—; or a substituted or unsubstituted aromatic group having between 6 and 280 carbon atoms;

each $R^{34}$ is independently a bond, 4-hydroxybenzene, 3-iodo-4-hydroxybenzene, or 3,5-diiodo-4-hydroxybenzene;

n is 0 or an integer ranging from 1 to 8;

t is an integer ranging from 1 to 1000; and v is 0 or an integer ranging from 1 to 5000.

In some embodiments, each $R^{34}$ is a bond.

In some embodiments, t is an integer ranging from 1 to 50. In other embodiments, t is an integer ranging from 1 to 20.

In some embodiments, v is an integer ranging from 1 to 1000. In other embodiments, t is an integer ranging from 1 to 500. In other embodiments, t is an integer ranging from 1 to 200. In other embodiments, t is an integer ranging from 1 to 100. In other embodiments, t is an integer ranging from 1 to 50.

Reaction Products of the Compounds of Formulas (IA), (IB), (IC), (ID), and (IE) with Cyanate Esters In some embodiments, the compounds of any of Formulas (IA)-(IE) may be reacted with a dicyanate ester to form the compounds of any of Formulas (IVA) to (IVD).

Suitable dicyanate esters for reaction include, but are not limited to, 2,2-bis(4-Cyanatophenyl) isopropylidene (available from Lonza under tradename Primaset BADCY), Bis-(4-Cyanato-3,5-dimethylpheny)methane, cyanated phenoldicyclopentadine, Bis-(4-Cyanatophenyl)thioether, Bis(4-Cyanatophenyl) ether, 1,3-bis(4-Cyanatophenyl-1(1-methylidene) benzene, Resorcinol dicyanate, fused ring cyanate monomers such as naphthalene and anthraquinone, fluoroaliphatic dicyanates, Bisphenol F Cyanate ester (p-Cyanato[(p-cyanatophenyl)methyl]benzene), Primaset PT resin (Oligo(3-methylene-1,5-phenylenecyanate), Primaset LECY (p-Cyanato[1-(p-cyanatophenyl)ethyl]benzene) and mixtures thereof.

In some embodiments, the compounds of the present disclosure have the structure of Formula (IVA):

(IVA)

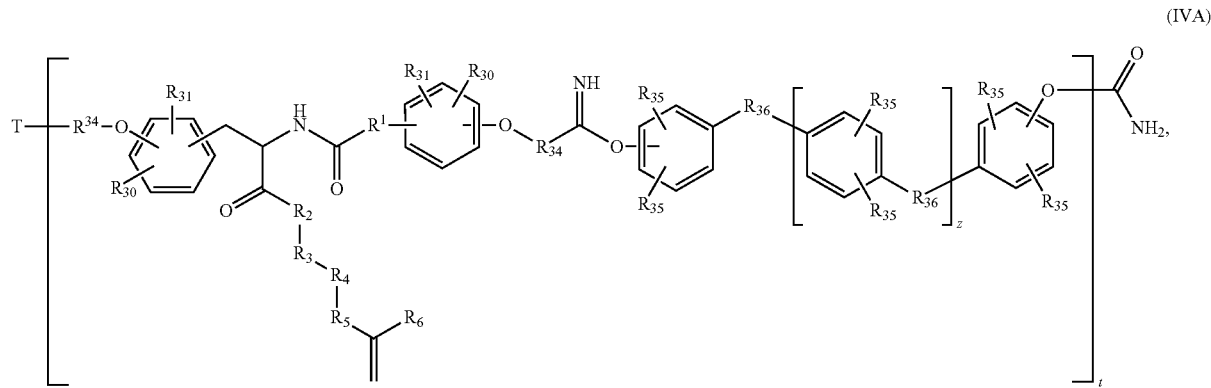

wherein
$R^1$ is —CH=CH— or (—$CH_2$-)$_n$;
$R^2$ is —O—, —$NR^s$—, where $R^s$ is H or a $C_1$-$C_4$ alkyl group, or —S—;
$R^3$ is a straight chain or branched alkyl group having up to 10 carbon atoms, a straight chain or branched alkylaryl group having up to 20 carbon atoms, or siloxane group;
$R^4$ is —O—, —$NR^s$—, where $R^s$ is H or a $C_1$-$C_4$ alkyl group, —S—, —$CH_2$—;
$R^5$ is C=O, —$CH_2$—, a benzyl group, or a substituted benzyl group;
$R^6$ is H or a straight chain or branched alkyl group having up to 18 carbons atoms;
each of $R^{30}$ and $R^{31}$ is independently selected from I or H;
each $R^{34}$ is independently a bond, 4-hydroxybenzene, 3-iodo-4-hydroxybenzene, or 3,5-diiodo-4-hydroxybenzene;
each $R^{35}$ is independently an H, an aliphatic group having between 1 and 9 carbon atoms, an aromatic group having between 6 and 10 carbon atoms, an —OH group, or halogen;
each $R^{36}$ is $R^{14}$, a substituted or unsubstituted aromatic group having between 6 and 10 carbon atoms, $CH_2$, $CH(CH_3)$, $C(CH_3)_2$, $SO_2$, O, or S;
and where $R^{14}$ is —$CH(CH_3)$—, —$CH_2$—, —C($CH_3$)$_2$—, dicyclopentadiene or a functionalized dicyclopentadiene;
T is H;
t is an integer ranging from 1 to 1000;
n is 0 or an integer ranging from 1 to 8; and
z is 0 or an integer ranging from 1 to 100.

In some embodiments, $R^1$ is —CH=CH— or (—$CH_2$-)$_n$, wherein n ranges from 1 to 8. In some embodiments, n ranges from to 1 to 4. In other embodiments, $R^1$ is —$CH_2CH_2CH_2CH_2$—. In other embodiments, $R^1$ is —$CH_2CH_2CH_2$—. In yet other embodiments, $R^1$ is —$CH_2CH_2$—. In further embodiments, $R^1$ is —$CH_2$—.

In some embodiments, $R^3$ is a $C_1$-$C_5$ straight chain or branched alkyl group. In other embodiments, $R^3$ is a $C_1$-$C_6$ straight chain or branched alkyl group. In yet other embodiments, $R^3$ is a $C_1$-$C_4$ straight chain or branched alkyl group.

In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 16 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 12 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 9 carbon atoms.

In some embodiments, the siloxane group has the structure of —($R'''$)($R''$)—Si—O—Si—($R''$)($R'''$)—, or —($R'''$)($R''$)—Si—[O—Si—($R''$)($R'''$)]$_h$—O— Si—($R''$)($R'''$)—, wherein $R'''$ and $R''$ are independently selected from $C_1$-$C_4$ alkyl, $C_6$ aryl, or H and herein h ranges from 1 to 2000. In some embodiments, h ranges from 1 to 1500. In other embodiments, h ranges from 1 to 1000. In yet other embodiments, h ranges from 1 to 750. In further embodiments, h ranges from 1 to 500. In yet further embodiments, h ranges from 1 to 250.

In some embodiments, $R^3$ is 2,2-dimethyl propane or sec-butane. In other embodiments, $R^3$ is derived from 2,2-diphenyl propane. In some embodiments, $R^3$ is derived from poly(dimethylsiloxane) having a molecular weight ranging from about 70 to about 100,000; or derived from poly (diarylsiloxane) having a molecular weight ranging from about 190 to about 100,000.

In some embodiments, $R^5$ is —C(O)—, —$CH_2$— or —C(H)(Ph)-. In some embodiments, $R^5$ is —$CH_2$—. In some embodiments, $R^5$ is —C(O)—.

In some embodiments, $R^6$ is H. In other embodiments, $R^6$ is a $C_1$-$C_8$ straight chain or branched alkyl group. In other embodiments, $R^6$ is a $C_1$-$C_6$ straight chain or branched alkyl group. In yet other embodiments, $R^6$ is a $C_1$-$C_4$ straight chain or branched alkyl group. In further embodiments, $R^6$ is methyl.

In some embodiments, $R^{13}$ is —($CH_2$)$_u$—, where u is 0 or an integer ranging from 1 to 5000; or a group —($C_6H_4$—O—($C_6H_4$—O)$_w$—$C_6H_4$—, where w is 0 or an integer ranging from 1 to 40.

In some embodiments, $R^{35}$ is OH and $R^{36}$ is —$CH_2$—, —$CH(CH_3)$— or —$C(CH_3)_2$.

An example of a compound of Formula (IVA) is set forth below:

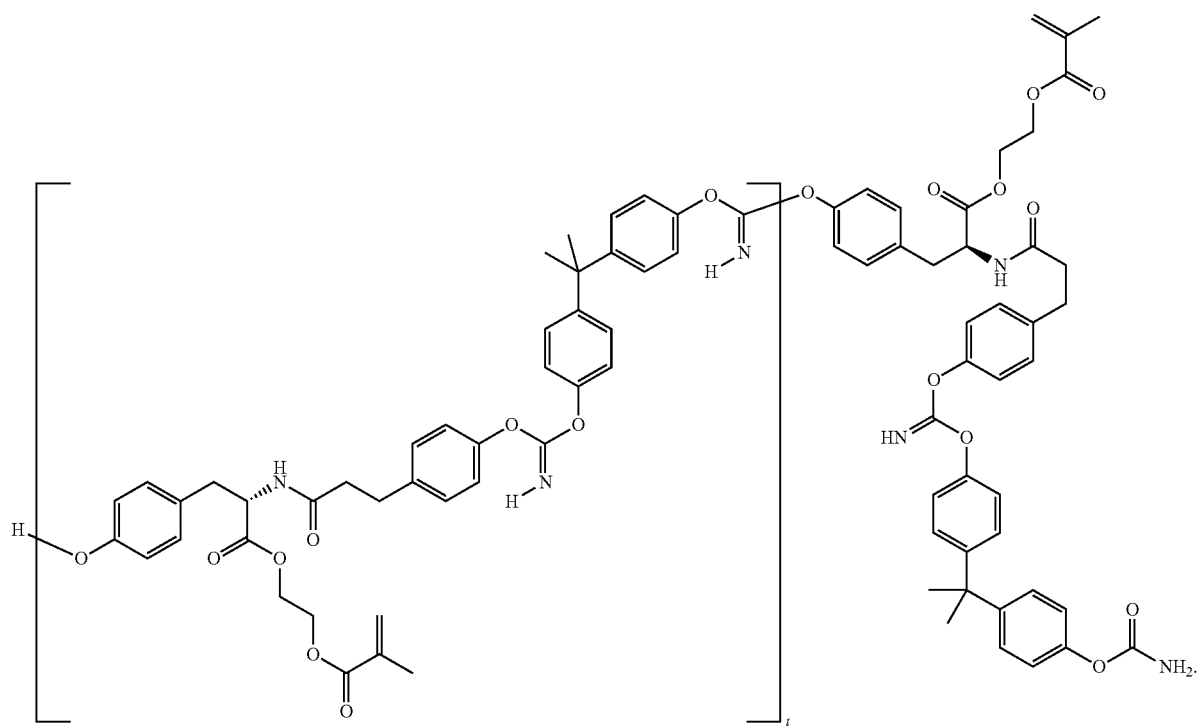

In some embodiments, the compounds of the present disclosure have the structure of Formula (IVB):

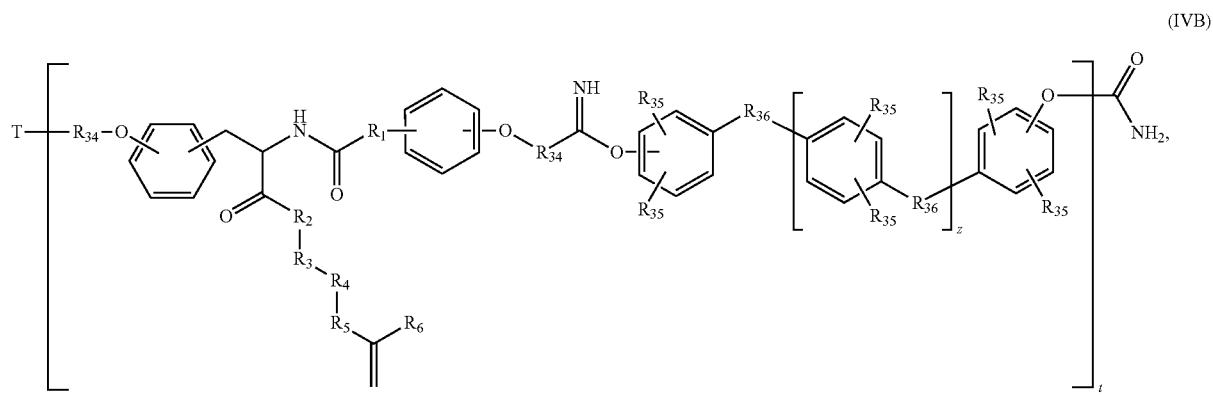

(IVB)

wherein $R^1$ is —CH=CH— or (—CH$_2$-)$_n$;

$R^2$ is —O—, —NR$^s$—, where $R^s$ is H or a $C_1$-$C_4$ alkyl group, or —S—;

$R^3$ is a straight chain or branched alkyl group having up to 10 carbon atoms, a straight chain or branched alkylaryl group having up to 20 carbon atoms, or siloxane group;

$R^4$ is —O—, —NR$^s$—, where $R^s$ is H or a C1-$C_4$ alkyl group, —S—, —CH$_2$—;

$R^5$ is C=O, —CH$_2$—, a benzyl group, or a substituted benzyl group;

$R^6$ is H or a straight chain or branched alkyl group having up to 18 carbons atoms;

each $R^{34}$ is independently a bond, 4-hydroxybenzene, 3-iodo-4-hydroxybenzene, or 3,5-diiodo-4-hydroxybenzene;

each $R^{35}$ is independently an H, an aliphatic group having between 1 and 9 carbon atoms, an aromatic group having between 6 and 10 carbon atoms, an —OH group, or halogen;

each $R^{36}$ is $R^{14}$, a substituted or unsubstituted aromatic group having between 6 and 10 carbon atoms, CH$_2$, CH(CH$_3$), C(CH$_3$)$_2$, SO$_2$, O, or S;

and where $R^{14}$ is —CH(CH$_3$)—, —CH$_2$—, —C(CH$_3$)$_2$—, dicyclopentadiene or a functionalized dicyclopentadiene;

T is H;

t is an integer ranging from 1 to 1000;

n is 0 or an integer ranging from 1 to 8; and z is 0 or an integer ranging from 1 to 100.

In some embodiments, the compounds of the present disclosure have the structure of any of Formulas (IVC) and (IVD):

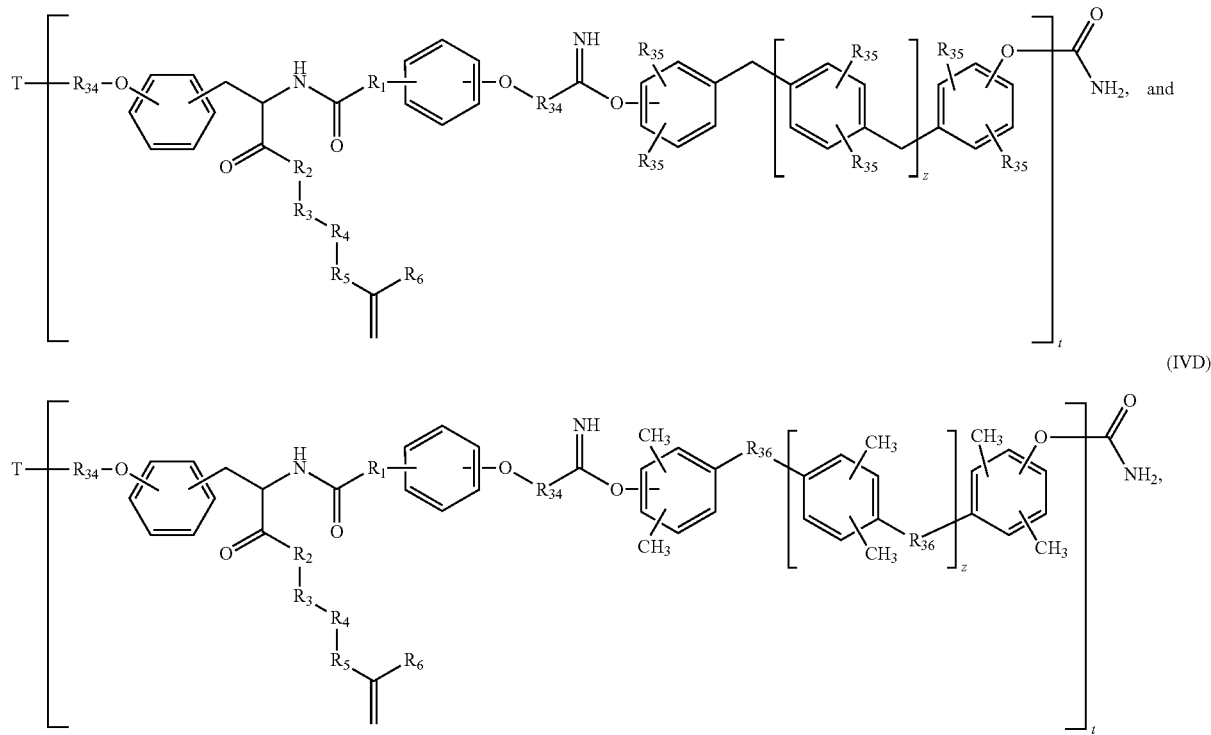

wherein
R$^1$ is —CH=CH— or (—CH$_2$-)$_n$;
R$^2$ is —O—, —NR$^s$—, where R$^s$ is H or a C$_1$-C$_4$ alkyl group, or —S—;
R$^3$ is a straight chain or branched alkyl group having up to 10 carbon atoms, a straight chain or branched alkylaryl group having up to 20 carbon atoms, or siloxane group;
R$^4$ is —O—, —NR$^s$—, where R$^s$ is H or a C1-C$_4$ alkyl group, —S—, —CH$_2$—;
R$^5$ is C=O, —CH$_2$—, a benzyl group, or a substituted benzyl group;
R$^6$ is H or a straight chain or branched alkyl group having up to 18 carbons atoms;
each R$^{34}$ is independently a bond, 4-hydroxybenzene, 3-iodo-4-hydroxybenzene, or 3,5-diiodo-4-hydroxybenzene;
each R$^{35}$ is independently an H, an aliphatic group having between 1 and 9 carbon atoms, an aromatic group having between 6 and 10 carbon atoms, an —OH group, or halogen;
each R$^{36}$ is R$^{14}$, a substituted or unsubstituted aromatic group having between 6 and 10 carbon atoms, CH$_2$, CH(CH$_3$), C(CH$_3$)$_2$, SO$_2$, O, or S;
and where R$^{14}$ is —CH(CH$_3$)—, —CH$_2$—, —C(CH$_3$)$_2$—, dicyclopentadiene or a functionalized dicyclopentadiene;
T is H;
t is an integer ranging from 1 to 1000;
n is 0 or an integer ranging from 1 to 8; and
z is 0 or an integer ranging from 1 to 100.
In some embodiments, R$^3$ is 2,2-dimethyl propane or sec-butane. In other embodiments, R$^3$ is derived from 2,2-diphenyl propane. In some embodiments, R$^3$ is derived from poly(dimethylsiloxane) having a molecular weight ranging from about 70 to about 100,000; or derived from poly (diarylsiloxane) having a molecular weight ranging from about 190 to about 100,000. In some embodiments, R$^6$ is H. In other embodiments, R$^6$ is a C$_1$-C$_8$ straight chain or branched alkyl group. In other embodiments, R$^6$ is a C$_1$-C$_6$ straight chain or branched alkyl group. In yet other embodiments, R$^6$ is a C$_1$-C$_4$ straight chain or branched alkyl group. In further embodiments, R$^6$ is methyl.
In some embodiments, R$^5$ is —C(O)—, —CH$_2$— or —C(H)(Ph)-. In some embodiments, R$^5$ is —CH$_2$—. In some embodiments, R$^5$ is —C(O)—.
In some embodiments, at least one of R$^2$, R$^3$ and R$^5$ is O.
In some embodiments, at least two of R$^2$, R$^3$ and R$^5$ is O. In some embodiments, each of R$^2$, R$^3$ and R$^5$ is O. In some embodiments, each of R$^2$, R$^3$ and R$^5$ is O and R$^6$ is —CH$_3$.

Reaction Products of the Compounds of Formulas (IIA), (IIB), (IIC), (IID), (IIE), and (IIF) with a Diacid or a Diisocyanate In some embodiments, the compounds of Formulas (IIA), (IIB), (IIC), (IID), (IIE), and (IIF) are reacted with a diacid or a diisocyanate to provide the compounds of any of Formulas and (VA) to (VE). Suitable diacids for reaction with the compounds of Formulas (IA)-(IE) and (IIA)-(IIF) include, but are not limited to, maleic acid, fumaric acid, malic acid, oxalic acid, malonic acid, succinic acid, adipic acid, butaneioic acid, decanedioic acid, itaconic acid, citric acid, acid, pimelic acid, suberic acid, sebacic acid, phthalic acid, terephthalic acid, isophthalic acid, and malonic acid.
Suitable diisocyanates for reaction with the compounds of Formulas (IA)-(IE) and (IIA)-(IIF) include, but are not limited to, toluene diisocyanate (TDI), methylenediphenyl isocyanate (MDI), isophorone diisocyanate (IPDI), methylene dicyclohexyl diisocyanate (commonly referred to as hydrogenated MDI or HMDI), and hexamethylene diisocyanate (HDI).

In some embodiments, the compounds of the present disclosure have the structure of Formula (VA):

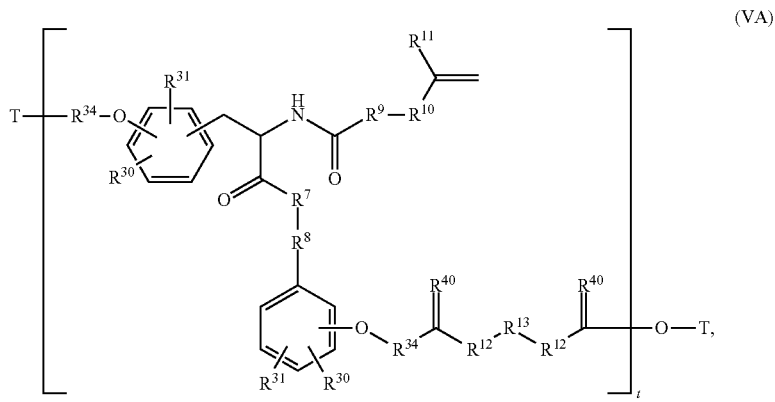

(VA)

wherein
$R^7$ is —O—, —NR$^s$—, where $R^s$ is H or a $C_1$-$C_4$ alkyl group, —S—, —CH$_2$—;
$R^8$ is a saturated or unsaturated, substituted or unsubstituted, straight chain or branched alkyl group having between 1 and 20 carbon atoms;
$R^9$ is a bond, —O—, —(CH$_2$)$_m$—;
$R^{10}$ is a bond; a straight chain or branched alkyl group having up to 10 carbon atoms; a straight chain or branched alkylaryl group having up to 20 carbon atoms; —(CR$^a$R$^b$—CR$^a$R$^b$O)$_o$—, —(CR$^a$R$^b$—CR$^a$R$^b$—O)$_o$—C(O)— wherein R$^a$ and R$^b$ are independently H or a $C_1$-$C_4$ alkyl group; or a siloxane group;
$R^{11}$ is H or a straight chain or branched alkyl group having up to 18 carbons;
each $R^{12}$ is independently a bond, —CH$_2$—, —O—, or —NR$^s$—, where $R^s$ is H or a $C_1$-$C_4$ alkyl group;
$R^{13}$ is a substituted or unsubstituted aliphatic group having between 1 and 5000 carbon atoms and optionally including one or more heteroatoms selected from O, N, or S; —(CH$_2$—O—(CH$_2$—O)$_v$—CH$_2$)—; or a substituted or unsubstituted aromatic group having between 6 and 280 carbon atoms;
each of $R^{30}$ and $R^{31}$ is independently selected from I or H;
each $R^{34}$ is independently a bond, 4-hydroxybenzene, 3-iodo-4-hydroxybenzene, or 3,5-diiodo-4-hydroxybenzene;
each $R^{40}$ is independently O or NH;
T is H;
m is 0 or an integer ranging from 1 to 8;
o is an integer ranging from 1 to 500; and
t is an integer ranging from 1 to 1000.
In some embodiments, o is an integer ranging from 1 to 400. In other embodiments, o is an integer ranging from 1 to 300. In yet other embodiments, o is an integer ranging from 1 to 200. In further embodiments, o is an integer ranging from 1 to 100. In yet further embodiments, o is an integer ranging from 1 to 50.

In some embodiments, $R^8$ is —CH=CH— or (—CH$_2$-)$_n$, wherein n ranges from 1 to 20. In some embodiments, n ranges from to 1 to 16. In other embodiments, n ranges from to 1 to 16. In yet other embodiments, n ranges from to 1 to 12. In further embodiments, n ranges from to 1 to 8. In even further embodiments, n ranges from to 1 to 6. In some embodiments, $R^8$ is —CH$_2$CH$_2$CH$_2$CH$_2$—. In other embodiments, $R^8$ is —CH$_2$CH$_2$CH$_2$—. In yet other embodiments, $R^8$ is —CH$_2$CH$_2$—. In further embodiments, $R^8$ is —CH$_2$—.

In some embodiments, $R^{10}$ is —(CH$_2$)—$_p$, where p ranges from 1 to 12. In some embodiments, p ranges from 1 to 6. In other embodiments, p ranges from 1 to 4. In yet other embodiments, p is 1 or 2.

In some embodiments, $R^{10}$ is —(CH$_2$CH$_2$O)$_o$—, —(CH$_2$CH$_2$O)$_o$C(O)—, where o ranges from 1 to 250. In some embodiments, $R^{10}$ is —(CH$_2$CH$_2$O)$_o$—, —(CH$_2$CH$_2$O)$_o$C(O)—, where o ranges from 1 to 100. In some embodiments, $R^{10}$ is —(CH$_2$CH$_2$O)$_o$—, —(CH$_2$CH$_2$O)$_o$C(O)—, where o ranges from 1 to 50. In some embodiments, $R^{10}$ is —(CH$_2$CH$_2$O)$_o$—, —(CH$_2$CH$_2$O)$_o$C(O)—, where o ranges from 1 to 10. In other embodiments, $R^{10}$ is —(CH$_2$CH$_2$O)$_o$—, —(CH$_2$CH$_2$O)$_o$C(O)—, where o ranges from 1 to 6.

In some embodiments, $R^{11}$ is H. In other embodiments, $R^{11}$ is methyl.

Examples of the compounds of Formula (VA) include the following:

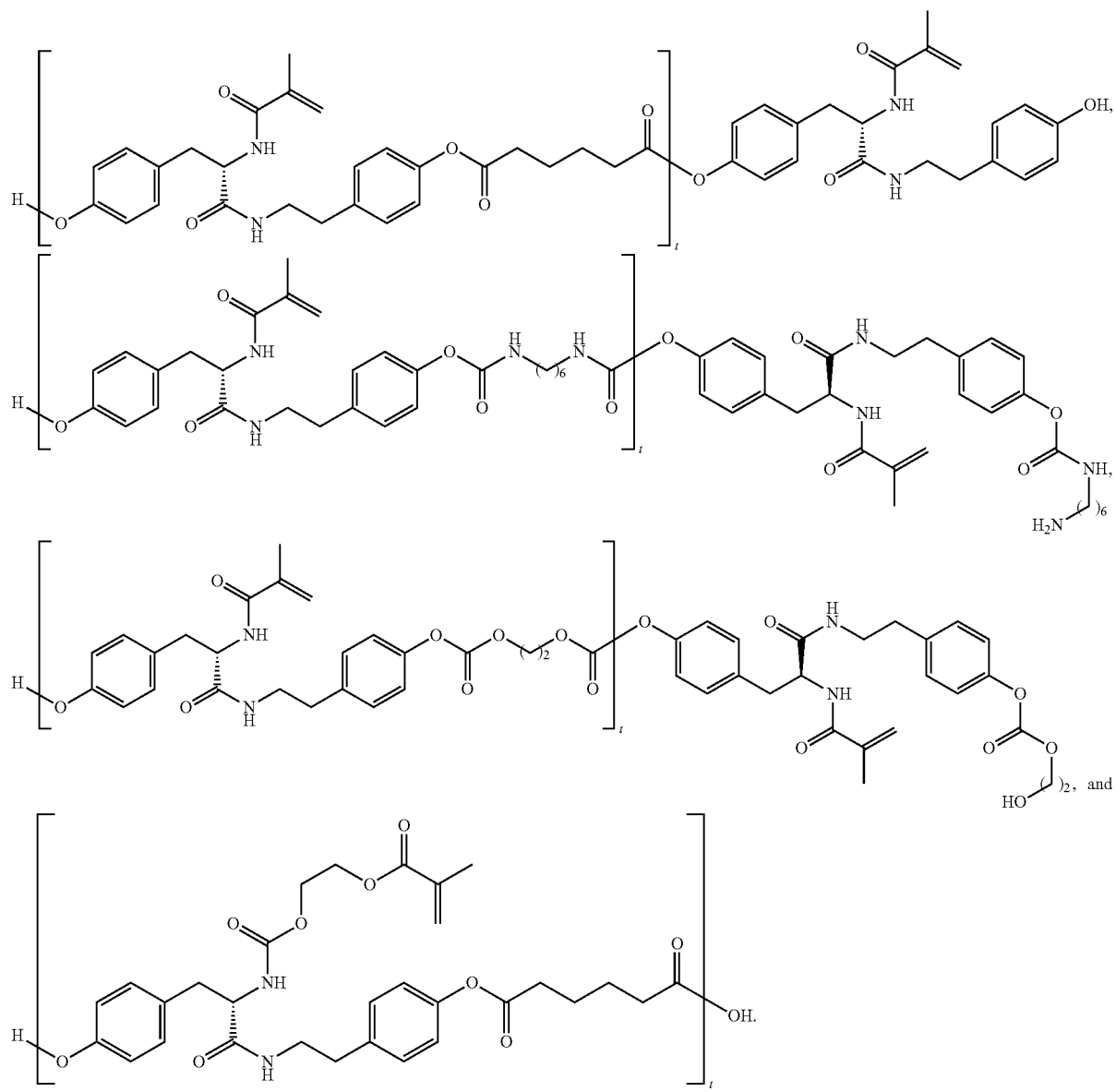
In some embodiments, the compounds of the present disclosure have the structure of Formula (VB):
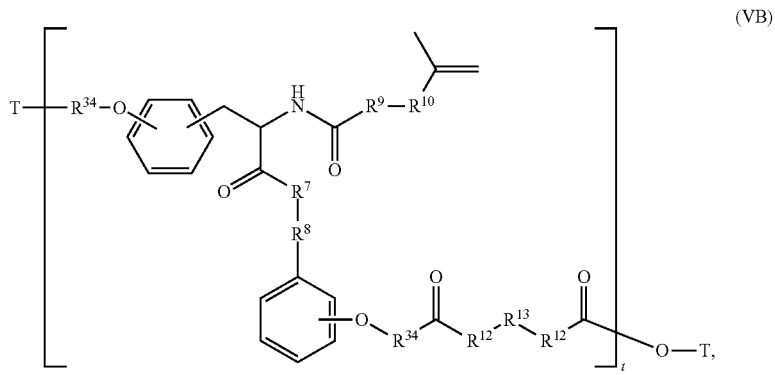

wherein

R$^7$ is —O—, —NR$^s$—, where R$^s$ is H or a C$_1$-C$_4$ alkyl group, —S—, —CH$_2$—;

R$^8$ is a saturated or unsaturated, substituted or unsubstituted, straight chain or branched alkyl group having between 1 and 20 carbon atoms;

R$^9$ is a bond, —O—, —(CH$_2$)$_m$—;

R$^{10}$ is a bond; a straight chain or branched alkyl group having up to 10 carbon atoms; a straight chain or branched alkylaryl group having up to 20 carbon atoms; —(CR$^a$R$^b$—CR$^a$R$^b$O)$_o$—, —(CR$^a$R$^b$—CR$^a$R$^b$—O)$_o$—C(O)— wherein R$^a$ and R$^b$ are independently H or a C$_1$-C$_4$ alkyl group; or a siloxane group;

each R$^{12}$ is independently a bond, —CH$_2$—, —O—, or —NR$^s$—, where R$^s$ is H or a C$_1$-C$_4$ alkyl group;

R$^{13}$ is a substituted or unsubstituted aliphatic group having between 1 and 5000 carbon atoms and optionally including one or more heteroatoms selected from O, N, or S; —(CH$_2$—O—(CH$_2$—O)$_v$—CH$_2$)—; or a substituted or unsubstituted aromatic group having between 6 and 280 carbon atoms;

each R$^{34}$ is independently a bond, 4-hydroxybenzene, 3-iodo-4-hydroxybenzene, or 3,5-diiodo-4-hydroxybenzene;

T is H;

m is 0 or an integer ranging from 1 to 8;

o is an integer ranging from 1 to 500; and t is an integer ranging from 1 to 1000.

In some embodiments, each R$^{34}$ is independently a bond.

In some embodiments, R$^8$ is —(CH$_2$)$_n$—. In some embodiments, R$^8$ is —(CH$_2$)$_n$—, where n is an integer ranging from 1 to 4. In other embodiments, R$^8$ is —(CH$_2$)$_n$—, where n is an integer ranging from 1 to 2.

In some embodiments, both R$^9$ and R$^{10}$ are bonds.

In some embodiments, R$^7$ is —NH—, and R$^8$ is —(CH$_2$)$_n$—. In some embodiments, R$^7$ is —NH—, and R$^8$ is —(CH$_2$)$_n$—, where n is an integer ranging from 1 to 4. In other embodiments, R$^7$ is —NH—, and R$^8$ is —(CH$_2$)$_n$, where n is an integer ranging from 1 to 2.

In some embodiments, R$^7$ is —NH—, R$^8$ is —(CH$_2$)$_n$—, and at least one of R$^9$ or R$^{10}$ is a bond. In some embodiments, R$^7$ is —NH—, R$^8$ is —(CH$_2$)$_n$—, where n is an integer ranging from 1 to 4, and at least one of R$^9$ or R$^{10}$ is a bond. In other embodiments, R$^7$ is —NH—, R$^8$ is —(CH$_2$)$_n$—, where n is an integer ranging from 1 to 2, and at least one of R$^9$ or R$^{10}$ is a bond. In other embodiments, R$^7$ is —NH—, R$^8$ is —(CH$_2$)$_n$—, where n is an integer ranging from 1 to 4, R$^9$ and R$^{10}$ are both bonds. In other embodiments, R$^7$ is —NH—, R$^8$ is —(CH$_2$)$_n$—, where n is an integer ranging from 1 to 2, R$^9$ and R$^{10}$ are both bonds.

In some embodiments, the compounds of the present disclosure have the structure of Formulas (VC), (VD), and (VE):

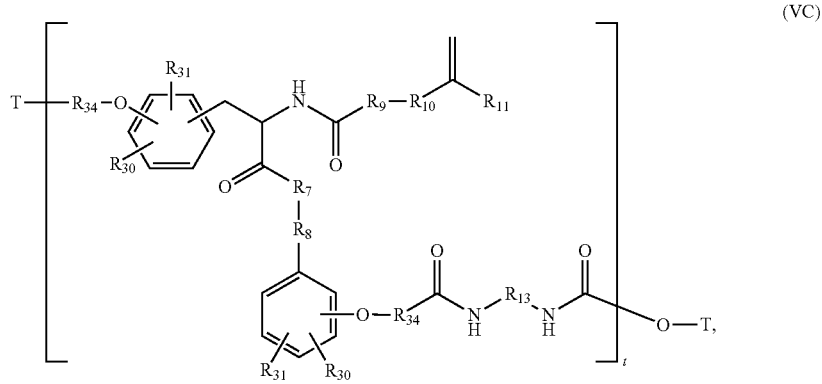

(VC)

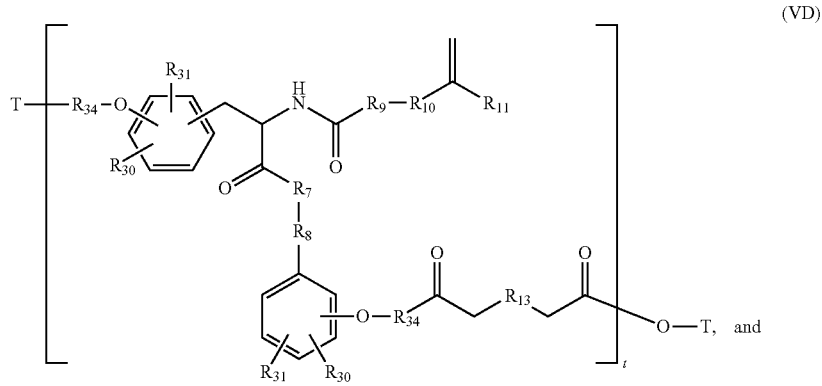

(VD) and

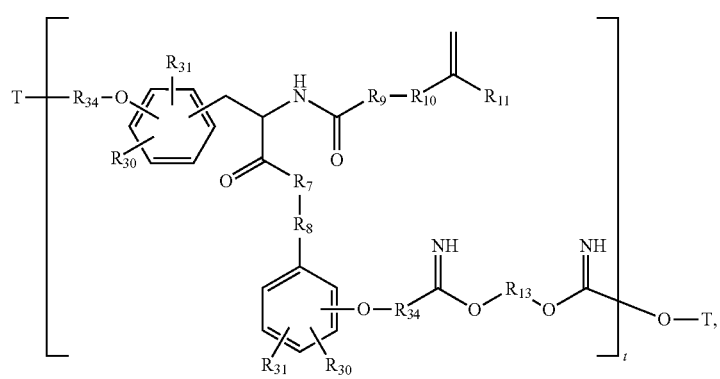

(VE)

wherein $R^7$ is —O—, —$NR^s$—, where $R^s$ is H or a $C_1$-$C_4$ alkyl group, —S—, —$CH_2$—;

$R^8$ is a saturated or unsaturated, substituted or unsubstituted, straight chain or branched alkyl group having between 1 and 20 carbon atoms;

$R^9$ is a bond, —O—, —$(CH_2)_m$—;

$R^{10}$ is a bond; a straight chain or branched alkyl group having up to 10 carbon atoms; a straight chain or branched alkylaryl group having up to 20 carbon atoms; —($CR^aR^b$—$CR^aR^bO$)$_o$—, —($CR^aR^b$—$CR^aR^b$—O)$_o$—C(O)— wherein $R^a$ and $R^b$ are independently H or a $C_1$-$C_4$ alkyl group; or a siloxane group;

$R^{13}$ is a substituted or unsubstituted aliphatic group having between 1 and 5000 carbon atoms and optionally including one or more heteroatoms selected from O, N, or S; —($CH_2$—O—($CH_2$—O)$_v$—$CH_2$)—; or a substituted or unsubstituted aromatic group having between 6 and 280 carbon atoms;

each $R^{34}$ is independently a bond, 4-hydroxybenzene, 3-iodo-4-hydroxybenzene, or 3,5-diiodo-4-hydroxybenzene;

T is H;

m is 0 or an integer ranging from 1 to 8;

o is an integer ranging from 1 to 500; and t is an integer ranging from 1 to 1000.

In some embodiments, each $R^{34}$ is independently a bond.

In some embodiments, $R^8$ is —$(CH_2)_n$—. In some embodiments, $R^8$ is —$(CH_2)_n$—, where n is an integer ranging from 1 to 4. In other embodiments, $R^8$ is —$(CH_2)_n$—, where n is an integer ranging from 1 to 2.

In some embodiments, both $R^9$ and $R^{10}$ are bonds.

In some embodiments, $R^7$ is —NH—, and $R^8$ is —$(CH_2)_n$—. In some embodiments, $R^7$ is —NH—, and $R^8$ is —$(CH_2)_n$—, where n is an integer ranging from 1 to 4. In other embodiments, $R^1$ is —NH—, and $R^8$ is —$(CH_2)_n$—, where n is an integer ranging from 1 to 2.

In some embodiments, $R^7$ is —NH—, $R^8$ is —$(CH_2)_n$—, and at least one of $R^9$ or $R^{10}$ is a bond. In some embodiments, $R^7$ is —NH—, $R^8$ is —$(CH_2)_n$—, where n is an integer ranging from 1 to 4, and at least one of $R^9$ or $R^{10}$ is a bond. In other embodiments, $R^1$ is —NH—, $R^8$ is —$(CH_2)_n$—, where n is an integer ranging from 1 to 2, and at least one of $R^9$ or $R^{10}$ is a bond. In other embodiments, $R^7$ is —NH—, $R^8$ is —$(CH_2)_n$—, where n is an integer ranging from 1 to 4, $R^9$ and $R^{10}$ are both bonds. In other embodiments, $R^7$ is —NH—, $R^8$ is —$(CH_2)_n$—, where n is an integer ranging from 1 to 2, $R^9$ and $R^{10}$ are both bonds.

Reaction Products of the Compounds of Formulas (IIA), (IIB), (IIC), (IID), (IIE), and (IIE) with Cyanate Esters In some embodiments, the compounds of any of Formulas (IIA)-(IIF) may be reacted with a dicyanate esters to form the compounds of any of Formulas (VIA) to (VIC). Suitable dicyanate esters for reaction include, but are not limited to, 2,2-bis(4-Cyanatophenyl) isopropylidene (available from Lonza under tradename Primaset BADCY), Bis-(4-Cyanato-3,5-dimethylpheny)methane, cyanated phenol-dicyclopentadine, Bis-(4-Cyanatophenyl)thioether, Bis(4-Cyanatophenyl) ether, 1,3-bis(4-Cyanatophenyl-1(1-methylidene) benzene, Resorcinol dicyanate, fused ring cyanate monomers such as naphthalene and anthraquinone, fluoroaliphatic dicyanates, Bisphenol F Cyanate ester (p-Cyanato[(p-cyanatophenyl)methyl]benzene), Primaset PT resin (Oligo(3-methylene-1,5-phenylenecyanate), Primaset LECY (p-Cyanato[1-(p-cyanatophenyl)ethyl]benzene) and mixtures thereof.

In some embodiments, the compounds of the present disclosure have the structure of Formula (VIA):

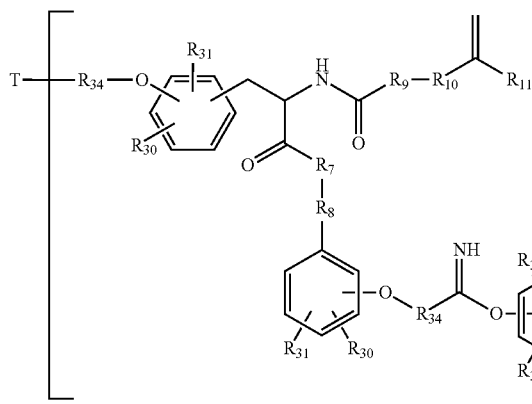 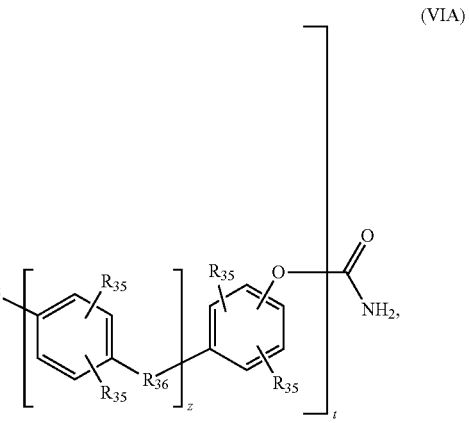 (VIA)

wherein $R^7$ is —O—, —$NR^s$—, where $R^s$ is H or a $C_1$-$C_4$ alkyl group, —S—, —$CH_2$—;

$R^s$ is a saturated or unsaturated, substituted or unsubstituted, straight chain or branched alkyl group having between 1 and 20 carbon atoms;

$R^9$ is a bond, —O—, —$(CH_2)_m$—;

$R^{10}$ is a bond; a straight chain or branched alkyl group having up to 10 carbon atoms; a straight chain or branched alkylaryl group having up to 20 carbon atoms; —($CR^aR^b$—$CR^aR^bO)_o$—, —($CR^aR^b$—$CR^aR^b$—O$)_oC(O)$— wherein $R^a$ and $R^b$ are independently H or a $C_1$-$C_4$ alkyl group; or a siloxane group;

$R^{11}$ is H or a straight chain or branched alkyl group having up to 18 carbons;

each of $R^{30}$ and $R^{31}$ is independently selected from I or H;

each $R^{34}$ is independently a bond, 4-hydroxybenzene, 3-iodo-4-hydroxybenzene, or 3,5-diiodo-4-hydroxybenzene;

each $R^{35}$ is independently an H, an aliphatic group having between 1 and 9 carbon atoms, an aromatic group having between 6 and 10 carbon atoms, an —OH group, or halogen;

each $R^{36}$ is $R^{14}$, a substituted or unsubstituted aromatic group having between 6 and 10 carbon atoms, —$CH_2$—, —$CH(CH_3)$—, —$C(CH_3)_2$—, $SO_2$, O, or S;

and where $R^{14}$ is —$CH(CH_3)$—, —$CH_2$—, —$C(CH_3)_2$—, dicyclopentadiene or a functionalized dicyclopentadiene;

T is H;

m is 0 or an integer ranging from 1 to 8;

o is an integer ranging from 1 to 500;

t is an integer ranging from 1 to 1000; and z is 0 or an integer ranging from 1 to 100.

In some embodiments, o is an integer ranging from 1 to 400. In other embodiments, o is an integer ranging from 1 to 300. In yet other embodiments, o is an integer ranging from 1 to 200. In further embodiments, o is an integer ranging from 1 to 100. In yet further embodiments, o is an integer ranging from 1 to 50.

In some embodiments, $R^8$ is —CH=CH— or (—$CH_2$-$)_n$, wherein n ranges from 1 to 20. In some embodiments, n ranges from to 1 to 16. In other embodiments, n ranges from to 1 to 16. In yet other embodiments, n ranges from to 1 to 12. In further embodiments, n ranges from to 1 to 8. In even further embodiments, n ranges from to 1 to 6. In some embodiments, $R^8$ is —$CH_2CH_2CH_2CH_2$—. In other embodiments, $R^8$ is —$CH_2CH_2CH_2$—. In yet other embodiments, $R^8$ is —$CH_2CH_2$—. In further embodiments, $R^8$ is —$CH_2$—.

In some embodiments, $R^{10}$ is —$(CH_2)_p$—, where p ranges from 1 to 12. In some embodiments, p ranges from 1 to 6. In other embodiments, p ranges from 1 to 4. In yet other embodiments, p is 1 or 2.

In some embodiments, $R^{10}$ is —$(CH_2CH_2O)_o$—, —$(CH_2CH_2O)_oC(O)$—, where o ranges from 1 to 250. In some embodiments, $R^{10}$ is —$(CH_2CH_2O)_o$—, —$(CH_2CH_2O)_oC(O)$—, where o ranges from 1 to 100. In some embodiments, $R^{10}$ is —$(CH_2CH_2O)_o$—, —$(CH_2CH_2O)_oC(O)$—, where o ranges from 1 to 50. In some embodiments, $R^{10}$ is —$(CH_2CH_2O)_o$—, —$(CH_2CH_2O)_oC(O)$—, where o ranges from 1 to 10. In other embodiments, $R^{10}$ is —$(CH_2CH_2O)_o$—, —$(CH_2CH_2O)_oC(O)$—, where o ranges from 1 to 6.

In some embodiments, $R^{11}$ is H. In other embodiments, $R^{11}$ is methyl.

In some embodiments, $R^{35}$ is OH and $R^{36}$ is —$CH_2$—, —$CH(CH_3)$— or —$C(CH_3)_2$.

An example of a compound having Formula (VIA) is set forth below:

In some embodiments, the compounds of the present disclosure have the structure of Formulas (VIB) and (VIC):

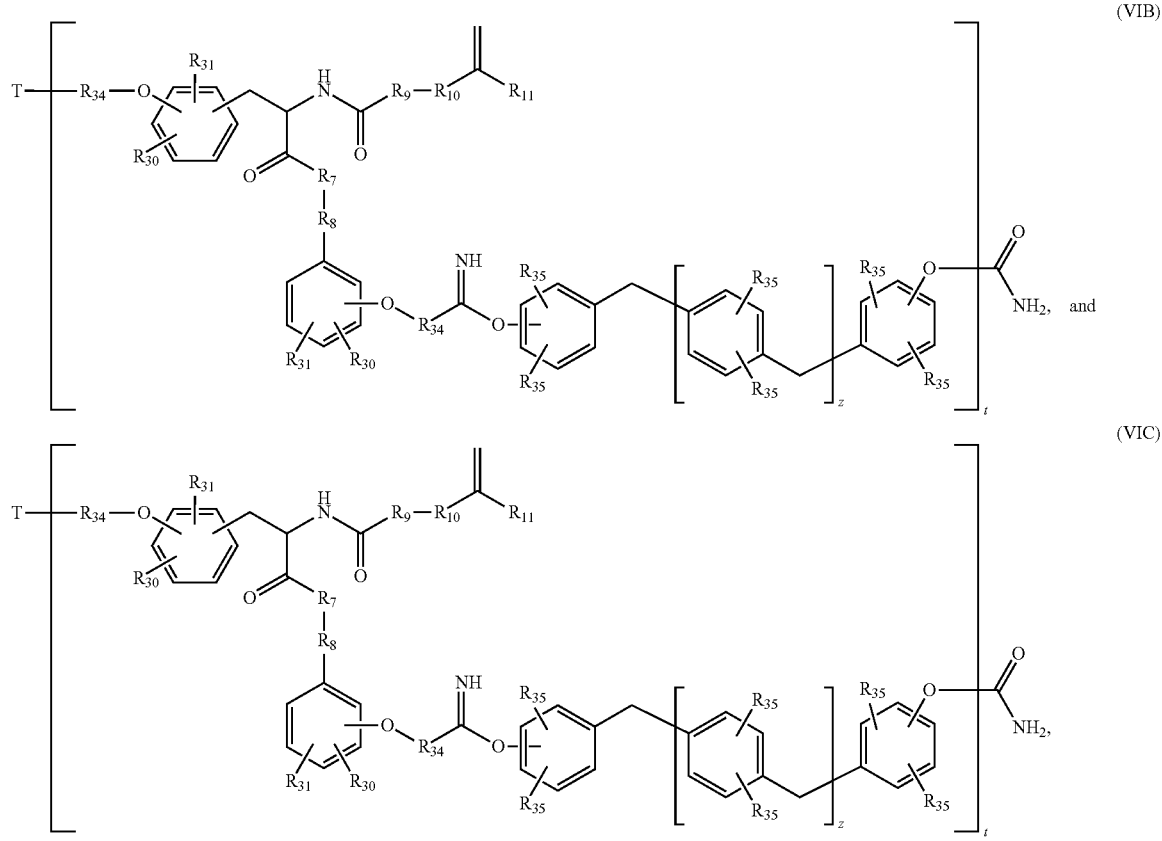

wherein $R^7$ is —O—, —$NR^s$—, where $R^s$ is H or a $C_1$-$C_4$ alkyl group, —S—, —$CH_2$—;

$R^8$ is a saturated or unsaturated, substituted or unsubstituted, straight chain or branched alkyl group having between 1 and 20 carbon atoms;

$R^9$ is a bond, —O—, —$(CH_2)_m$—;

$R^{10}$ is a bond; a straight chain or branched alkyl group having up to 10 carbon atoms; a straight chain or branched alkylaryl group having up to 20 carbon atoms; —$(CR^aR^b$—$CR^aR^bO)_o$—, —$(CR^aR^b$—$CR^aR^b$—O$)_o$C(O)— wherein $R^a$ and $R^b$ are independently H or a $C_1$-$C_4$ alkyl group; or a siloxane group;

$R^{11}$ is H or a straight chain or branched alkyl group having up to 18 carbons;

each of $R^{30}$ and $R^{31}$ is independently selected from I or H;

each $R^{34}$ is independently a bond, 4-hydroxybenzene, 3-iodo-4-hydroxybenzene, or 3,5-diiodo-4-hydroxybenzene;

each $R^{35}$ is independently an H, an aliphatic group having between 1 and 9 carbon atoms, an aromatic group having between 6 and 10 carbon atoms, an —OH group, or halogen;

each $R^{36}$ is $R^{14}$, a substituted or unsubstituted aromatic group having between 6 and 10 carbon atoms, —$CH_2$—, —$CH(CH_3)$—, —$C(CH_3)_2$—, $SO_2$, O, or S;

and where $R^{14}$ is —$CH(CH_3)$—, —$CH_2$—, —$C(CH_3)_2$—, dicyclopentadiene or a functionalized dicyclopentadiene;

T is H;

m is 0 or an integer ranging from 1 to 8;

o is an integer ranging from 1 to 500;

t is an integer ranging from 1 to 1000; and z is 0 or an integer ranging from 1 to 100.

In some embodiments, o is an integer ranging from 1 to 400. In other embodiments, o is an integer ranging from 1 to 300. In yet other embodiments, o is an integer ranging from 1 to 200. In further embodiments, o is an integer ranging from 1 to 100. In yet further embodiments, o is an integer ranging from 1 to 50.

In some embodiments, $R^8$ is —CH=CH— or (—$CH_2$-$)_n$, wherein n ranges from 1 to 20. In some embodiments, n ranges from to 1 to 16. In other embodiments, n ranges from to 1 to 16. In yet other embodiments, n ranges from to 1 to 12. In further embodiments, n ranges from to 1 to 8. In even further embodiments, n ranges from to 1 to 6. In some embodiments, $R^8$ is —$CH_2CH_2CH_2CH_2$—. In other embodiments, $R^8$ is —$CH_2CH_2CH_2$—. In yet other embodiments, $R^8$ is —$CH_2CH_2$—. In further embodiments, $R^8$ is —$CH_2$—.

In some embodiments, $R^{10}$ is —$(CH_2)_p$—, where p ranges from 1 to 12. In some embodiments, p ranges from 1 to 6. In other embodiments, p ranges from 1 to 4. In yet other embodiments, p is 1 or 2.

In some embodiments, $R^{10}$ is —$(CH_2CH_2O)_o$—, —$(CH_2CH_2O)_oC(O)$—, where o ranges from 1 to 250. In some embodiments, $R^{10}$ is —$(CH_2CH_2O)_o$—, —$(CH_2CH_2O)_oC(O)$—, where o ranges from 1 to 100. In some embodiments, $R^{10}$ is —$(CH_2CH_2O)_o$—, —$(CH_2CH_2O)_oC(O)$—, where o ranges from 1 to 50. In some embodiments, $R^{10}$ is —$(CH_2CH_2O)_o$—, —$(CH_2CH_2O)_oC(O)$—, where o ranges from 1 to 10. In other embodiments, $R^{10}$ is —$(CH_2CH_2O)_o$—, —$(CH_2CH_2O)_oC(O)$—, where o ranges from 1 to 6.

In some embodiments, $R^{11}$ is H. In other embodiments, $R^{11}$ is methyl.

In some embodiments, $R^{35}$ is OH and $R^{36}$ is —CH$_2$—, —CH(CH$_3$)— or —C(CH$_3$)$_2$.

Crosslinked and/or Polymerized Compositions

In in some embodiments, the compounds of any of Formulas (IIIA) to (IIIC) may be polymerized upon exposure to electromagnetic radiation to form the compounds of any of Formulas (VIIA) to (VIIE).

In some embodiments, the compounds of the present disclosure have any of Formulas (VIIA), (VIIB), (VIIC), (VIID), or (VIIE):

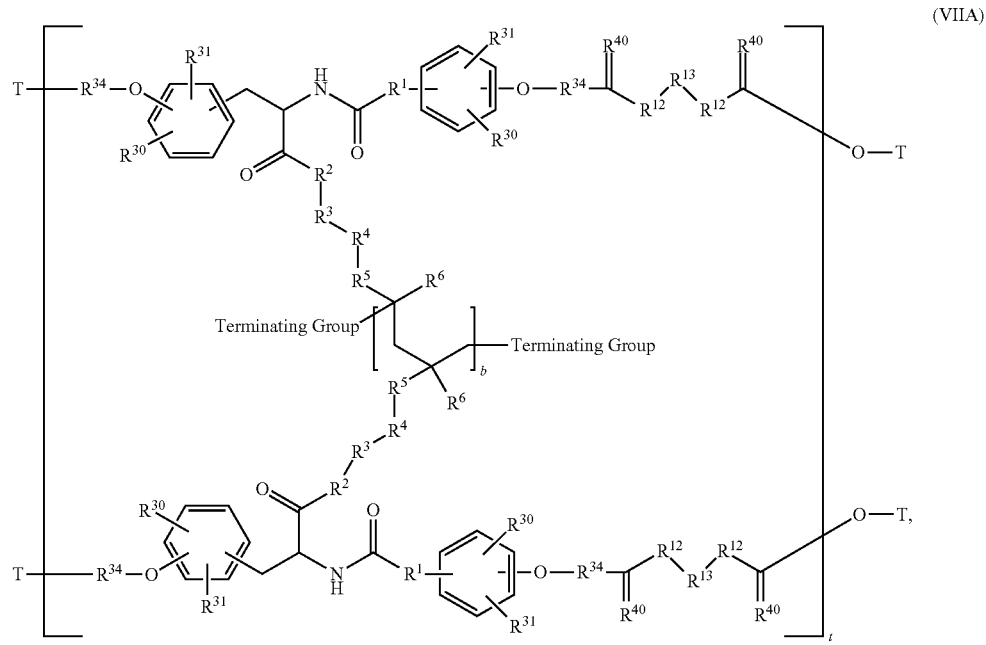

(VIIA)

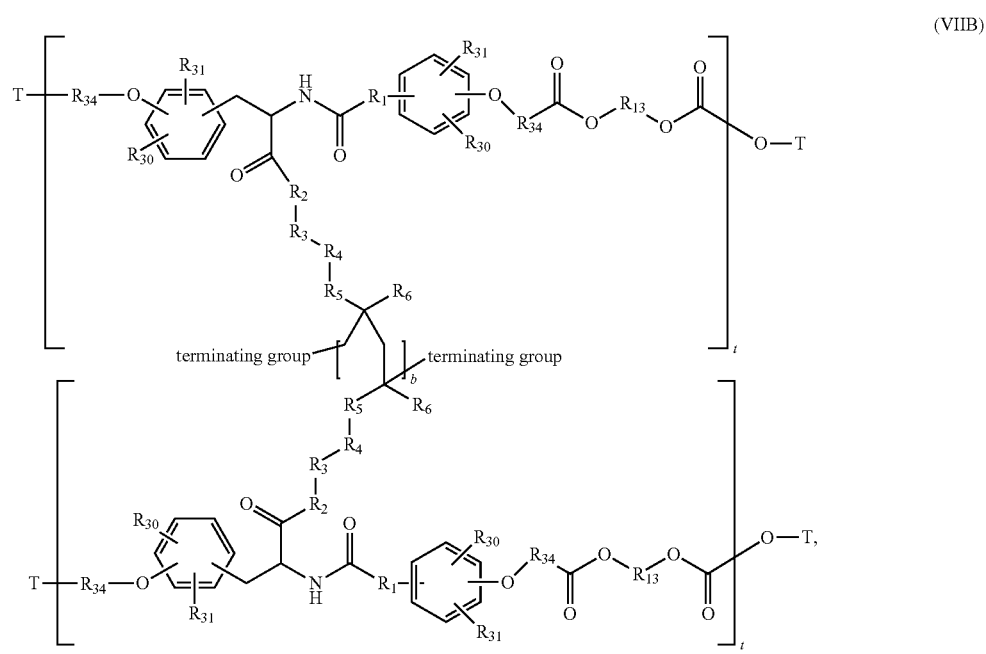

(VIIB)

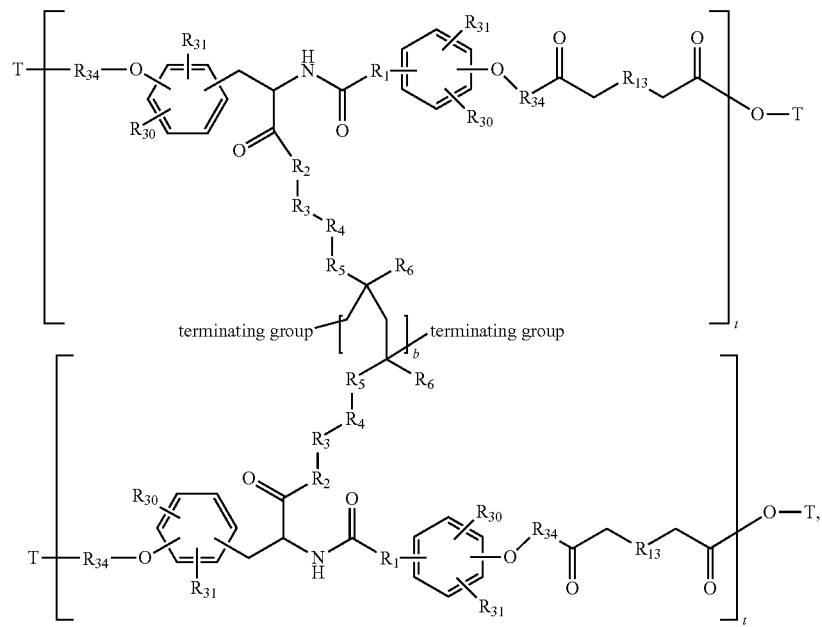
(VIIC)
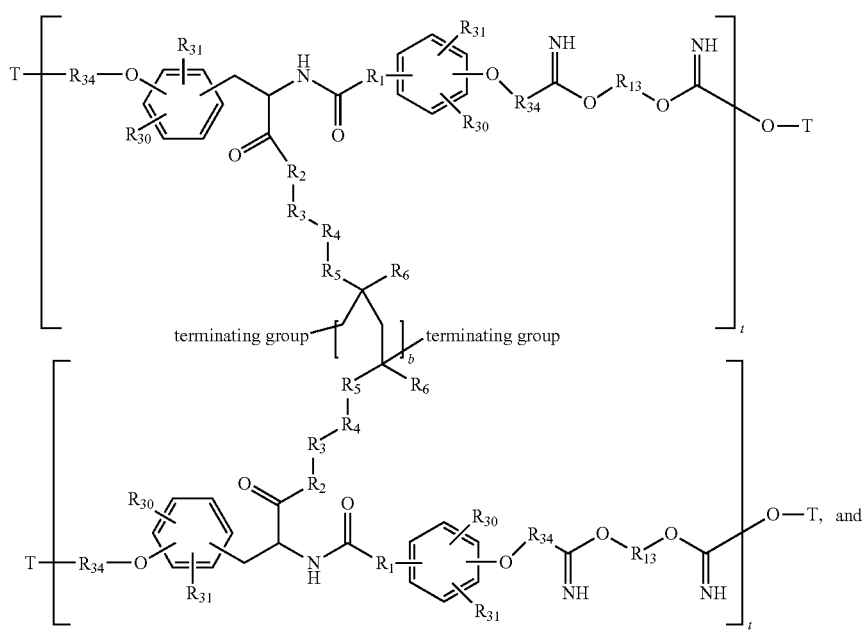
(VIID)

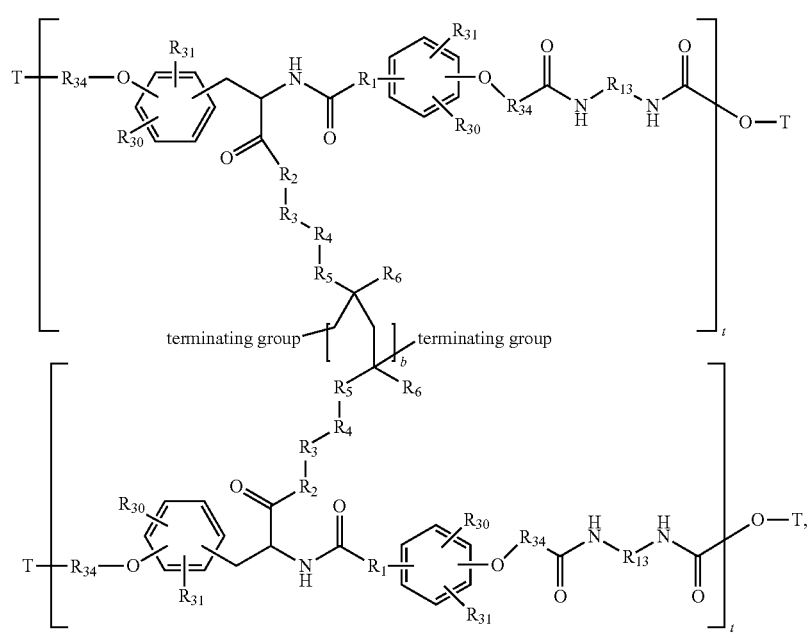

(VIIE)

wherein $R^1$ is —CH=CH— or (—CH$_2$-)$_n$;

$R^2$ is —O—, —NR$^s$—, where $R^s$ is H or a $C_1$-$C_4$ alkyl group, or —S—;

$R^3$ is a straight chain or branched alkyl group having up to 10 carbon atoms, a straight chain or branched alkylaryl group having up to 20 carbon atoms, or siloxane group;

$R^4$ is —O—, —NR$^s$—, where $R^s$ is H or a $C_1$-$C_4$ alkyl group, —S—, —CH$_2$—;

$R^5$ is C=O, —CH$_2$—, a benzyl group, or a substituted benzyl group;

$R^6$ is H or a straight chain or branched alkyl group having up to 18 carbons atoms;

each $R^{12}$ is independently a bond, —CH$_2$—, —O—, or —NR$^s$—, where $R^s$ is H or a $C_1$-$C_4$ alkyl group;

$R^{13}$ is a substituted or unsubstituted aliphatic group having between 1 and 5000 carbon atoms and optionally including one or more heteroatoms selected from O, N, or S; —(CH$_2$—O—(CH$_2$—O)$_v$—CH$_2$)—; or a substituted or unsubstituted aromatic group having between 6 and 280 carbon atoms;

each of $R^{30}$ and $R^{31}$ is independently selected from I or H;

each $R^{34}$ is independently a bond, 4-hydroxybenzene, 3-iodo-4-hydroxybenzene, or 3,5-diiodo-4-hydroxybenzene;

each $R^{40}$ is independently O or NH;

T is H;

the terminating group is derived from an initiator;

b is an integer ranging from 0 to 1000;

n is 0 or an integer ranging from 1 to 8;

t is an integer ranging from 1 to 1000; and v is 0 or an integer ranging from 1 to 5000.

In some embodiments, the terminating group is (C$_6$H$_6$)—C(O)— or —(C)(OH)(CH$_3$)$_2$. In other embodiments, the terminating group is derived from 2-dimethoxy-2-phenylacetophenone, benzoyl formates, acyl-phosphine oxides, acyl phosphinates, alpha-amino alkyl-phenones, alpha-hydroxy alkylphenones, alpha-dialkoxy acetophenones, benzophenones/amines, thioxanthines/amines, bis(4-tert-butylphenyl) iodonium perfluoro-1-butanesulfonate, diphenyliodonium nitrate. In yet other embodiments, the terminating group is derived from camphorquinone, fluoresceins such as Eosin Y and Rose Bengal, Riboflavin, and lumichrome.

In in some embodiments, the compounds of any of Formulas (VA) to (VB) may be polymerized upon exposure to electromagnetic radiation to form the compounds of any of Formulas (VIIIA) to (VIIIE):

In some embodiments, the compounds of the present disclosure have any of Formulas (VIIIA), (VIIIB), (VIIIC), (VIIID), or (VIIIE):

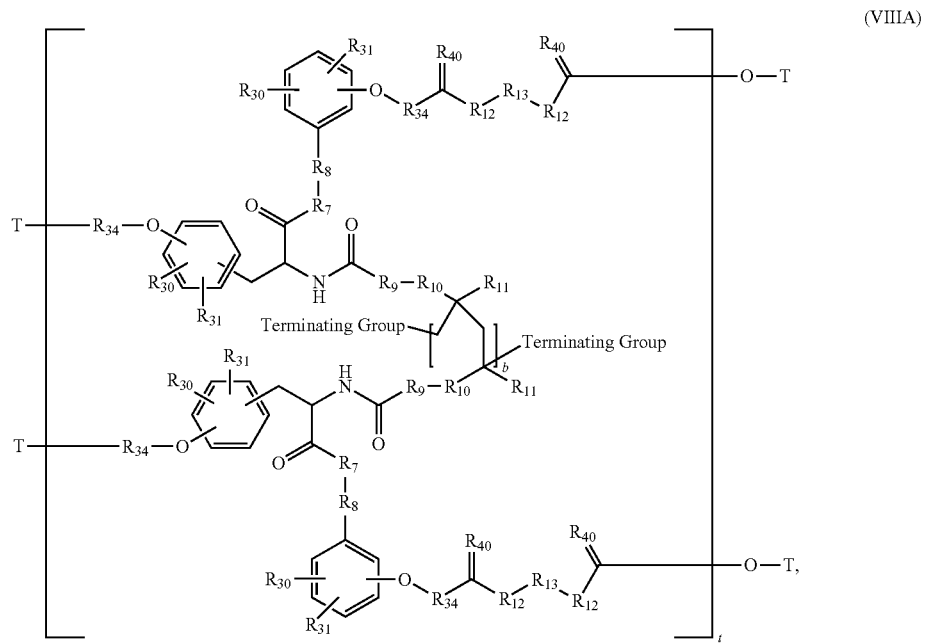
(VIIIA)
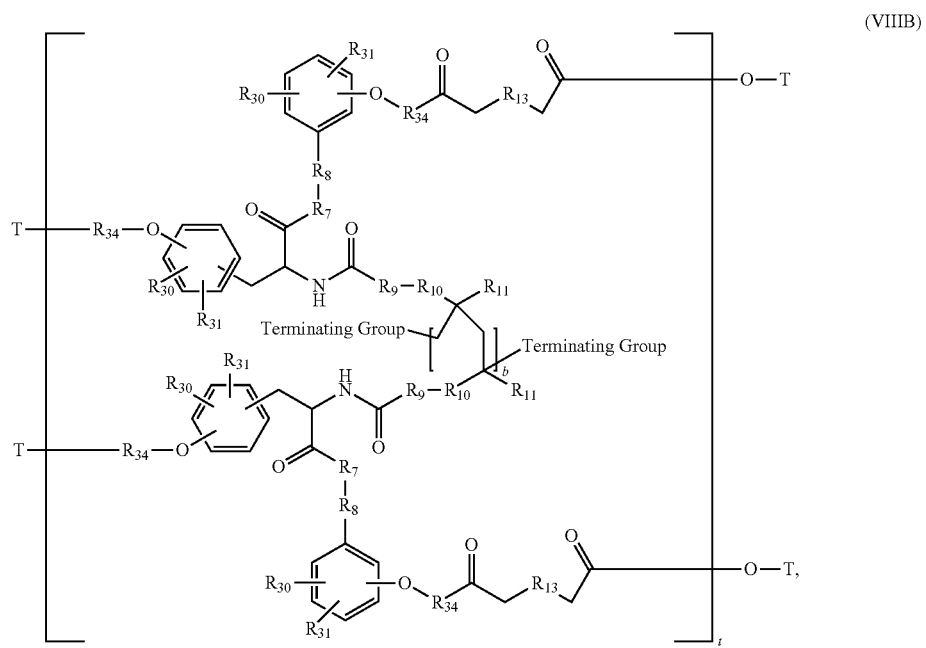
(VIIIB)

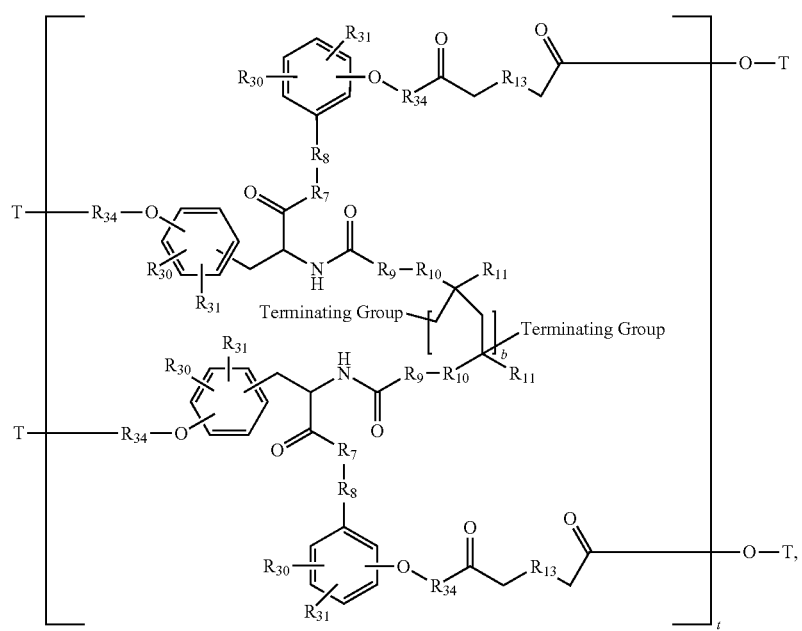
(VIIIC)
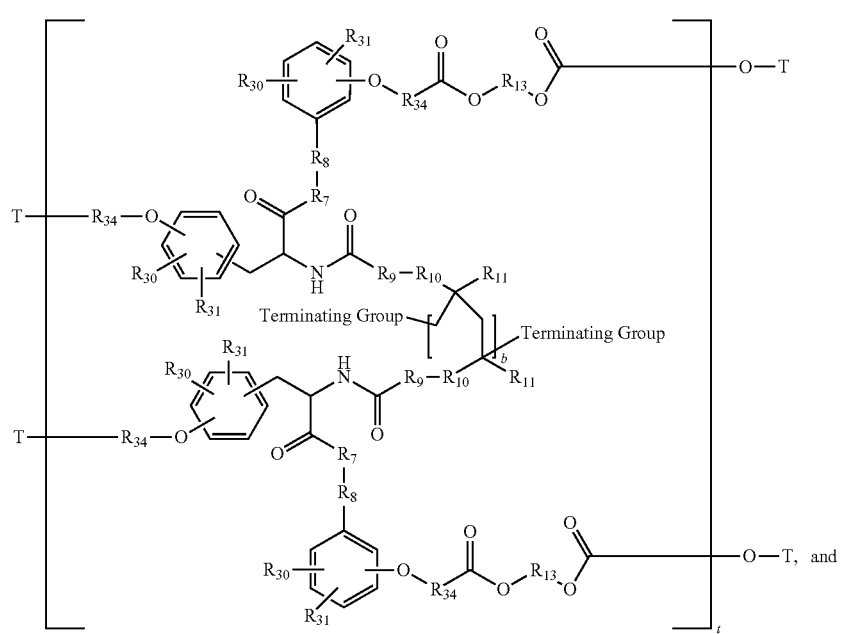
(VIIID)

-continued (VIIIE)

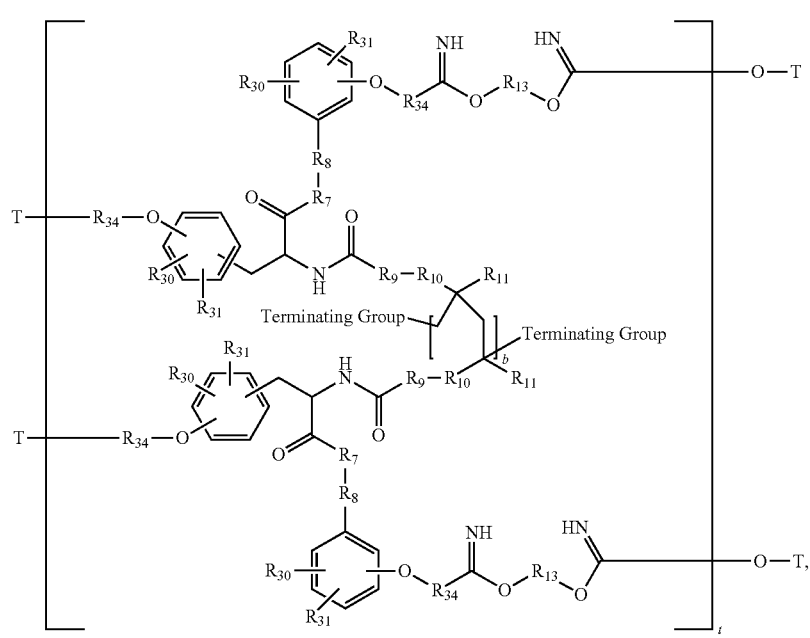

wherein $R^7$ is —O—, —$NR^s$—, where $R^s$ is H or a $C_1$-$C_4$ alkyl group, —S—, —$CH_2$—;

$R^8$ is a saturated or unsaturated, substituted or unsubstituted, straight chain or branched alkyl group having between 1 and 20 carbon atoms;

$R^9$ is a bond, —O—, —$(CH_2)_m$—;

$R^{10}$ is a bond; a straight chain or branched alkyl group having up to 10 carbon atoms; a straight chain or branched alkylaryl group having up to 20 carbon atoms; —($CR^aR^b$—$CR^aR^bO)_o$—, —($CR^aR^b$—$CR^aR^b$—O)$_o$C(O)— wherein $R^a$ and $R^b$ are independently H or a $C_1$-$C_4$ alkyl group; or a siloxane group;

$R^{11}$ is H or a straight chain or branched alkyl group having up to 18 carbons;

each $R^{12}$ is independently a bond, —$CH_2$—, —O—, or —$NR^s$—, where $R^s$ is H or a $C_1$-$C_4$ alkyl group;

$R^{13}$ is a substituted or unsubstituted aliphatic group having between 1 and 5000 carbon atoms and optionally including one or more heteroatoms selected from O, N, or S; —$(CH_2$—O—$(CH_2$—O)$_v$—$CH_2)$—; or a substituted or unsubstituted aromatic group having between 6 and 280 carbon atoms;

each of $R^{30}$ and $R^{31}$ is independently selected from I or H;

each $R^{34}$ is independently a bond, 4-hydroxybenzene, 3-iodo-4-hydroxybenzene, or 3,5-diiodo-4-hydroxybenzene;

each $R^{40}$ is independently O or NH;

T is H;

the terminating group is derived from an initiator;

b is an integer ranging from 0 to 1000;

m is 0 or an integer ranging from 1 to 8;

o is an integer ranging from 1 to 500;

t is an integer ranging from 1 to 1000; and v is 0 or an integer ranging from 1 to 5000.

In some embodiments, the terminating group is ($C_6H_6$)—C(O)— or —(C)(OH)($CH_3$)$_2$. In other embodiments, the terminating group is derived from 2-dimethoxy-2-phenylacetophenone, benzoyl formates, acyl-phosphine oxides, acyl phosphinates, alpha-amino alkyl-phenones, alpha-hydroxy alkylphenones, alpha-dialkoxy acetophenones, benzophenones/amines, thioxanthines/amines, bis(4-tert-butylphenyl) iodonium perfluoro-1-butanesulfonate, diphenyliodonium nitrate. In yet other embodiments, the terminating group is derived from camphorquinone, fluoresceins such as Eosin Y and Rose Bengal, Riboflavin, and lumichrome.

Non-limiting examples of the compounds of Formula (VIIIA) include the following:

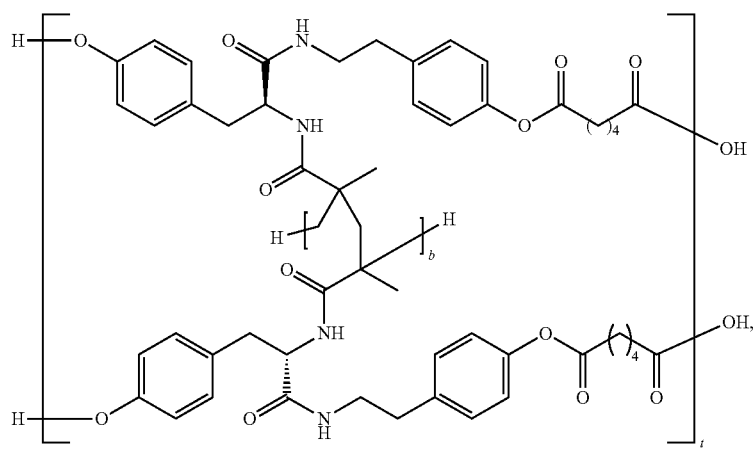

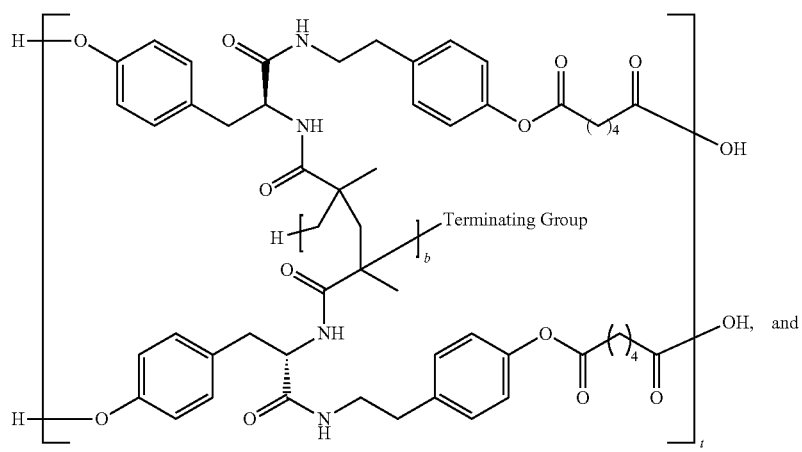

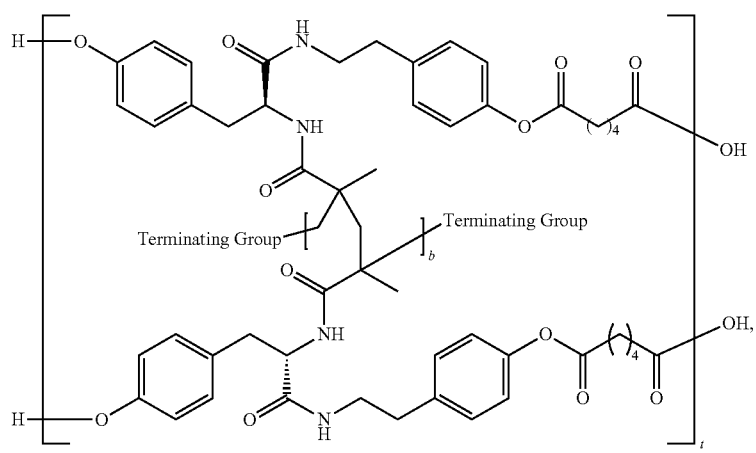

wherein, in some embodiments, the terminating group is (C$_6$H$_6$)—C(O)— or —(C)(OH)(CH$_3$)$_2$. In other embodiments, the terminating group is derived from 2-dimethoxy-2-phenylacetophenone, benzoyl formates, acyl-phosphine oxides, acyl phosphinates, alpha-amino alkyl-phenones, alpha-hydroxy alkylphenones, alpha-dialkoxy acetophenones, benzophenones/amines, thioxanthines/amines, bis(4-tert-butylphenyl)iodonium perfluoro-1-butanesulfonate, diphenyliodonium nitrate. In yet other embodiments, the terminating group is derived from camphorquinone, fluoresceins such as Eosin Y and Rose Bengal, Riboflavin, and lumichrome.

In in some embodiments, the compounds of any of Formulas (IA) to (IE) may be polymerized upon exposure to electromagnetic radiation to form the compounds of any of Formulas (VIXA) to (VIXB):

In some embodiments, the compounds of the present disclosure have Formula (IXA):

(IXA)

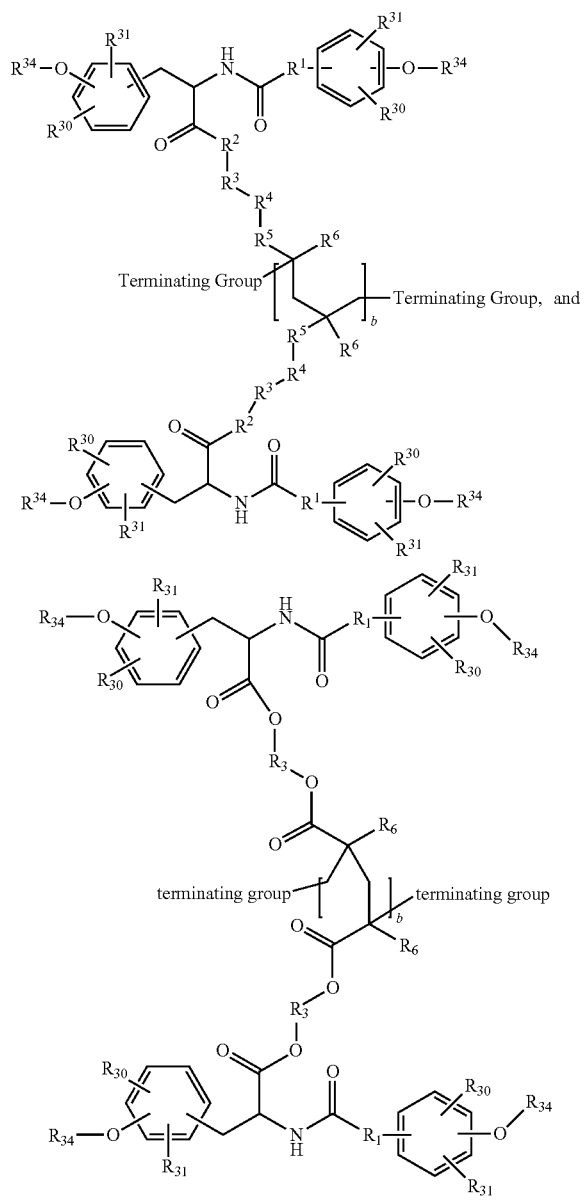

wherein
$R^1$ is —CH=CH— or (—CH$_2$—)$_n$;
$R^2$ is —O—, —NR$^s$—, where R$^s$ is H or a $C_1$-$C_4$ alkyl group, or —S—;
$R^3$ is a straight chain or branched alkyl group having up to 10 carbon atoms, a straight chain or branched alkylaryl group having up to 20 carbon atoms, or siloxane group;
$R^4$ is —O—, —NR$^s$—, where R$^s$ is H or a C1-$C_4$ alkyl group, —S—, —CH$_2$—;
$R^5$ is C=O, —CH$_2$—, a benzyl group, or a substituted benzyl group;
$R^6$ is H or a straight chain or branched alkyl group having up to 18 carbons atoms;
each of $R^{30}$ and $R^{31}$ is independently selected from I or H;
each $R^{34}$ is independently a bond, 4-hydroxybenzene, 3-iodo-4-hydroxybenzene, or 3,5-diiodo-4-hydroxybenzene;
the terminating group is derived from an initiator;

b is an integer ranging from 0 to 1000; and
n is 0 or an integer ranging from 1 to 8.

In some embodiments, the terminating group is ($C_6H_6$)—C(O)— or —(C)(OH)(CH$_3$)$_2$. In other embodiments, the terminating group is derived from 2-dimethoxy-2-phenylacetophenone, benzoyl formates, acyl-phosphine oxides, acyl phosphinates, alpha-amino alkyl-phenones, alpha-hydroxy alkylphenones, alpha-dialkoxy acetophenones, benzophenones/amines, thioxanthines/amines, bis(4-tert-butylphenyl) iodonium perfluoro-1-butanesulfonate, diphenyliodonium nitrate. In yet other embodiments, the terminating group is derived from camphorquinone, fluoresceins such as Eosin Y and Rose Bengal, Riboflavin, and lumichrome.

In in some embodiments, the compounds of any of Formulas (IIA) to (IIF) may be polymerized upon exposure to electromagnetic radiation to form the compounds of Formula (X):

In some embodiments, the compounds of the present disclosure have Formula (X):

(X)

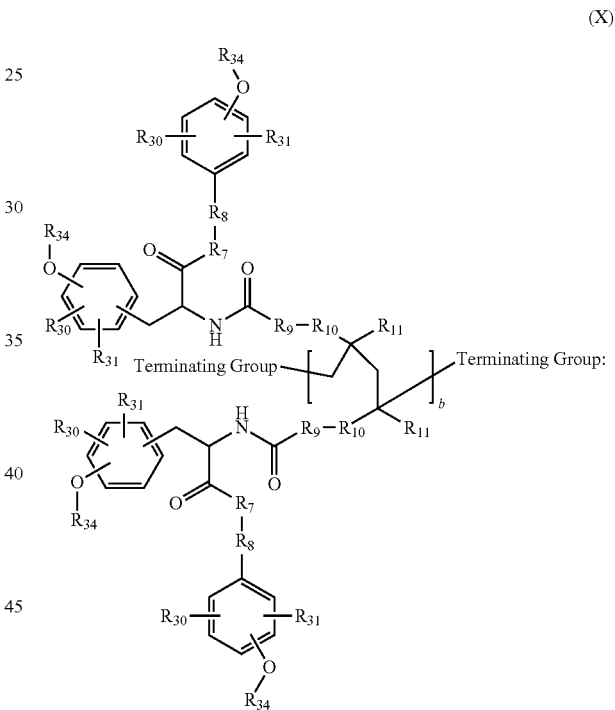

wherein
$R^7$ is —O—, —NR$^s$—, where R$^s$ is H or a $C_1$-$C_4$ alkyl group, —S—, —CH$_2$—;
$R^8$ is a saturated or unsaturated, substituted or unsubstituted, straight chain or branched alkyl group having between 1 and 20 carbon atoms;
$R^9$ is a bond, —O—, —(CH$_2$)$_m$—;
$R^{10}$ is a bond; a straight chain or branched alkyl group having up to 10 carbon atoms; a straight chain or branched alkylaryl group having up to 20 carbon atoms; —(CR$^a$R$^b$—CR$^a$R$^b$O)$_p$—, —(CR$^a$R$^b$—CR$^a$R$^b$—O)$_o$—C(O)— wherein $R^a$ and $R^b$ are independently H or a $C_1$-$C_4$ alkyl group; or a siloxane group;
$R^{11}$ is H or a straight chain or branched alkyl group having up to 18 carbons;
each $R^{12}$ is independently —CH$_2$—, —O—, or —NR$^s$—, where R$^s$ is H or a $C_1$-$C_4$ alkyl group;

$R^{13}$ is a substituted or unsubstituted aliphatic group having between 1 and 5000 carbon atoms and optionally including one or more heteroatoms selected from O, N, or S; —($CH_2$—O—($CH_2$—O)$_v$—$CH_2$)—; or a substituted or unsubstituted aromatic group having between 6 and 280 carbon atoms;

each of $R^{30}$ and $R^{31}$ is independently selected from I or H;

each $R^{34}$ is independently a bond, 4-hydroxybenzene, 3-iodo-4-hydroxybenzene, or 3,5-diiodo-4-hydroxybenzene;

the terminating group is derived from an initiator;

b is an integer ranging from 0 to 1000;

m is 0 or an integer ranging from 1 to 8;

v is 0 or an integer ranging from 1 to 5000;

o is an integer ranging from 1 to 500.

In some embodiments, the terminating group is ($C_6H_6$)—C(O)— or —(C)(OH)($CH_3$)$_2$. In other embodiments, the terminating group is derived from 2-dimethoxy-2-phenylacetophenone, benzoyl formates, acyl-phosphine oxides, acyl phosphinates, alpha-amino alkyl-phenones, alpha-hydroxy alkylphenones, alpha-dialkoxy acetophenones, benzophenones/amines, thioxanthines/amines, bis(4-tert-butylphenyl) iodonium perfluoro-1-butanesulfonate, diphenyliodonium nitrate. In yet other embodiments, the terminating group is derived from camphorquinone, fluoresceins such as Eosin Y and Rose Bengal, Riboflavin, and lumichrome.

In some embodiments, the compounds of any of Formulas (IVA) to (IVE) may be polymerized upon exposure to electromagnetic radiation to form the compounds of any of Formulas (XIA) to (XIC):

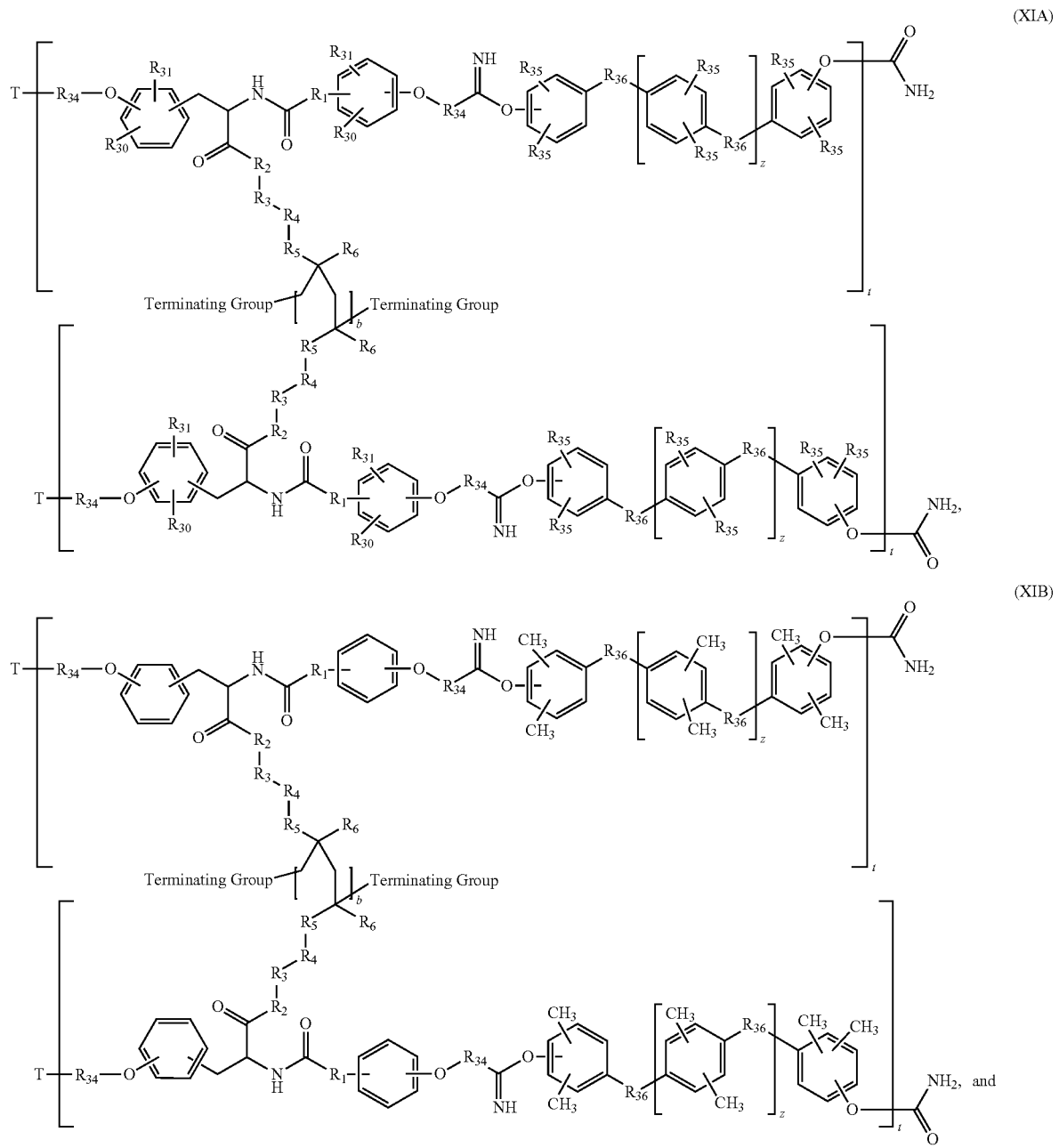

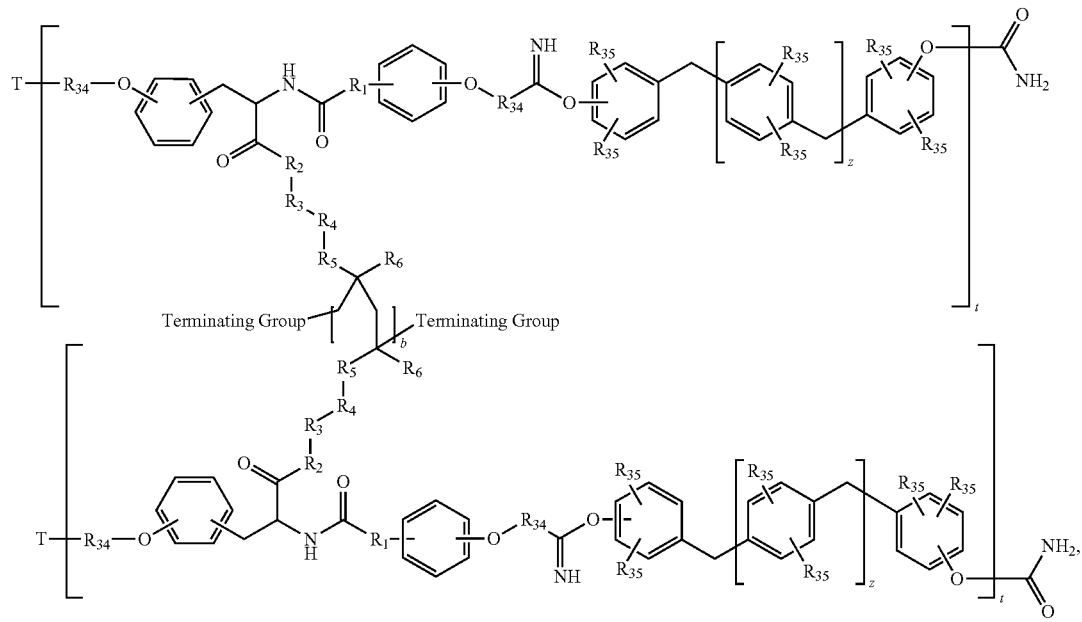

wherein
$R^1$ is —CH=CH— or (—CH$_2$-)$_n$;
$R^2$ is —O—, —NR$^s$—, where R$^s$ is H or a $C_1$-$C_4$ alkyl group, or —S—;
$R^3$ is a straight chain or branched alkyl group having up to 10 carbon atoms, a straight chain or branched alkylaryl group having up to 20 carbon atoms, or siloxane group;
$R^4$ is —O—, —NR$^s$—, where R$^s$ is H or a $C_1$-$C_4$ alkyl group, —S—, —CH$_2$—;
$R^5$ is C=O, —CH$_2$—, a benzyl group, or a substituted benzyl group;
$R^6$ is H or a straight chain or branched alkyl group having up to 18 carbons atoms;
each of $R^{30}$ and $R^{31}$ is independently selected from I or H;
each $R^{34}$ is independently a bond, 4-hydroxybenzene, 3-iodo-4-hydroxybenzene, or 3,5-diiodo-4-hydroxybenzene;
each $R^{35}$ is independently an H, an aliphatic group having between 1 and 9 carbon atoms, an aromatic group having between 6 and 10 carbon atoms, an —OH group, or halogen;
each $R^{36}$ is $R^{14}$, a substituted or unsubstituted aromatic group having between 6 and 10 carbon atoms, CH$_2$, CH(CH$_3$), C(CH$_3$)$_2$, SO$_2$, O, or S;
and where $R^{14}$ is —CH(CH$_3$)—, —CH$_2$—, —C(CH$_3$)$_2$—, dicyclopentadiene or a functionalized dicyclopentadiene;
T is H;
t is an integer ranging from 1 to 1000;
n is 0 or an integer ranging from 1 to 8;
b is an integer ranging from 0 to 1000; and
z is 0 or an integer ranging from 1 to 10.
In some embodiments, $R^1$ is —CH=CH— or (—CH$_2$-)$_n$, wherein n ranges from 1 to 8. In some embodiments, n ranges from to 1 to 4. In other embodiments, $R^1$ is —CH$_2$CH$_2$CH$_2$CH$_2$—. In other embodiments, $R^1$ is —CH$_2$CH$_2$CH$_2$—. In yet other embodiments, $R^1$ is —CH$_2$CH$_2$—. In further embodiments, $R^1$ is —CH$_2$—.
In some embodiments, $R^3$ is a $C_1$-$C_8$ straight chain or branched alkyl group. In other embodiments, $R^3$ is a $C_1$-$C_6$ straight chain or branched alkyl group. In yet other embodiments, $R^3$ is a $C_1$-$C_4$ straight chain or branched alkyl group.
In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 16 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 12 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 9 carbon atoms.
In some embodiments, the siloxane group has the structure of —(R′′′)(R′′)—Si—O—Si—(R′′)(R′′′)—, or —(R′′′)(R′′)—Si—[O—Si—(R′′)(R′′′)]$_h$—O—Si—(R′′)(R′′′)—, wherein R′′′ and R′′ are independently selected from $C_1$-$C_4$ alkyl, $C_6$ aryl, or H and herein h ranges from 1 to 2000. In some embodiments, h ranges from 1 to 1500. In other embodiments, h ranges from 1 to 1000. In yet other embodiments, h ranges from 1 to 750. In further embodiments, h ranges from 1 to 500. In yet further embodiments, h ranges from 1 to 250.
In some embodiments, $R^3$ is 2,2-dimethyl propane or sec-butane. In other embodiments, $R^3$ is derived from 2,2-diphenyl propane. In some embodiments, $R^3$ is derived from poly(dimethylsiloxane) having a molecular weight ranging from about 70 to about 100,000; or derived from poly(diarylsiloxane) having a molecular weight ranging from about 190 to about 100,000.
In some embodiments, $R^5$ is —C(O)—, —CH$_2$— or —C(H)(Ph)-. In some embodiments, $R^5$ is —CH$_2$—. In some embodiments, $R^5$ is —C(O)—.
In some embodiments, $R^6$ is H. In other embodiments, $R^6$ is a $C_1$-$C_8$ straight chain or branched alkyl group. In other embodiments, $R^6$ is a $C_1$-$C_6$ straight chain or branched alkyl group. In yet other embodiments, $R^6$ is a $C_1$-$C_4$ straight chain or branched alkyl group. In further embodiments, $R^6$ is methyl.

In some embodiments, $R^{13}$ is —$(CH_2)_u$—, where u is 0 or an integer ranging from 1 to 5000; or a group —$(C_6H_4$—O—$(C_6H_4$—O$)_w$—$C_6H_4$—, where w is 0 or an integer ranging from 1 to 40.

In some embodiments, $R^{35}$ is OH and $R^{36}$ is —$CH_2$—, —$CH(CH_3)$— or —$C(CH_3)_2$.

In some embodiments, the compounds of Formulas (VIA) and (VIE) may be polymerized upon exposure to electromagnetic radiation to form the compounds of Formula (XII):

ing one or more heteroatoms selected from O, N, or S; —$(CH_2$—O—$(CH_2$—O$)_v$—$CH_2)$—; or a substituted or unsubstituted aromatic group having between 6 and 280 carbon atoms;

each of $R^{30}$ and $R^{31}$ is independently selected from I or H;

each $R^{34}$ is independently a bond, 4-hydroxybenzene, 3-iodo-4-hydroxybenzene, or 3,5-diiodo-4-hydroxybenzene;

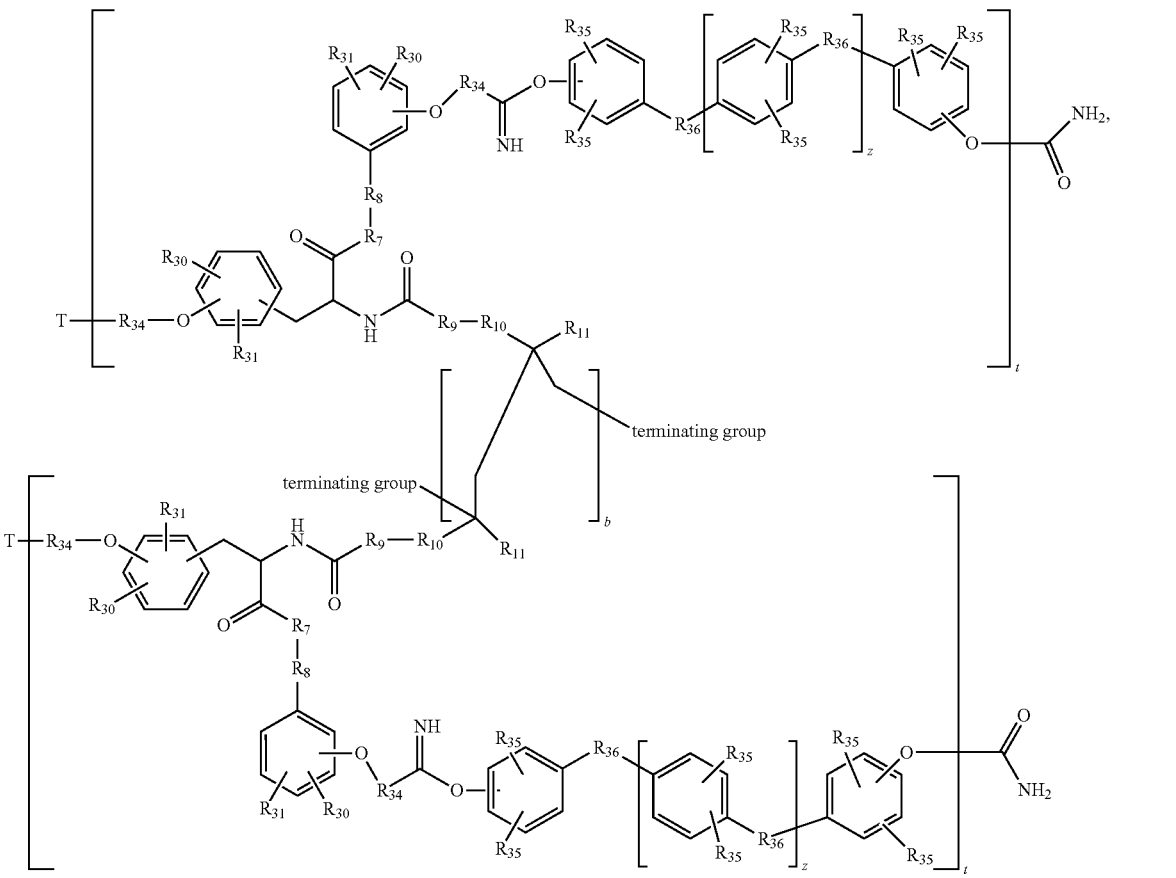

(XII)

wherein $R^7$ is —O—, —$NR^s$—, where $R^s$ is H or a $C_1$-$C_4$ alkyl group, —S—, —$CH_2$—;

$R^8$ is a saturated or unsaturated, substituted or unsubstituted, straight chain or branched alkyl group having between 1 and 20 carbon atoms;

$R^9$ is a bond, —O—, —$(CH_2)_m$—;

$R^{10}$ is a bond; a straight chain or branched alkyl group having up to 10 carbon atoms; a straight chain or branched alkylaryl group having up to 20 carbon atoms; —$(CR^aR^b$—$CR^aR^bO)_o$—, —$(CR^aR^b$—$CR^aR^b$—O$)_o$—C(O)— wherein $R^a$ and $R^b$ are independently H or a $C_1$-$C_4$ alkyl group; or a siloxane group;

$R^{11}$ is H or a straight chain or branched alkyl group having up to 18 carbons;

each $R^{12}$ is independently a bond, —$CH_2$—, —O—, or —$NR^s$—, where $R^s$ is H or a $C_1$-$C_4$ alkyl group;

$R^{13}$ is a substituted or unsubstituted aliphatic group having between 1 and 5000 carbon atoms and optionally includeach $R^{35}$ is independently an H, an aliphatic group having between 1 and 9 carbon atoms, an aromatic group having between 6 and 10 carbon atoms, an —OH group, or halogen;

each $R^{36}$ is $R^{14}$, a substituted or unsubstituted aromatic group having between 6 and 10 carbon atoms, —$CH_2$—, —$CH(CH_3)$—, —$C(CH_3)_2$—, $SO_2$, O, or S;

where $R^{14}$ is —$CH(CH_3)$—, —$CH_2$—, —$C(CH_3)_2$—, dicyclopentadiene or a functionalized dicyclopentadiene;

T is H;

m is 0 or an integer ranging from 1 to 8;

o is an integer ranging from 1 to 500; and t is an integer ranging from 1 to 1000;

b is an integer ranging from 0 to 1000; and z is 0 or an integer ranging from 1 to 100.

In some embodiments, o is an integer ranging from 1 to 400. In other embodiments, o is an integer ranging from 1 to 300. In yet other embodiments, o is an integer ranging from 1 to 200. In further embodiments, o is an integer ranging from 1 to 100. In yet further embodiments, o is an integer ranging from 1 to 50.

In some embodiments, $R^8$ is —CH=CH— or (—CH$_2$-)$_n$, wherein n ranges from 1 to 20. In some embodiments, n ranges from to 1 to 16. In other embodiments, n ranges from to 1 to 16. In yet other embodiments, n ranges from to 1 to 12. In further embodiments, n ranges from to 1 to 8. In even further embodiments, n ranges from to 1 to 6. In some embodiments, $R^8$ is —CH$_2$CH$_2$CH$_2$CH$_2$—. In other embodiments, $R^8$ is —CH$_2$CH$_2$CH$_2$—. In yet other embodiments, $R^8$ is —CH$_2$CH$_2$—. In further embodiments, $R^8$ is —CH$_2$—.

In some embodiments, $R^{10}$ is —(CH$_2$)$_p$—, where p ranges from 1 to 12. In some embodiments, p ranges from 1 to 6. In other embodiments, p ranges from 1 to 4. In yet other embodiments, p is 1 or 2.

In some embodiments, $R^{10}$ is —(CH$_2$CH$_2$O)$_o$—, —(CH$_2$CH$_2$O)$_o$C(O)—, where o ranges from 1 to 250. In some embodiments, $R^{10}$ is —(CH$_2$CH$_2$O)$_o$—, —(CH$_2$CH$_2$O)$_o$C(O)—, where o ranges from 1 to 100. In some embodiments, $R^{10}$ is —(CH$_2$CH$_2$O)$_o$—, —(CH$_2$CH$_2$O)$_o$C(O)—, where o ranges from 1 to 50. In some embodiments, $R^{10}$ is —(CH$_2$CH$_2$O)$_o$—, —(CH$_2$CH$_2$O)$_o$C(O)—, where o ranges from 1 to 10. In other embodiments, $R^{10}$ is —(CH$_2$CH$_2$O)$_o$—, —(CH$_2$CH$_2$O)$_o$C(O)—, where o ranges from 1 to 6.

In some embodiments, $R^{11}$ is H. In other embodiments, $R^{11}$ is methyl.

In some embodiments, $R^{35}$ is OH and $R^{36}$ is —CH$_2$—, —CH(CH$_3$)— or —C(CH$_3$)$_2$.

Additional Compositions, Mixtures, and Blends

In some embodiments, the compounds of any of Formulas (IA) to (IE) and (IIA) to (IIF) may be mixed with a blocked isocyanate and a chain-extender to generate an electromagnetic-curable resin composition that can be b-staged with electromagnetic radiation, followed by thermal curing to generate a solid polyurethane material (see, for example, U.S. Pat. No. 9,453,142, the disclosure of which is hereby incorporated by reference herein in its entirety). An example of a product of such reaction is illustrated below:

In some embodiments, the compounds of Formula (I) and Formula (II) can be reacted with an isocyanate and an additional chain extender to form a polyurethane containing an additional polymerizable group (see, for example, the components and methods described in U.S. Pat. No. 9,453,142, the disclosure of which is hereby incorporated by reference herein in its entirety).

In some embodiments, the compounds of any of Formulas (IA) to (IE) and (IIA) to (IIF) may be mixed, blended, and/or reacted with a compound having Formula (XIII):

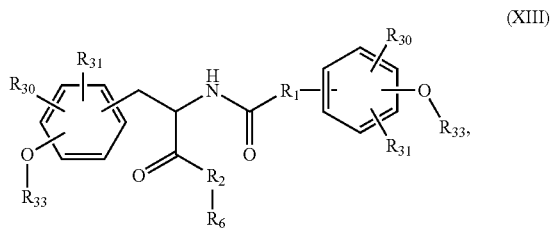

wherein
$R^1$ is a saturated or unsaturated, straight chain or branched alkyl group having between 1 and 12 carbon atoms;
$R^2$ is —O—, —NR$^s$— where $R^s$ is H or a $C_1$-$C_4$ alkyl group, or —S—;
$R^6$ is H or a straight chain or branched alkyl group having up to 18 carbons atoms;
each of $R^{30}$ and $R^{31}$ are independently selected from I or H; and
each $R^{33}$ is independently H, —CN, 4-hydroxybenzene, 3-iodo-4-hydroxybenzene, or 3,5-diiodo-4-hydroxybenzene.

In some embodiments, any blend may comprise a mixture of a compound of Formula (XIII) with any of Formulas (I) through (XII), wherein an amount of the compound of

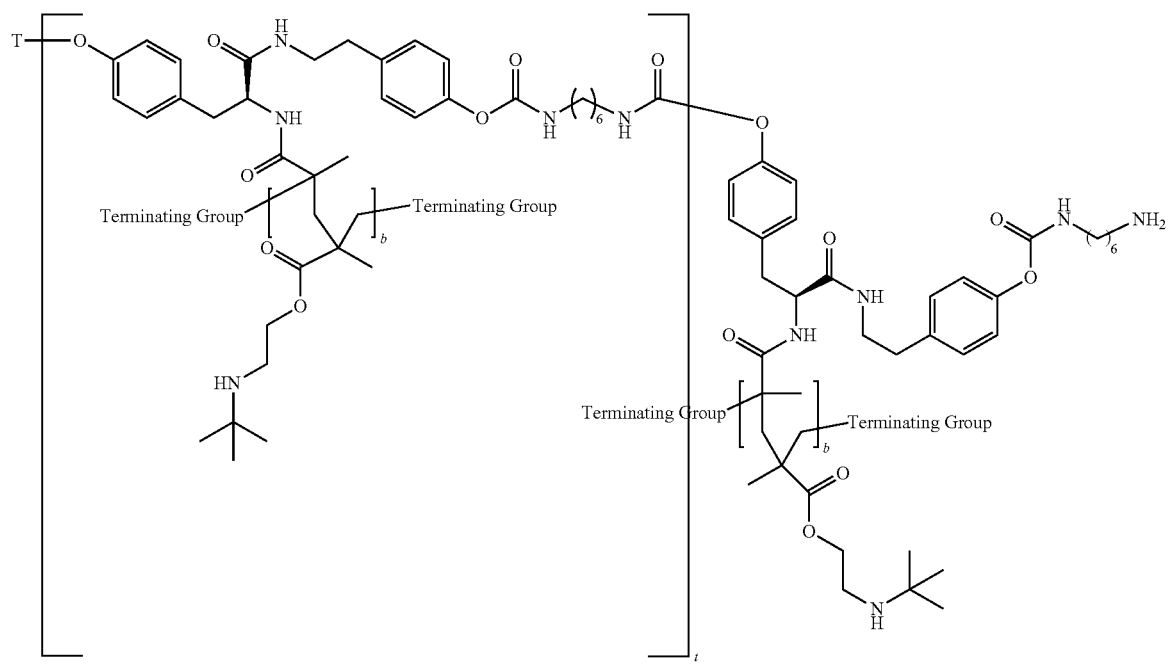

Formula (XIII) in any blend ranges from between about 1% to about 95% by total weight of the blend. In other embodiments, any blend may comprise a mixture of a compound of Formula (XIII) with any of Formulas (I) through (XII), wherein an amount of the compound of Formula (XIII) in any blend ranges from between about 1% to about 85% by total weight of the blend. In yet other embodiments, any blend may comprise a mixture of a compound of Formula (XIII) with any of Formulas (I) through (XII), wherein an amount of the compound of Formula (XIII) in any blend ranges from between about 1% to about 75% by total weight of the blend. In further embodiments, any blend may comprise a mixture of a compound of Formula (XIII) with any of Formulas (I) through (XII), wherein an amount of the compound of Formula (XIII) in any blend ranges from between about 1% to about 65% by total weight of the blend. In yet further embodiments, any blend may comprise a mixture of a compound of Formula (XIII) with any of Formulas (I) through (XII), wherein an amount of the compound of Formula (XIII) in any blend ranges from between about 1% to about 50% by total weight of the blend. In even further embodiments, any blend may comprise a mixture of a compound of Formula (XIII) with any of Formulas (I) through (XII), wherein an amount of the compound of Formula (XIII) in any blend ranges from between about 1% to about 40% by total weight of the blend. In some embodiments, any blend may comprise a mixture of a compound of Formula (XIII) with any of Formulas (I) through (XII), wherein an amount of the compound of Formula (XIII) in any blend ranges from between about 1% to about 30% by total weight of the blend. In other embodiments, any blend may comprise a mixture of a compound of Formula (XIII) with any of Formulas (I) through (XII), wherein an amount of the compound of Formula (XIII) in any blend ranges from between about 1% to about 20% by total weight of the blend. In some embodiments, any blend may comprise a mixture of a compound of Formula (XIII) with any of Formulas (I) through (XII), wherein an amount of the compound of Formula (XIII) in any blend ranges from between about 1% to about 15% by total weight of the blend. In other embodiments, any blend may comprise a mixture of a compound of Formula (XIII) with any of Formulas (I) through (XII), wherein an amount of the compound of Formula (XIII) in any blend ranges from between about 1% to about 10% by total weight of the blend. In some embodiments, any blend may comprise a mixture of a compound of Formula (XIII) with any of Formulas (I) through (XII), wherein an amount of the compound of Formula (XIII) in any blend ranges from between about 1% to about 7.5% by total weight of the blend. In other embodiments, any blend may comprise a mixture of a compound of Formula (XIII) with any of Formulas (I) through (XII), wherein an amount of the compound of Formula (XIII) in any blend ranges from between about 1% to about 5% by total weight of the blend.

In some embodiments, a compound of Formula (XIII) and a compound of any of Formulas (I) to (XII) may be pre-reacted via polycondensation, polyaddition, or copolymerization to generate copolymers of Formula (XIII) with any of formulas (I) to (XII). The resulting product should be a viscous material that has a viscosity suitable for three-dimensional printers, ranging from 0.1 to 500,000 centipoise, most preferably between 1 to 100,000 centipoise. Following pre-reaction, a polymerization initiator (such as those described herein) may be added. Also, an optional thermal catalyst may be added, such as but not limited to dicumyl peroxide, hydrogen peroxide, benzoyl peroxide, and/or cobalt(III) acetylacetate.

In some embodiments, a compound having any of Formulas (I) through (XII), may be mixed with a co-solvent and/or a co-monomer. In some embodiments, the co-solvent and/or co-monomer are selected from the group consisting of N,N-dimethylformamide, dichloromethane, tetrahydrofuran, 2-hydroxyethyl methacrylate, 2-hydroxyethyl acrylate, tert-butylaminoethyl methacrylate, any acrylated or methacrylated derivatives of erythritol such as but not limited to (2R,3S)-2,3-dihydroxybutane-1,4-diyl bis(2-methylacrylate), polycaprolactone diol (average Mn from 200 to 50,000), acrylate- or methacrylate-terminated polycaprolactones such as but not limited to polycaprolactone bismethacrylate, acrylated or methacrylated diols such as 3-hydroxypropyl methacrylate and propylene bismethacrylate, triols, or polyols, as well as any other liquid acrylates and methacrylates similar to the examples listed above.

In some embodiments, any of the compounds set forth in the present disclosure can be reacted together using a one- or two-stage cure. In the first stage, curing is achieved by ultraviolet radiation (UV), cationic, electron beam (EB), laser, peroxide, and/or chemical additive cure. In the second stage (if applicable), curing is achieved by thermal means. In some embodiments, second stage cure is achieved using microwaves (e.g. curing within a microwave oven).

For example, curing of the components of any of the compounds presently disclosed may occur either by first photo-curing the photocurable units followed by a thermal cure to cause the reaction between the other components, such as a diphenol with a blocked isocyanate. Alternatively, there could be a room temperature reaction between the non-photopolymerizable groups to form oligomeric/polymeric structures, such as the reaction between a diphenol and an isocyanate. The room temperature reaction would then be followed by a photo-cure and a thermal cure to complete the reactions.

General Synthetic Methods for Preparing the Compounds of Formulas (IA) and (IB)

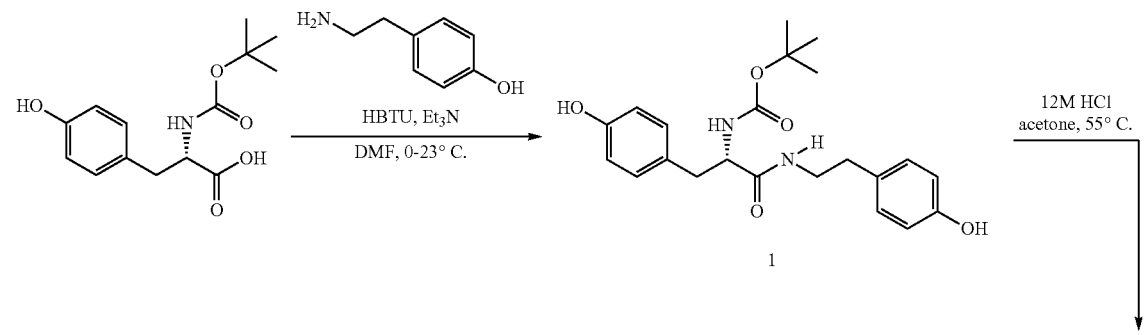

1

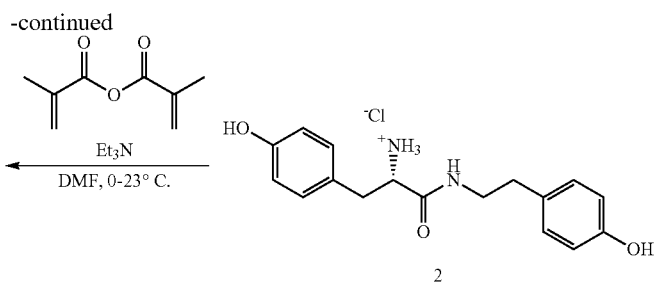

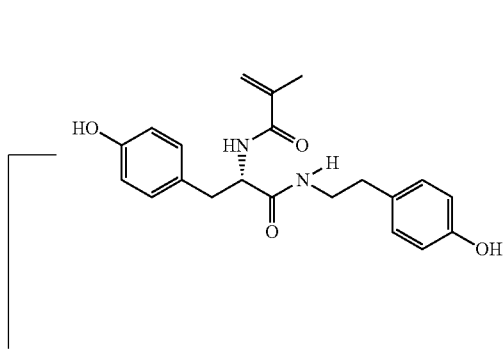

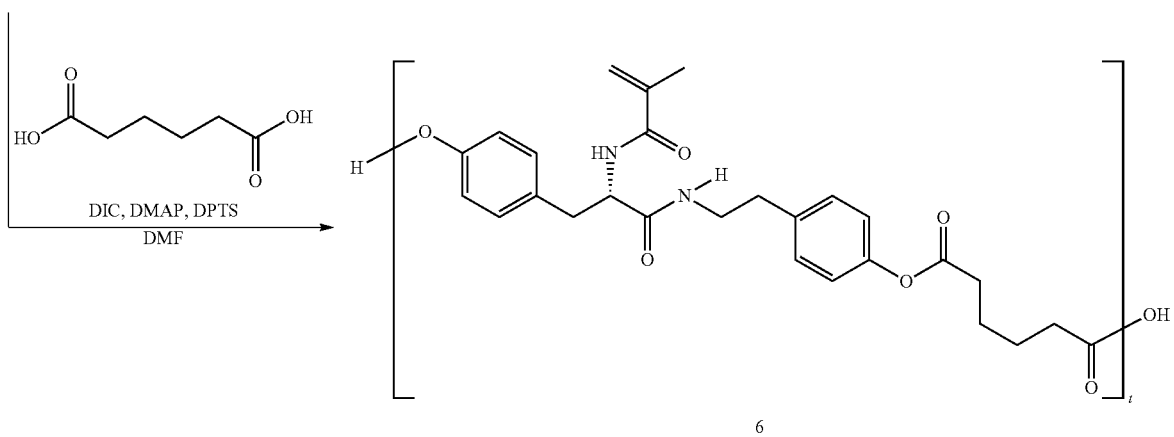

The following examples are non-limiting with regards to synthetic techniques, purifications, or solvents. These synthetic methods include but are not limited to acylations, amide couplings, esterifications, condensations, protections, deprotections, eliminations, and additions. While a protection/deprotection strategy was employed for tyrosine in these examples, the compounds depicted may be synthesized without protection, using the same or similar reaction methods. Generally, 1 can be synthesized by amide coupling of commercial materials, followed by deprotection (2), acylation (3), and polycondensation (6, 24, 25, 26) or polyaddition (22, 23). Typical UV polymerizations use a 405 nm laser and UV lights to induce crosslinking, but other sources and wavelengths as described herein may be used. Similarly, any photo initiator previously described may be used for UV polymerization.

Applications

The resins, reaction products, blends, polymers, compositions, etc. described herein may be utilized in any suitable application. For example, the resins, reaction products, blends, polymers, compositions, etc. may be used as a substrate onto which other materials may be applied. In some embodiments, resins, reaction products, blends, polymers, compositions, etc. may be applied as films onto the surface of another substrate or a laminate may be produced from the resins, reaction products, blends, polymers, compositions, etc. disclosed herein.

In some embodiments, the resins, reaction products, blends, polymers, compositions, etc. disclosed herein may be used in the manufacture of drug delivery systems, capsules, pill-coatings, excipients, medical devices such as but not limited to biodegradable pouches and ophthalmic devices, each of which may be coated with or impregnated with an antibacterial agent or other active pharmaceutical ingredient.

Biodegradation Studies

The biodegradation of two crosslinked polymer samples (see for example, the compounds of Examples 7 and 8, herein) was monitored by sample mass loss according to the following procedure. The dried polymer sample was weighed, transferred into a sealed 250 mL PBS (phosphate-buffered saline) solution (titrated at pH 7.40), then heated to 37° C. (+/−3° C.) for 7 days. The sample was removed, washed with deionized $H_2O$, patted dry, then further dried in a vacuum oven at 100° C. for 6 hours. The sample was weighed, and the sample's PBS solution pH was measured; the sample's PBS solution was replaced with fresh PBS solution whenever the pH reached 7.36. The sample was then returned to the PBS solution, and the process repeated, with measurements taken every 7 days.

The PBS solution at 37° C. mimics the pH, temperature, and ionic strength of human plasma; thus, observed mass loss of the polymer sample in PBS solution is indicative of effective biodegradation within the human body. Accordingly, analysis of several crosslinked samples based on Formulas (VIIA) and (VIIIA) showed steady mass loss over several weeks, which suggests that these materials are biodegradable within the human body. Similarly, blends of formulas (VIIA) or (VIIIA) with co-monomers such as HEMA lose mass over time, appearing to be biodegradable as well.

EXAMPLES

Example 1—Tert-butyl N-[(1S)-2-(4-hydroxyphenyl)-1-{[2-(4-hydroxyphenyl)ethyl]carbamoyl}ethyl]carbamate (1)

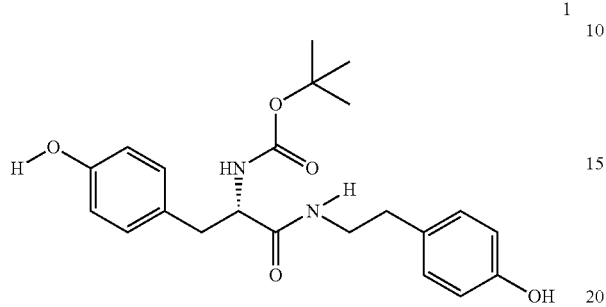

N-Boc-L-Tyrosine (28.1 g, 1 equivalent) was charged to a 1-Liter flask fitted with a mechanical stirrer, followed by subsequent addition of DMF (333 mL) and Et$_3$N (13.9 mL, 1 equivalent). The resulting solution was cooled to 0° C. with an ice bath and allowed to stir for 30 minutes. HBTU (41.7 g, 1.1 equivalents) was added and the solution was stirred at 0° C. for exactly 5 minutes, at which point tyramine (16.5 g, 1.2 equivalents) was added in one portion. An additional amount of Et$_3$N (18.1 mL, 1.3 equivalents) was added, and the brown solution stirred overnight (16 h) at room temperature. The reaction was poured into an immiscible mixture of brine (700 mL) and EtOAc (450 mL), and the biphasic mixture was mechanically stirred for 15 minutes. The layers were separated, and the aqueous layer was backwashed once with EtOAc (100 mL). The combined organics were washed three times with 0.66 M HCl (170 mL portions), three times with 5% NaHCO$_3$ solution (110 mL portions), once with deionized H$_2$O (100 mL), and once with brine (100 mL). The organics were dried over Na$_2$SO$_4$, filtered, and concentrated via rotary evaporation to afford a brown oil. The oil was further dried in a vacuum oven for 16 hours at 40° C. to give 1 as a foamy tan solid (38.66 g, 97%).

Example 2—(1S)-2-(4-hydroxyphenyl)-1-{[2-(4-hydroxyphenyl)ethyl]carbamoyl}ethan-1-aminium Chloride (2)

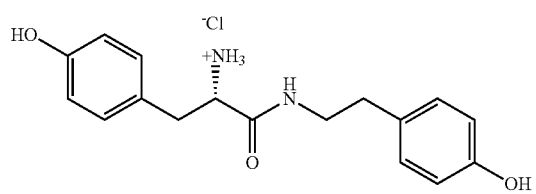

Compound 1 (38.6 g, 1 equivalent) was charged to a 1-Liter flask fitted with a mechanical stirrer, followed by subsequent addition of acetone (386 mL). Concentrated HCl (12 M, 16.1 mL, 2 equivalents) was then added with stirring, and the resulting solution was heated to 50° C. The reaction was left to stir at this temperature for 5 hours, with visible precipitate forming after 1.5 hours. The reaction was cooled to room temperature, deionized H$_2$O (150 mL) was added, and the acetone was subsequently removed by rotary evaporation. The aqueous solution was washed four times with EtOAc (75 mL portions), and the combined organics were discarded. The aqueous layer was then concentrated via rotary evaporation, and further dried in a vacuum oven for 16 hours at 40° C. to give 2 as a foamy light brown solid (31.74 g, 98%).

Example 3—Preparation of Tyrosamide Methacrylamide (3)

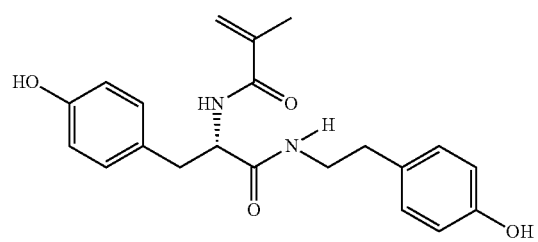 [SMILES: C=C(C)C(=O)N[C@@H](Cc1ccc(O)cc1)C(=O)NCCc1ccc(O)cc1]

Compound 2 (16.84 g, 1 equivalent) was charged to a 500-mL flask with a magnetic stir bar, and the flask contents purged with an N$_2$ stream for 10 minutes. DMF (167 mL) and Et$_3$N (14.6 mL, 2.1 equivalents) were added successively, and the septum-sealed reaction flask was cooled to 0° C. via an ice bath. After stirring at 0° C. for 25 minutes, methacrylic anhydride (8.2 mL, 1.1 equivalents) was added slowly via syringe over 5 minutes. The reaction was left to stir for 16 hours, slowly warming to room temperature during that time. The reaction mixture was poured into a mixture of ice water (350 mL) and EtOAc (250 mL) and was then stirred for 15 minutes. The resulting bilayer was separated, and the organic layer was subsequently washed three times with 5% NaHCO$_3$ solution (100 mL portions), twice with 0.66 M HCl (100 mL portions), and once with brine (50 mL). The organic layer was then dried over Na$_2$SO$_4$, filtered, and concentrated via rotary evaporation. Further drying in the vacuum oven for 16 hours at 23° C. gave 3 as a light tan solid (12.74 g, 69%). 1H NMR (600 MHz, DMSO-d6) δ 9.16 (s, 2H), 7.95 (d, J=2.7 Hz, 1H), 7.79 (d, J=8.5 Hz, 1H), 7.01 (d, J=8.5 Hz, 2H), 6.98 (d, J=8.5 Hz, 2H), 6.68-6.65 (m, 2H), 6.64-6.61 (m, 2H), 5.61 (t, J=1.2 Hz, 1H), 5.30 (t, J=1.6 Hz, 1H), 4.39 (ddd, J=9.9, 8.4, 4.7 Hz, 1H), 3.30-3.22 (m, 1H), 3.17 (dtd, J=13.0, 7.3, 5.4 Hz, 1H), 2.84 (dd, J=13.7, 4.7 Hz, 1H), 2.78-2.73 (m, 1H), 2.56 (td, J=7.3, 1.7 Hz, 1H), 1.79 (t, J=1.2 Hz, 3H); 13C NMR (151 MHz, DMSO-d6) δ171.16, 167.28, 155.71, 155.65, 139.58, 130.08, 129.53, 129.45, 128.30, 119.46, 115.09, 114.82, 54.85, 40.60, 36.63, 34.30, 18.60.

Example 4—Preparation of Poly(TyMA) (4)

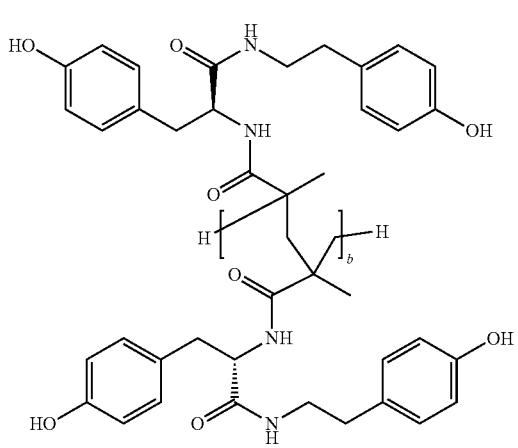

Compound 3 (253 mg, 86 wt %) was charged to a 20 mL vial and solvated with MeOH (36 μL, 10 wt %) and Irgacure 2022 (12 mg, 4 wt %). The resulting solution was then cured by exposure to a 405 nm UV laser for 2 minutes. The material formed a light brown solid. The material was post-cured in a UV oven equipped with 365 nm light bulbs for 16 hours to afford 4.

Example 5—Preparation of TyMA/HEMA Copolymer (5)

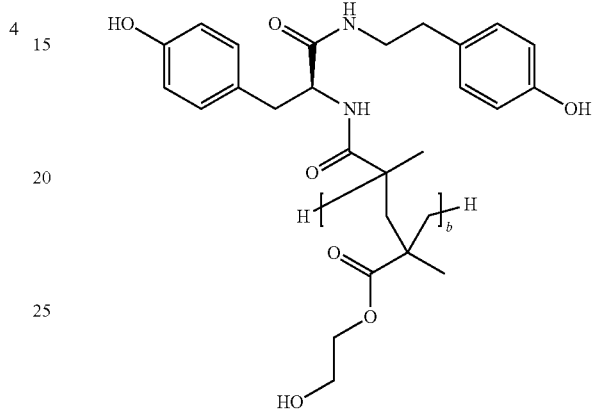

Compound 3 (193 mg, 44 wt %) was charged to a 20 mL vial and solvated with (Hydroxyethyl)methacrylate (HEMA) (215 mg, 49 wt %) and Irgacure 2022 (31 mg, 7 wt %) (this particular photoinitiator is a 20/80 weight blend of phenyl bis(2,4,6-trimethyl benzoyl) phosphine oxide and 2-hydroxy-2-methyl-1-phenyl-1-propanone). The resulting solution was then cured by exposure to a 405 nm UV laser for 2 minutes. The material formed a transparent, brown, glass-like solid. The material was post-cured in a UV oven equipped with 365 nm light bulbs for 16 hours to afford 5.

Example 6—Preparation of TyMA-PA (6)

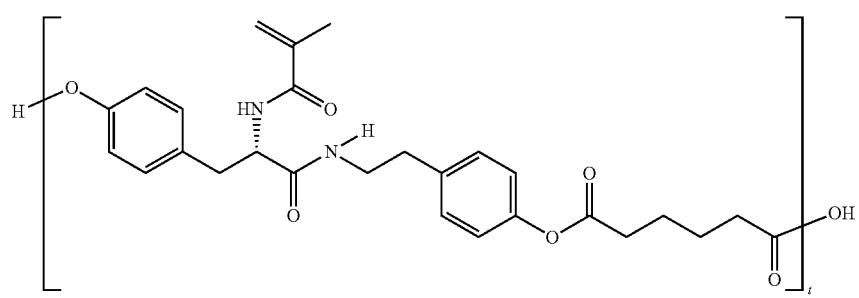

Compound 3 (11.93 g, 1 equivalent) was charged to a 1-neck 500-mL flask with a magnetic stir bar. DMAP (989 mg, 0.25 equivalents), 4-(dimethylamino) pyridinium 4-toluene sulfonate (953 mg, 0.1 equivalents), adipic acid (4.73 g, 1 equivalent), and DMF (105 mL) were sequentially added to the reaction flask, and the contents allowed to stir at room temperature for 30 minutes. The reaction flask was placed in a room temperature water bath, and diisopropyl-carbodiimide (15.0 mL, 3 equivalents) was then added via syringe with stirring. The resulting solution was left to stir for 24 hours at room temperature, with visible precipitate forming after several hours. Upon completion, iPrOH (50 mL) was added to the mixture, and the resulting homogeneous solution was poured into ice water (350 mL). The gummy precipitate that formed was stirred for an hour, then was left to settle overnight without stirring, slowly warming to room temperature. The majority of the liquid was carefully decanted into a vacuum filtration apparatus to avoid clogging the filter, and the remainder of the thick slurry was then poured into the vacuum filter apparatus. The gummy solids were thoroughly ground on the filter with a glass stir rod and washed three times with iPrOH (100 mL portions). The resulting off-white powder was then dried in a vacuum oven for 4 hours at 40° C. to give 6 as a fine, off-white powder (11.62 g, 72%). 1H NMR (600 MHz, DMSO-d6) δ 8.09 (t, J=3.9 Hz, 1H), 7.93 (dt, J=8.6, 2.4 Hz, 1H), 7.29-7.21 (m, 4H), 7.04-6.98 (m, 4H), 5.61 (s, 1H), 5.30 (s, 1H), 4.48 (td, J=9.2, 8.6, 4.5 Hz, 1H), 3.38-3.22 (m, 2H), 2.99-2.84 (m, 2H), 2.71 (q, J=8.6, 7.3 Hz, 2H), 2.65-2.53 (m, 4H), 1.78 (s, 3H), 1.75-1.57 (m, 4H); 13C NMR (151 MHz, DMSO) δ 171.66, 171.59, 171.06, 167.40, 148.89, 148.82, 139.49, 136.88, 135.80, 130.08, 129.63, 121.54, 121.26, 119.50, 54.42, 40.17, 36.64, 34.37, 33.12, 23.71, 18.58.

Example 7—Preparation of Poly(TyMA-PA) (7)

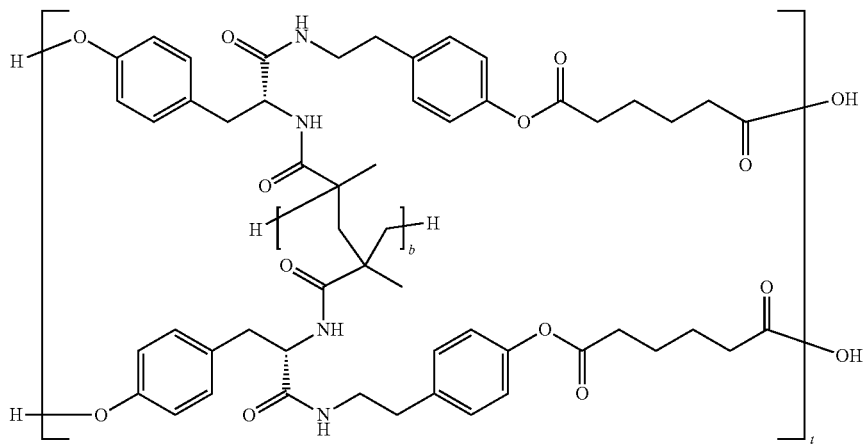

Compound 6 (281 mg, 60 wt %) was charged to a 20 mL vial and solvated with DMF (171 mg, 36 wt %) and Irgacure 2022 (19 mg, 4 wt %). The resulting mixture was gently heated to expedite the solubility and allowed to cool back to room temperature. The resulting solution was then cured by exposure to a 405 nm UV laser for 2 minutes. The material formed a transparent, pale yellow, glass-like solid. The material was post-cured in a UV oven equipped with 365 nm light bulbs for 16 hours to afford 7.

Example 8—Preparation of TyMA-PA/HEMA Copolymer (8)

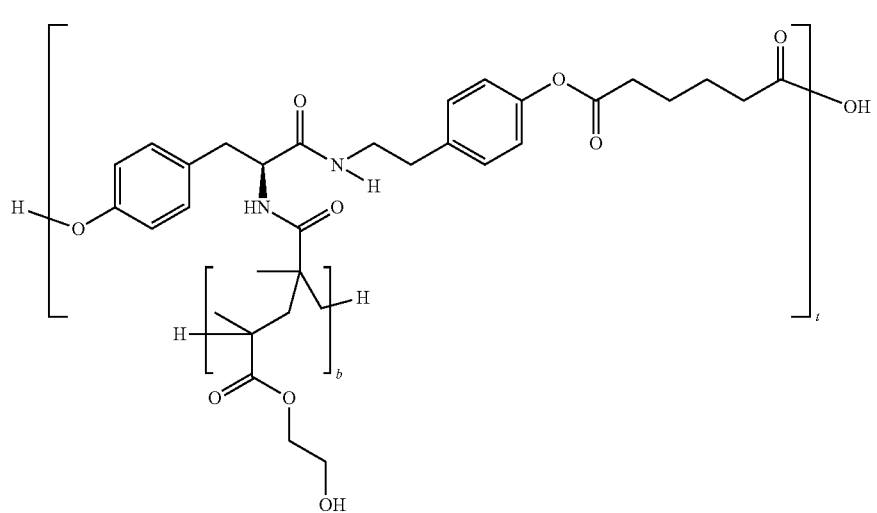

Compound 6 (256 mg, 48 wt %) was charged to a 20 mL vial and solvated with HEMA (252 mg, 48 wt %) and Irgacure 2022 (22 mg, 4 wt %). The resulting mixture was gently heated to expedite the solubility and allowed to cool back to room temperature. The resulting solution was then cured by exposure to a 405 nm UV laser for 2 minutes. The material formed a transparent, light brown, glass-like solid. The material was post-cured in a UV oven equipped with 365 nm light bulbs for 16 hours to afford 8.

Example 9—Methyl (2S)-3-(4-hydroxyphenyl)-2-[3-(4-hydroxyphenyl)propanamido]propanoate (9)

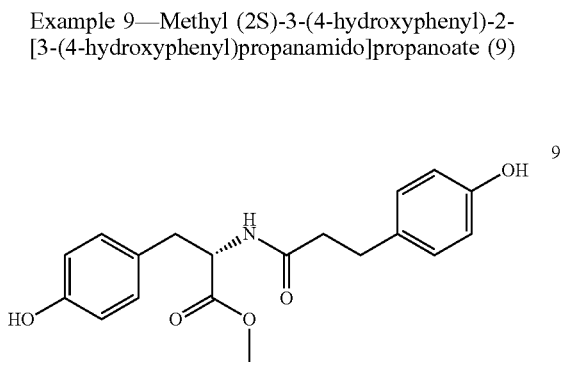

3-(4-hydroxyphenyl)propanoic acid (16.62 g, 1 equivalent) was charged to a 1-Liter flask fitted with a mechanical stirrer and purged with $N_2$ for 10 minutes. DMF (333 mL) and $Et_3N$ (45.9 mL, 3.3 equivalents) were added successively, and the resulting solution was cooled to 0° C. with an ice bath and allowed to stir for 30 minutes. HBTU (41.7 g, 1.1 equivalents) was added and the solution was stirred at 0° C. for 30 minutes, at which point L-tyrosine methyl ester hydrochloride (25.5 g, 1.1 equivalents) was added in one portion. The suspension was stirred overnight (16 h), slowly warming to room temperature over that time. The reaction was poured into brine (660 mL) and was mechanically stirred for 15 minutes. The suspension was directly filtered, the solids washed three times with deionized $H_2O$ (100 mL portions), and then further dried in a vacuum oven for 16 hours at 40° C. to give 9 as a white powder (18.63 g, 54%).

Example 10—(2S)-3-(4-hydroxyphenyl)-2-[3-(4-hydroxyphenyl)propanamido]propanoic Acid (10)

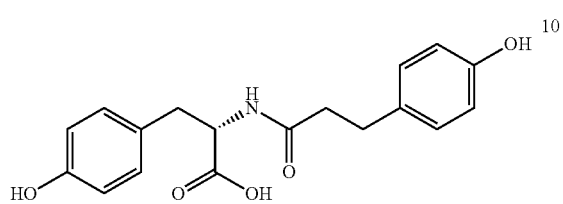 [SMILES: O=C(CCc1ccc(O)cc1)N[C@@H](Cc1ccc(O)cc1)C(=O)O]

Compound 9 (14.76 g, 1 equivalent) was charged to a 100-mL flask with a magnetic stir bar. $H_2O$ (22 mL) and THF (22 mL) were added successively, followed by the addition of KOH (7.96 g, 3.3 equivalents). The reaction mixture began to exotherm and was stirred for 2 hours. The THF was removed by vacuum distillation at 65° C./250 Torr and the remaining aqueous mixture was acidified to pH 1 with 12 M HCl. EtOAc (250 mL) was added, and the layers were separated. The organic layer was additionally washed with 1 M HCl (100 mL) and brine (50 mL), then the organics were dried over $Na_2SO_4$. Subsequent filtration, concentration via rotary evaporation, and additional drying in a vacuum oven for 4 hours at 40° C. gave 10 as a beige solid (10.54 g, 74%).

Example 11—Preparation of TyHE Monomer (11)

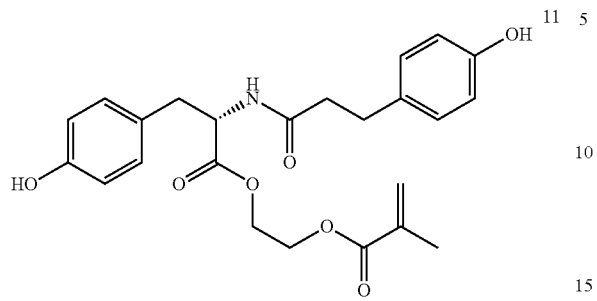

Compound 10 (9.8 g, 1 equivalent) was charged to a 500-mL flask with a magnetic stir bar. DCM (150 mL), DMAP (364 mg, 0.1 equivalents), and HEMA (5.1 mL, 1.4 equivalents) were added sequentially and stirred for 15 minutes, at which point diisopropylcarbodiimide (5.1 mL, 1.1 equivalents) was added. The solution was stirred for 4 days, with precipitate forming after 4 hours. The reaction was filtered to remove urea byproduct (solids washed with 20 mL of EtOAc), and the filtrate was poured into brine (350 mL). Additional EtOAc was added (200 mL), and the layers separated. The organic layer was additionally washed twice with 1 M HCl (50 mL portions), twice with 5% $NaHCO_3$ solution (50 mL portions), and once with brine (50 mL). The organics were dried over $Na_2SO_4$, filtered, and concentrated via rotary evaporation to give 11 as a yellow oil (8.25 g, 63%). 1H NMR (600 MHz, DMSO-d6) δ 9.18 (s, 2H), 8.23 (d, J=7.7 Hz, 1H), 6.96-6.91 (m, 4H), 6.66-6.61 (m, 4H), 6.03 (dt, J=1.9, 0.9 Hz, 1H), 5.69 (t, J=1.6 Hz, 1H), 4.38 (ddd, J=9.0, 7.7, 5.7 Hz, 1H), 4.27-4.23 (m, 4H), 2.86 (dd, J=13.9, 5.7 Hz, 1H), 2.77-2.73 (m, 1H), 2.60 (t, J=7.9 Hz, 2H), 2.31-2.27 (m, 2H), 1.87 (t, J=1.3 Hz, 3H); 13C NMR (151 MHz, DMSO-d6) δ 171.63, 166.66, 166.36, 156.02, 155.43, 135.94, 135.56, 131.21, 129.94, 128.96, 127.10, 126.15, 125.69, 62.34, 62.25, 53.90, 37.05, 35.97, 30.14, 17.92.

Example 12—Preparation of Poly(TyHE) (12)

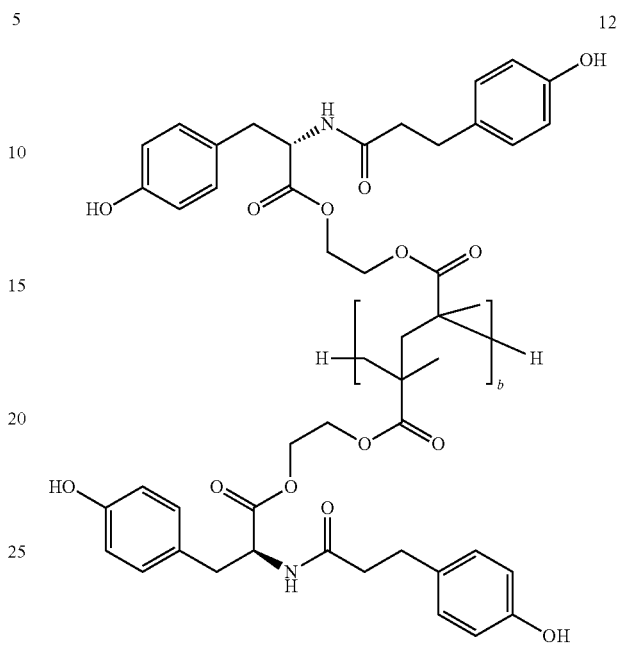

Compound 11 (461 mg, 95 wt %) was charged to a 20-mL vial and was thoroughly mixed with Irgacure 2022 (22 mg, 5 wt %). The resulting mixture was then cured by exposure to a 405 nm UV laser for 2 minutes. The material formed a transparent, brown, glass-like solid. The material was post-cured in a UV oven equipped with 365 nm light bulbs for 16 hours to afford 12.

Example 13—Preparation of TyHE-PA (13)

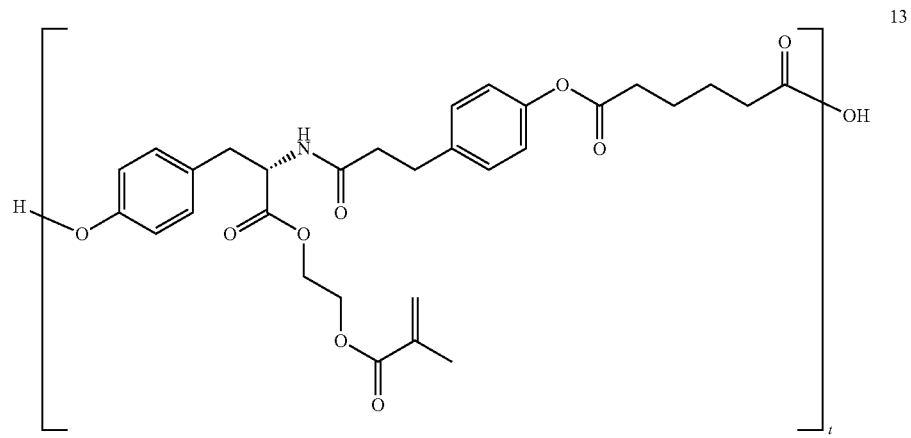

Compound 11 (7.71 g, 1 equivalent) was charged to a 250-mL flask with a magnetic stir bar. DMAP (533 mg, 0.25 equivalents), 4-(dimethylamino) pyridinium 4-toluene sulfonate (514 mg, 0.1 equivalents), adipic acid (2.55 g, 1 equivalent), and DCM (70 mL) were sequentially added to the reaction flask, and the contents allowed to stir at room temperature for 30 minutes. Diisopropylcarbodiimide (8.1 mL, 3 equivalents) was then added via syringe with stirring. The resulting solution was left to stir for 24 hours at room temperature, with visible precipitate forming after several hours. Upon completion, iPrOH (120 mL) was added to the mixture, and the resulting homogeneous solution was concentrated via rotary evaporation to remove DCM. A precipitate formed during concentration, which was filtered and washed three times with iPrOH (20 mL portions). The solids were dried for 4 hours at 40° C. in a vacuum oven to afford 13 (3.42 g). The mother liquor was further concentrated via rotary evaporation to afford additional precipitate, which was filtered, washed, and dried as previously described to afford a second crop of 13 (3.74 g; 7.16 g total, 72% total yield). 1H NMR (600 MHz, DMSO-d6) δ 7.36-7.13 (m, 4H), 7.08-6.89 (m, 4H), 6.01-5.99 (m, 1H), 5.70-5.66 (m, 1H), 4.30-4.29 (m, 1H), 4.28-4.26 (m, 4H), 2.98-2.87 (m, 2H), 2.86-2.82 (m, 2H), 2.67-2.53 (m, 4H), 2.40-2.27 (m, 2H), 1.86 (s, 3H), 1.76-1.57 (m, 4H); 13C NMR (151 MHz, DMSO-d6) δ 172.58, 172.02, 171.66, 171.12, 166.36, 148.85, 148.77, 148.69, 137.88, 137.70, 135.58, 129.33, 129.18, 126.09, 121.55, 62.42, 61.80, 61.67, 34.98, 34.81, 33.11, 33.00, 29.57, 29.49, 23.71, 17.90.

Example 14—Preparation of Poly(TyHE-PA) (14)

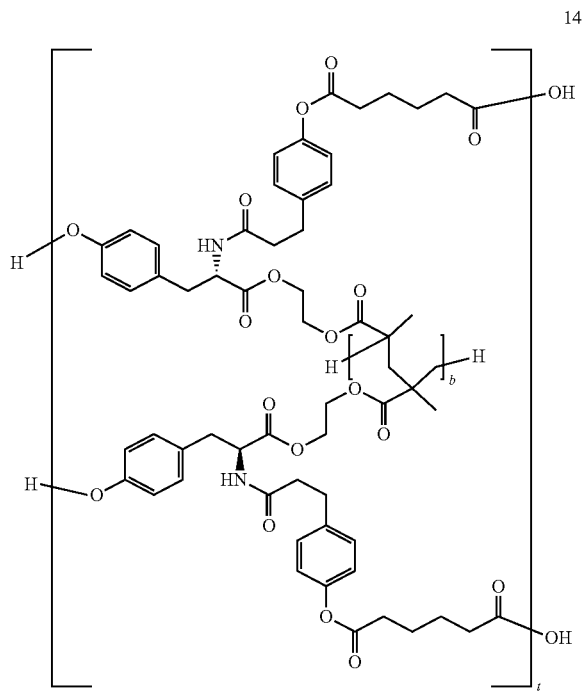

14

Compound 13 (263 mg, 47 wt %) was charged to a 20 mL vial and solvated with DMF (275 mg, 50 wt %) and Irgacure 2022 (16 mg, 3 wt %). The resulting mixture was gently heated to expedite the solubility and allowed to cool back to room temperature. The resulting solution was then cured by exposure to a 405 nm UV laser for 2 minutes. The material formed a rubbery, pale yellow solid. The material was post-cured in a UV oven equipped with 365 nm light bulbs for 16 hours to afford 14.

Example 15—2-(((4-nitrophenoxy)carbonyl)oxy)ethyl methacrylate (15)

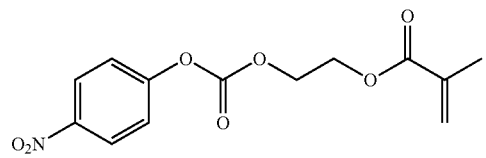

15

HEMA (12.1 mL, 1 equivalent) was charged to a 500-mL flask with a magnetic stir bar. 2-MeTHF (200 mL) and Et₃N (16.7 mL, 1.2 equivalents) were added sequentially and the solution was stirred for 15 minutes, at which point 4-nitrophenyl chloroformate (20.2 g, 1.1 equivalents) was added. The suspension was stirred for 24 hours, slowly turning from colorless to bright yellow. The reaction was diluted with EtOAc (50 mL) and 1 M HCl (150 mL), and the layers were separated. The organic layer was additionally washed three times with 1 M HCl (100 mL portions), once with deionized H₂O (50 mL), and once with brine (50 mL). The organics were dried over Na₂SO₄, filtered, and concentrated to give 15 as a yellow oil (28.53 g, 97%), which was used directly in the next step without further purification.

Example 16—Preparation of TyHC Monomer (16)

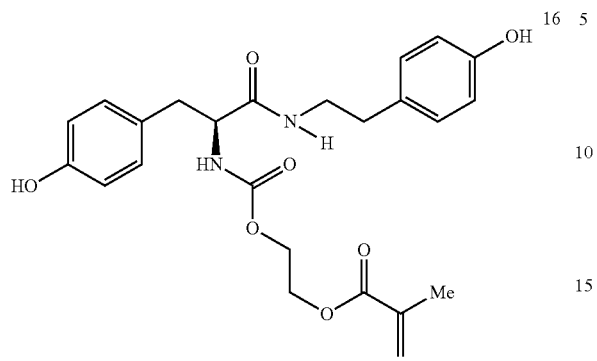

Compound 2 (12.8 g, 1 equivalent) was charged to a 250-mL flask with a magnetic stir bar. DMF (76 mL) and Et$_3$N (13.2 mL, 2.5 equivalents) were added sequentially and the solution was stirred for 15 minutes, at which point the product from Example 15 (13.5 g, 1.2 equivalents) was added. The brown/yellow suspension was stirred for 72 hours and was then poured into brine (300 mL) and EtOAc (200 mL). The layers were separated, and the organic layer was additionally washed three times with 1 M HCl (100 mL portions), once with deionized H$_2$O (50 mL), and once with brine (50 mL). The organics were dried over Na$_2$SO$_4$, filtered, and concentrated via rotary evaporation to give 16 as a brown semi-solid, which was used directly in the next step without further purification. 1H NMR (600 MHz, DMSO-d6) δ 9.14 (s, 2H), 8.14-8.08 (m, 1H), 7.93 (t, J=5.6 Hz, 1H), 7.04-6.59 (m, 8H), 6.01-6.00 (m, 1H), 5.67 (t, J=1.7 Hz, 1H), 4.47-4.37 (m, 1H), 4.23-4.08 (m, 4H), 3.26-3.11 (m, 2H), 2.78-2.72 (m, 1H), 2.59 (dd, J=13.9, 10.1 Hz, 1H), 2.54 (t, J=7.5 Hz, 2H), 1.85 (s, 3H); 13C NMR (151 MHz, DMSO-d6) δ 171.32, 166.44, 164.05, 155.73, 155.62, 135.62, 130.02, 129.50, 129.41, 126.20, 126.05, 115.82, 115.05, 62.98, 61.76, 56.62, 40.56, 36.78, 34.27, 17.93.

Example 17—Preparation of Poly(TyHC) (17)

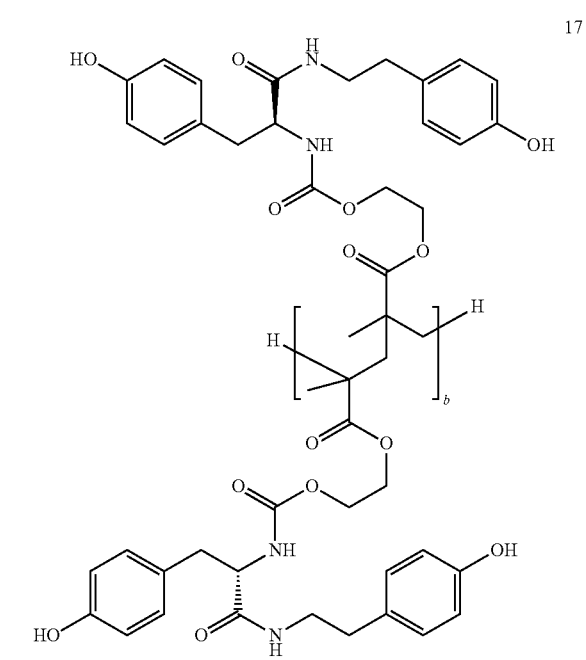

Compound 16 (90 mg, 91 wt %) was charged to a 20-mL vial and was thoroughly mixed with Irgacure 2022 (9 mg, 9 wt %). The resulting mixture was then cured by exposure to a 405 nm UV laser for 2 minutes. The material formed a transparent, pale yellow solid. The material was post-cured in a UV oven equipped with 365 nm light bulbs for 16 hours to afford 17.

Example 18—Preparation of TyHC-PA (18)

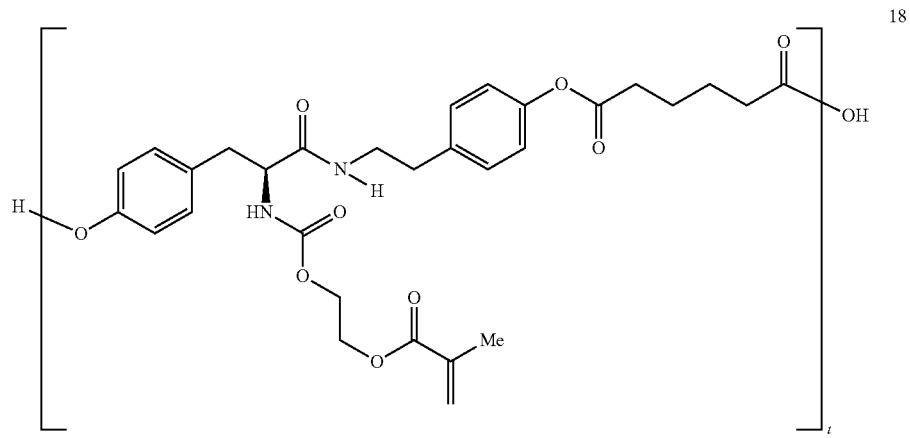

Compound 16 (17.01 g, 1 equivalent) was charged to a 250-mL flask with a magnetic stir bar. DMAP (1.14 g, 0.25 equivalents), 4-(dimethylamino) pyridinium 4-toluene sulfonate (1.10 g, 0.1 equivalent), adipic acid (5.44 g, 1 equivalent), and DCM (75 mL) were sequentially added to the reaction flask, and the contents stirred at room temperature for 30 minutes. Diisopropylcarbodiimide (17.3 mL, 3 equivalents) was then added via syringe with stirring. The resulting solution was left to stir for 24 hours at room temperature, with visible precipitate forming after several hours. Upon completion, the reaction was filtered, and the solids were washed with DCM (50 mL). The filtrate was concentrated via rotary evaporation and suspended in EtOAc (150 mL). The precipitate was filtered and subsequently triturated with iPrOH (150 mL) for 4 hours. The solids were filtered, washed with iPrOH (100 mL), and dried for 6 hours at 40° C. in a vacuum oven to afford 18 (4.13 g, 19%) as a light brown solid. 1H NMR (600 MHz, DMSO-d6) δ 8.10 (t, J=5.2 Hz, 1H), 7.49 (dd, J=8.1, 2.8 Hz, 1H), 7.26 (dd, J=24.2, 8.2 Hz, 4H), 7.02 (dd, J=13.8, 7.9 Hz, 4H), 6.00 (s, 1H), 5.66 (s, 1H), 4.52-4.02 (m, 5H), 3.33-3.21 (m, 2H), 2.88 (d, J=8.5 Hz, 1H), 2.77-2.66 (m, 3H), 2.65-2.54 (m, 4H), 1.85 (s, 3H), 1.77-1.56 (m, 4H); 13C NMR (151 MHz, DMSO-d6) δ 172.21, 171.67, 171.63, 171.27, 166.43, 148.94, 148.84, 136.89, 135.70, 135.63, 130.09, 129.64, 126.04, 121.55, 121.28, 62.97, 61.81, 56.27, 40.17, 36.82, 34.38, 33.46, 25.49, 23.87, 21.61, 17.91.

Example 19—Preparation of Poly(TyHC-PA) (19)

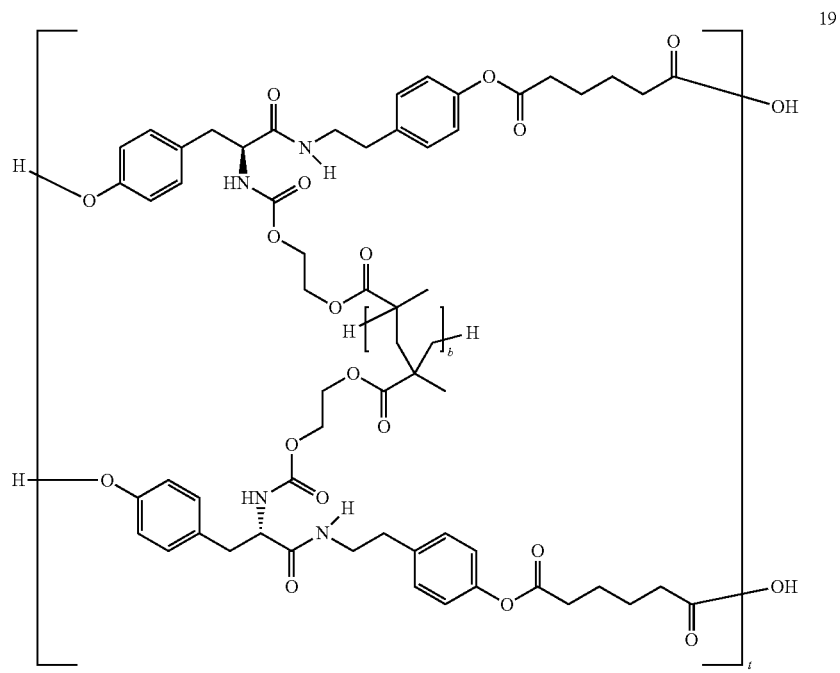

Compound 18 (338 mg, 48 wt %) was charged to a 20 mL vial and solvated with DMF (346 mg, 49 wt %) and Irgacure 2022 (25 mg, 3 wt %). The resulting mixture was gently heated to expedite the solubility and allowed to cool back to room temperature. The resulting solution was then cured by exposure to a 405 nm UV laser for 2 minutes. The material formed a transparent, light brown, glass-like solid. The material was post-cured in a UV oven equipped with 365 nm light bulbs for 16 hours to afford 19.

Example 20—Preparation of TyHE-PA/TyMA-PA Copolymer (20)

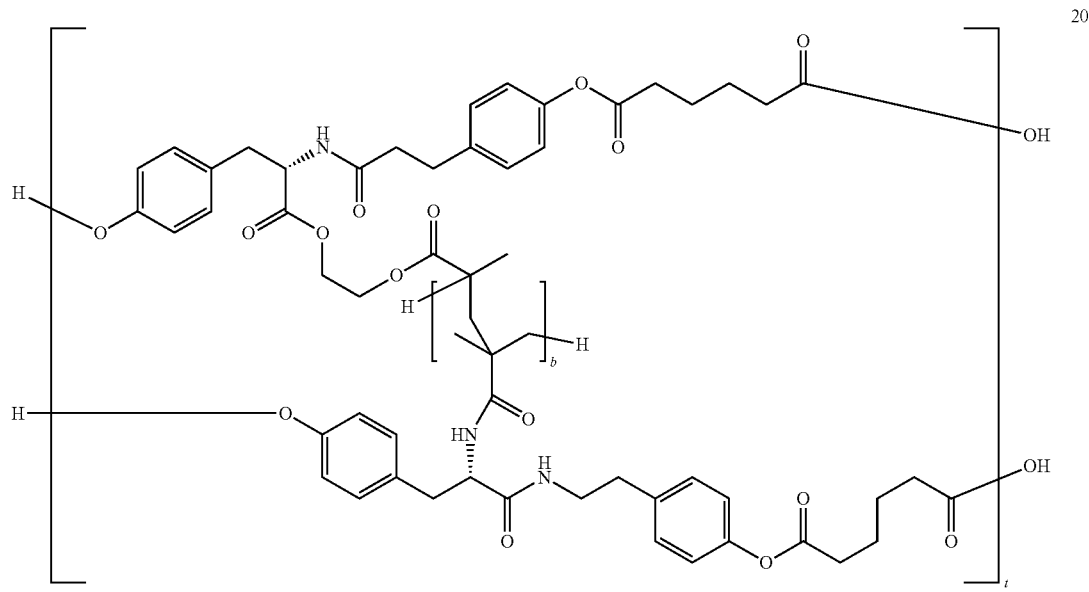

Compound 13 (222 mg, 20 wt %) and Compound 6 (225 mg, 20 wt %) were charged to a 20 mL vial and solvated with DMF (666 mg, 58 wt %) and Irgacure 2022 (20 mg, 2 wt %). The resulting mixture was gently heated to expedite solubility and allowed to cool back to room temperature. The resulting solution was then cured by exposure to a 405 nm UV laser for 2 minutes. The material formed a rubbery, pale yellow solid. The material was post-cured in a UV oven equipped with 365 nm light bulbs for 16 hours to afford 20.

Example 21—Preparation of TyMA-PA/HEMA Copolymer Via 3-D Printing (21)

Compound 6 (30.1 wt %), HEMA (67.1 wt %), and Irgacure 2022 (2.8 wt %) were combined and heated up to 70° C. with mechanical stirring for 30 minutes. The homogeneous resin (viscosity=301 cP without catalyst) was then poured into the resin reservoir of a MuVe 3D DLP printer. The printer software was set to print 3 rectangular bars (40 mm×19.5 mm×15 mm) with support pins (4 pins per bar, 9.5 mm height) attached along the length of the 40 mm edge, with the following specifications: 8 burn-in layers of 50 μM thickness with 50 second cure time; 238 normal layers of 100 μM thickness with 50 second cure time (246 layers total). Upon completion, the rectangular bars were removed from the build plate, rinsed with iPrOH, patted dry, then post-cured in a UV oven equipped with 365 nm light bulbs for 16 hours to afford 21.

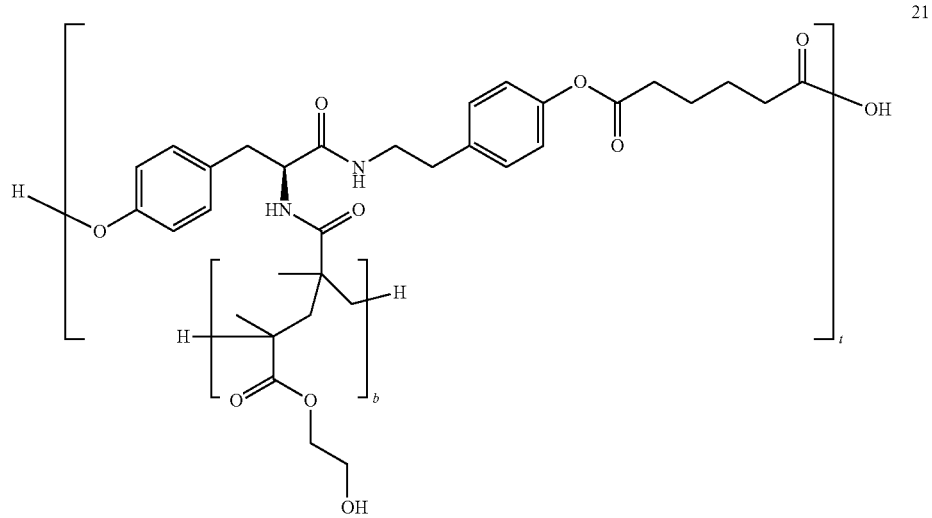

Example 22—Preparation of TyMA-PIC (22)

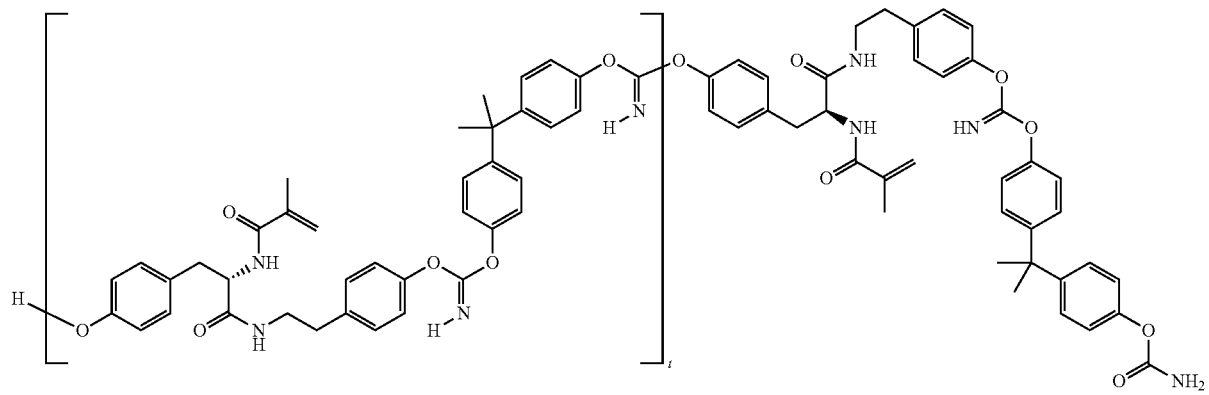

Compound 3 (1.00 g, 1 equivalent) was charged to a 50-mL flask with a magnetic stir bar, followed by addition of $K_2CO_3$ (751 mg, 2 equivalents). THF (11 mL) and $H_2O$ (2 mL) were sequentially added to the reaction flask, and the contents were stirred at room temperature for 30 minutes until homogeneous. 4,4'-(propane-2,2-diyl)bis(cyanatobenzene) (trade name BADCy, 756 mg, 1 equivalent) was then added in one portion, and the resulting solution was left to stir for 20 hours at room temperature. Upon completion (determined by disappearance of BADCy by IR), the reaction was concentrated via rotary evaporation and suspended in $H_2O$ (50 mL). The resulting off-white precipitate was triturated in $H_2O$ for 1 hour, then filtered and dried for 16 hours at 50° C. in a vacuum oven to afford 22 (1.71 g, 98%) as an off-white solid. The product was characterized by IR analysis, specifically by the appearance of the carbonimidate peak (C=N, 1672.4 $cm^{-1}$).

Example 23—Preparation of TyMA-PU (23)

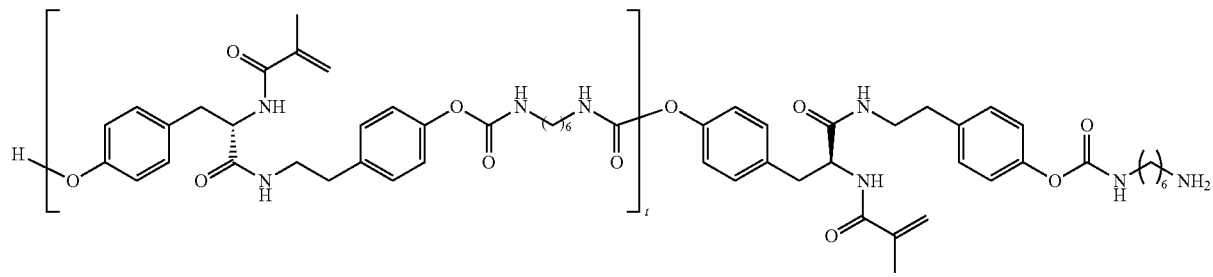

Compound 3 (1.00 g, 1 equivalent) was charged to a 50-mL flask with a magnetic stir bar, followed by addition of $K_2CO_3$ (751 mg, 2 equivalents). THF (11 mL) and $H_2O$ (2 mL) were sequentially added to the reaction flask, and the contents were stirred at room temperature for 30 minutes until homogeneous. 1,6-diisocyanatohexane (aka HDI, 436 µL, 1 equivalent) was then added via syringe in one portion, and the resulting solution was left to stir for 20 hours at room temperature (precipitate was observed). Upon completion (determined by disappearance of HDI by IR), the reaction was concentrated via rotary evaporation and suspended in an aqueous 0.66 M HCl solution (50 mL). The resulting light orange precipitate was triturated in the 0.66 M HCl solution for 1 hour, then filtered, washed with $H_2O$, and dried for 16 hours at 50° C. in a vacuum oven to afford 23 (1.35 g, 92%) as a light orange solid. The product was characterized by IR analysis, specifically by the appearance of the urea carbonyl peak (C=O, 1716.8 cm-1).

Example 24—Preparation of TyMA-PASU (24)

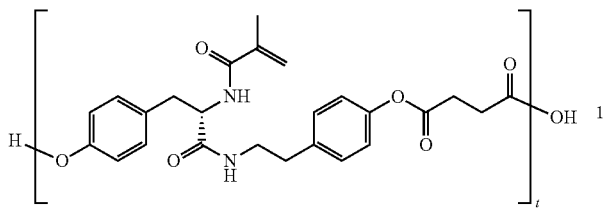

Compound 3 (5.00 g, 1 equivalent) was charged to a 250-mL flask with a magnetic stir bar. DMAP (0.415 g, 0.25 equivalents), 4-(dimethylamino) pyridinium 4-toluene sulfonate (0.400 g, 0.1 equivalent), succinic acid (1.37 g, 1 equivalent), and THF (45 mL) were sequentially added to the reaction flask, and the contents stirred at room temperature for 30 minutes. Diisopropylcarbodiimide (6.3 mL, 3 equivalents) was then added via syringe with stirring. The resulting solution was left to stir for 24 hours at room temperature, with visible precipitate forming after several hours. Upon completion, the reaction was concentrated via rotary evaporation and triturated in iPrOH (125 mL) for 2 hours. The precipitate was vacuum filtered and washed with iPrOH (4 portions, 50 mL each). The solids were then dried for 16 hours at 50° C. in a vacuum oven to afford 24 (5.78 g, 91%) as a tan solid. The product was characterized by IR analysis, specifically by the appearance of the phenolic ester carbonyl peak (C=O, 1748.1 cm-1).

Example 25—Preparation of TyMA-PASE (25)

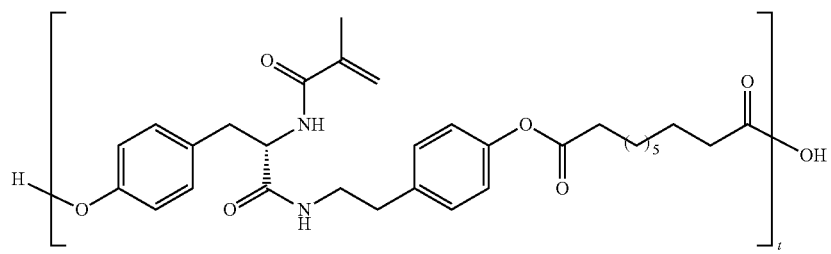

Compound 3 (1.00 g, 1 equivalent) was charged to a 50-mL flask with a magnetic stir bar. DMAP (0.083 g, 0.25 equivalents), 4-(dimethylamino) pyridinium 4-toluene sulfonate (0.080 g, 0.1 equivalent), sebacic acid (0.549 g, 1 equivalent), and THF (20 mL) were sequentially added to the reaction flask, and the contents stirred at room temperature for 30 minutes. Diisopropylcarbodiimide (1.26 mL, 3 equivalents) was then added via syringe with stirring. The resulting solution was left to stir for 24 hours at room temperature, with visible precipitate forming after several hours. Upon completion, the reaction was concentrated via rotary evaporation and triturated in MeOH (50 mL) for 2 hours. The precipitate was vacuum filtered and washed with MeOH (4 portions, 50 mL each). The solids were then dried for 16 hours at 50° C. in a vacuum oven to afford 25 (0.651 g, 43%) as a beige solid. The product was characterized by IR analysis, specifically by the appearance of the phenolic ester carbonyl peak (C=O, 1750.7 cm-1).

Example 26—Preparation of TyMA-PACI (26)

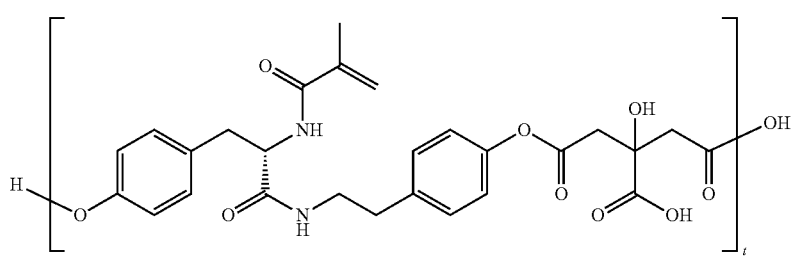

Compound 3 (5.00 g, 1 equivalent) was charged to a 250-mL flask with a magnetic stir bar. DMAP (0.415 g, 0.25 equivalents), 4-(dimethylamino) pyridinium 4-toluene sulfonate (0.400 g, 0.1 equivalent), citric acid (2.61 g, 1 equivalent), THF (55 mL), and DMF (10 mL) were sequentially added to the reaction flask, and the contents stirred at room temperature for 30 minutes. Diisopropylcarbodiimide (6.3 mL, 3 equivalents) was then added via syringe with stirring. The resulting solution was left to stir for 24 hours at room temperature, with visible dark precipitate forming after several hours. Upon completion, the reaction was concentrated via rotary evaporation and triturated in iPrOH (150 mL) for 2 hours. The precipitate was vacuum filtered and washed with iPrOH (4 portions, 50 mL each). The solids were triturated again in iPrOH (150 mL), vacuum filtered, and washed with iPrOH (50 mL portions). The solids were dried for 16 hours at 50° C. in a vacuum oven to afford 26 (3.01 g, 41%) as a black solid. The product was characterized by IR analysis, specifically by the appearance of the phenolic ester carbonyl peak (C=O, 1749.0 cm-1).

Example 27—Preparation of TyMA-PA/HEMA/PCL-DMA Copolymer (27)

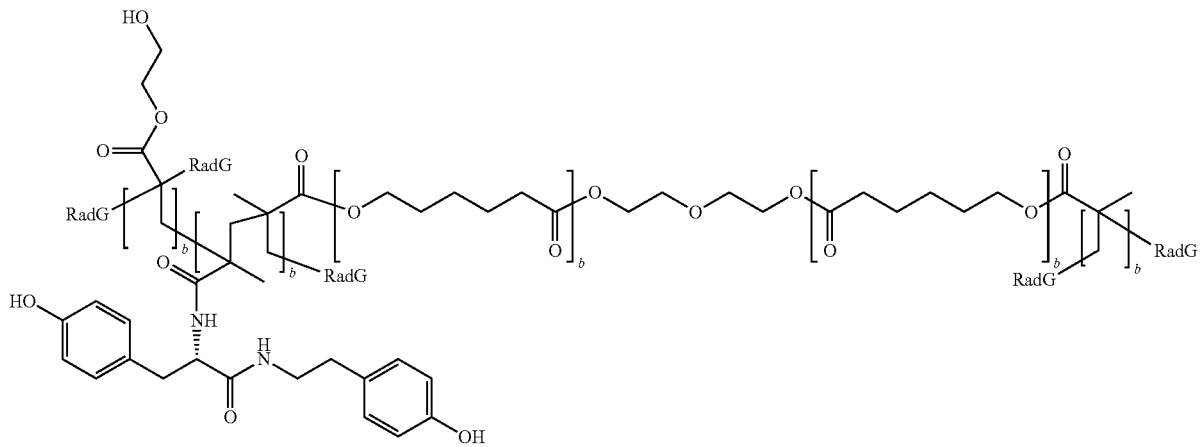

RadG can be alkene-linked monomers, oligomers, or polymers of any of the following, and/or terminal groups:

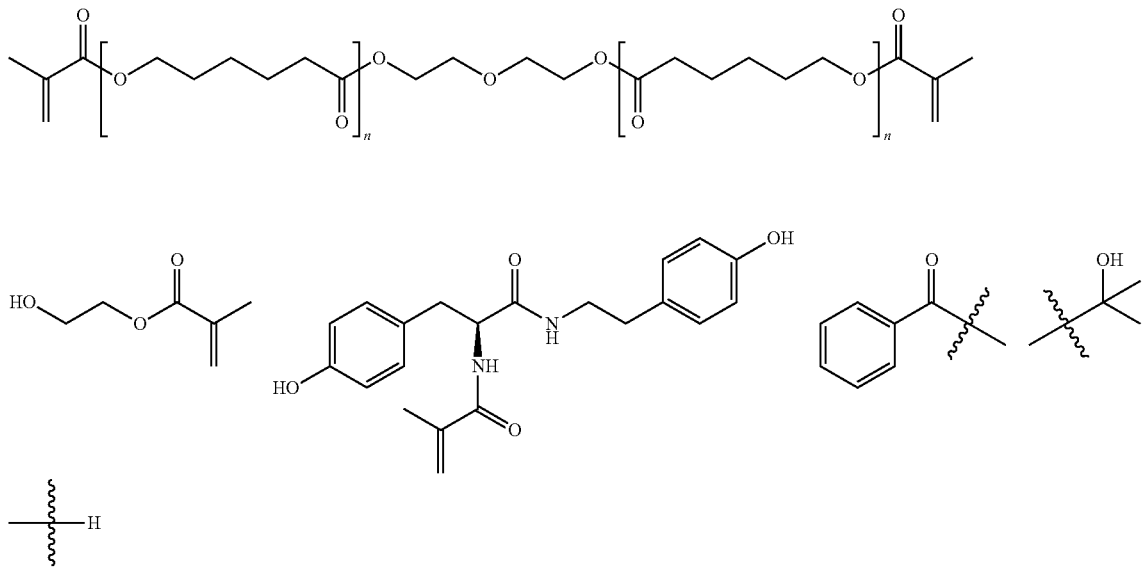

Compound 6 (14.8 wt %) was dissolved in HEMA (47.4 wt %) and poly(caprolactone diol dimethacrylate) (aka PCL-DMA, average MW=686, 35.5 wt %) with heating (50° C.) and magnetic stirring for 30 minutes. The now homogeneous resin was cooled to room temperature, and Irgacure 2022 (2.3 wt %) was added with stirring. The resin was poured between glass plates with a Teflon spacer (1.6 mm thickness) and cured with 405 nm UV laser light for 2 minutes. The thickened material was postcured in a UV oven equipped with 365 nm light bulbs for 16 hours to afford 27.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the disclosure herein has been described with reference to particular embodiments, it is to be understood that these embodiments are merely illustrative of the principles and applications of the present disclosure. It is therefore understood that numerous modifications may be made to the illustrative embodiments and that other arrangements may be devised without departing from the spirit and scope of the present disclosure as defined by the appended claims.

Additional Embodiments

The thermosetting resin compositions of the subject invention can be utilized with Stereolithographic apparatus' ("SLA"; See U.S. Pat. No. 5,236,637), Selective laser Sintering (SLS), Multijet and Continuous liquid Interface Production ("CLIP-US"; See U.S. Patent No. 2015/0097315) and combinations of processes thereof to make 3-D structures and parts.

Additional non-limiting embodiments are set forth below.

Additional Embodiment 1

An electromagnetic-radiation curable, biodegradable resin suitable for three-dimensional printing.

Additional Embodiment 2

The resin composition of additional embodiment 1, wherein the resin has a viscosity suitable for three-dimensional printers, ranging from 0.1 to 500,000 centipoise, preferably between 1 to 100,000 centipoise, and most preferably between 10 to 10,000 centipoise.

Additional Embodiment 3

The resin composition of additional embodiment 1, comprising an electromagnetically active structure of the form Formula (IA)

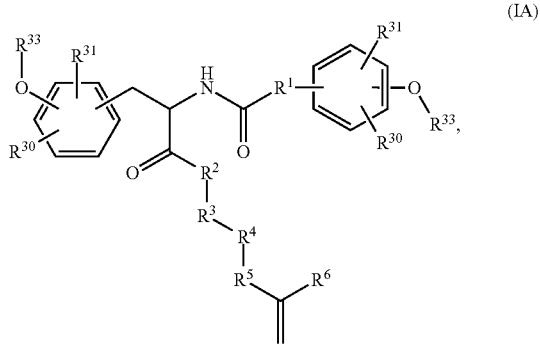

wherein
$R^1$ is a saturated or unsaturated, straight chain or branched alkyl group having between 0 and 12 carbon atoms;
$R^2$ is —O—, —$NR^s$— where $R^s$ is H or a $C_1$-$C_4$ alkyl group, or —S—;
$R^3$ is a straight chain or branched alkyl group having up to 10 carbon atoms, a straight chain or branched alkylaryl group having up to 20 carbon atoms, or a siloxane group;
$R^4$ is —O—, —$NR^s$— where $R^s$ is H or a $C_1$-$C_4$ alkyl group, —S—, —$CH_2$—;
$R^5$ is —C(O)—, —$CH_2$—, —C(H)(Ph)- where Ph may include one or more substituents selected from —OH, a halogen, $C_1$-$C_4$ alkyl, or —$NR^s$— where $R^s$ is H or a $C_1$-$C_4$ alkyl group;
$R^6$ is H or a straight chain or branched alkyl group having up to 18 carbons atoms;
each of $R^{30}$ and $R^{31}$ are independently selected from I or H; and
each $R^{33}$ is independently H, —CN, 4-hydroxybenzene, 3-iodo-4-hydroxybenzene, or 3,5-diiodo-4-hydroxybenzene.

Additional Embodiment 4

The compound of additional embodiment 3, wherein $R^1$ is —$CH_2CH_2CH_2$—.

Additional Embodiment 5

The compound of additional embodiment 3, wherein $R^1$ is —$CH_2CH_2$—.

Additional Embodiment 6

The compound of additional embodiment 3, wherein $R^1$ is —$CH_2$—.

Additional Embodiment 7

The compound of additional embodiment 3, wherein at least two of $R^2$, $R^4$, and $R^5$ are O.

Additional Embodiment 8

The compound of additional embodiment 3, wherein at least one of $R^2$ or $R^4$ is —O—; $R^3$ is a straight chain or branched $C_1$-$C_6$ alkyl group; and $R^1$ is a $C_1$-$C_6$ alkyl group.

Additional Embodiment 9

The compound of additional embodiment 3, wherein both of $R^2$ and $R^4$ are —O—; $R^3$ is a straight chain or branched $C_1$-$C_6$ alkyl group; and $R^1$ is a $C_1$-$C_6$ alkyl group.

Additional Embodiment 10

The compound of additional embodiment 3, wherein both of $R^2$ and $R^4$ are —O—; $R^3$ is a straight chain or branched $C_1$-$C_6$ alkyl group; $R^1$ is a $C_1$-$C_6$ alkyl group; and $R^5$ is C=O.

Additional Embodiment 11

The compound of additional embodiment 3, wherein both of $R^2$ and $R^4$ are —O—; $R^3$ is a straight chain or branched $C_1$-$C_6$ alkyl group; $R^1$ is a $C_1$-$C_6$ alkyl group; and $R^5$ is —$CH_2$—.

Additional Embodiment 12

The compound of additional embodiment 3, wherein $R^5$ is C=O or —$CH_2$—.

Additional Embodiment 13

The compound of additional embodiment 3, wherein the compound is selected from the group consisting of:

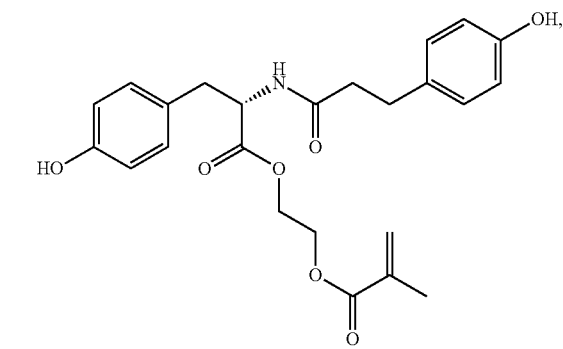

-continued

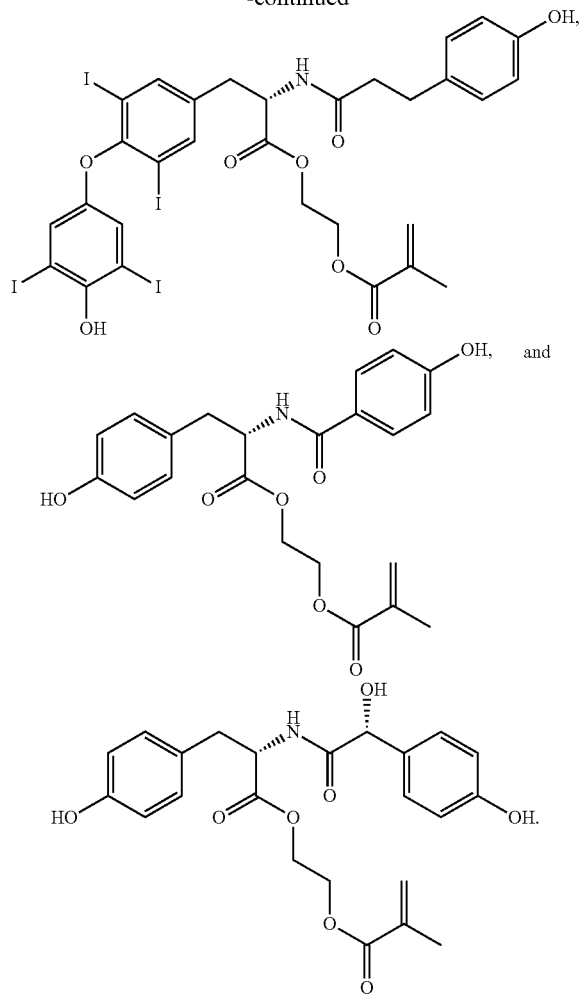

Additional Embodiment 14

A compound having the structure of Formula (IIA):

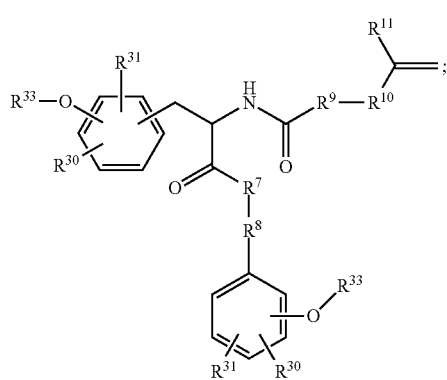

wherein
$R^7$ is —O—, —NR$^s$— where $R^s$ is H or a $C_1$-$C_4$ alkyl group, —S—, —CH$_2$—;
$R^8$ is a saturated or unsaturated, substituted or unsubstituted, straight chain or branched alkyl group having between 1 and 20 carbon atoms;
$R^9$ is a bond, —O—, —(CH$_2$)$_m$—;
$R^{10}$ is a bond; a straight chain or branched alkyl group having up to 10 carbon atoms; a straight chain or branched alkylaryl group having up to 20 carbon atoms; —(CR$^a$R$^b$—CR$^a$R$^b$O)$_o$—, —(CR$^a$R$^b$—CR$^a$R$^b$—O)$_o$—C(O)— wherein R$^a$ and R$^b$ are independently H or a $C_1$-$C_4$ alkyl group; or a siloxane group;
$R^{11}$ is H or a straight chain or branched alkyl group having up to 18 carbons;
each of $R^{30}$ and $R^{31}$ are independently selected from I or H;
each $R^{33}$ is independently H, —CN, 4-hydroxybenzene, 3-iodo-4-hydroxybenzene, or 3,5-diiodo-4-hydroxybenzene;
m is 0 or an integer ranging from 1 to 8;
each o is an integer ranging from 1 to 500.

Additional Embodiment 15

The compound of additional embodiment 14, wherein $R^7$ is —NH—, and $R^8$ is —(CH$_2$)$_n$—.

Additional Embodiment 16

The compound of additional embodiment 14, wherein $R^7$ is —NH—, and $R^8$ is —(CH$_2$)$_n$—, where n is an integer ranging from 1 to 4.

Additional Embodiment 17

The compound of additional embodiment 14, wherein $R^7$ is —NH—, and $R^8$ is —(CH$_2$)$_n$—, where n is an integer ranging from 1 to 2.

Additional Embodiment 18

The compound of additional embodiment 14, wherein $R^{11}$ is a $C_1$-$C_6$ alkyl group.

Additional Embodiment 19

The compound of additional embodiment 14, wherein $R^{11}$ is a $C_1$-$C_4$ alkyl group.

Additional Embodiment 20

The compound of additional embodiment 14, wherein $R^{11}$ is a $C_1$-$C_2$ alkyl group.

Additional Embodiment 21

The compound of additional embodiment 14, wherein both $R^9$ and $R^{10}$ are bonds.

Additional Embodiment 22

The compound of additional embodiment 14, wherein the compound is selected from the group consisting of:

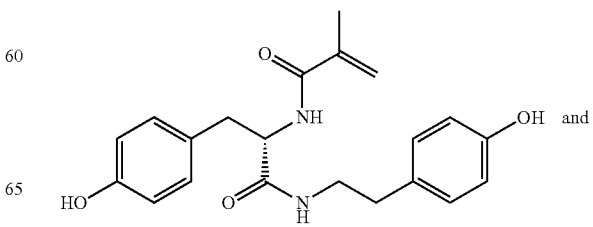

-continued

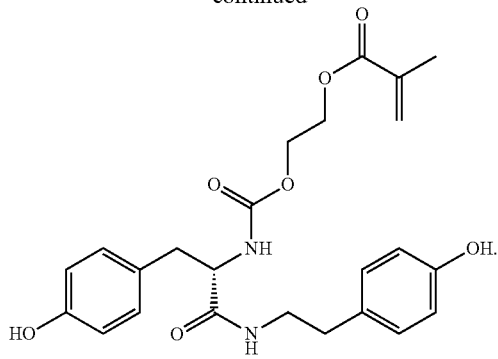

Additional Embodiment 23

The resin composition of additional embodiment 1, comprising a component of the form Formula (IIIA)

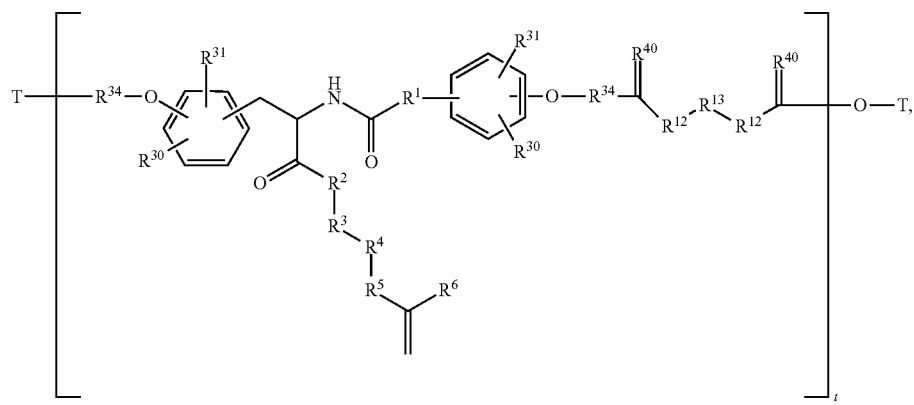

wherein
$R^1$ is —CH=CH— or (—CH$_2$-)$_n$;
$R^2$ is —O—, —NR$^s$—, where R$^s$ is H or a C$_1$-C$_4$ alkyl group, or —S—;
$R^3$ is a straight chain or branched alkyl group having up to 10 carbon atoms, a straight chain or branched alkylaryl group having up to 20 carbon atoms, or siloxane group;
$R^4$ is —O—, —NR$^s$—, where R$^s$ is H or a C$_1$-C$_4$ alkyl group, —S—, —CH$_2$—;
$R^5$ is C=O, —CH$_2$—, a benzyl group, or a substituted benzyl group;
$R^6$ is H or a straight chain or branched alkyl group having up to 18 carbons atoms;
each $R^{12}$ is independently a bond, —CH$_2$—, —O—, or —NR$^s$—, where R$^s$ is H or a C$_1$-C$_4$ alkyl group;
$R^{13}$ is a substituted or unsubstituted aliphatic group having between 1 and 5000 carbon atoms and optionally including one or more heteroatoms selected from O, N, or S; —(CH$_2$—O—(CH$_2$—O)$_v$—CH$_2$)—; or a substituted or unsubstituted aromatic group having between 6 and 280 carbon atoms;
each of $R^{30}$ and $R^{31}$ is independently selected from I or H;
each $R^{34}$ is independently a bond, 4-hydroxybenzene, 3-iodo-4-hydroxybenzene, or 3,5-diiodo-4-hydroxybenzene;
each $R^{40}$ is independently O or NH;

T is H;
n is 0 or an integer ranging from 1 to 8;
t is an integer ranging from 1 to 1000; and
v is 0 or an integer ranging from 1 to 5000.

Additional Embodiment 24

The compound of additional embodiment 23, wherein $R^1$ is —CH=CH— or (—CH$_2$-)$_n$, wherein n ranges from 1 to 8. In some embodiments, n ranges from to 1 to 4. In other embodiments, $R^1$ is —CH$_2$CH$_2$CH$_2$CH$_2$—. In other embodiments, $R^1$ is —CH$_2$CH$_2$CH$_2$—. In yet other embodiments, $R^1$ is —CH$_2$CH$_2$—. In further embodiments, $R^1$ is —CH$_2$—.

Additional Embodiment 25

The compound of additional embodiment 23, wherein $R^3$ is a C$_1$-C$_8$ straight chain or branched alkyl group. In other embodiments, $R^3$ is a C$_1$-C$_6$ straight chain or branched alkyl group. In yet other embodiments, $R^3$ is a C$_1$-C$_4$ straight chain or branched alkyl group. Additional Embodiment 26. The compound of additional embodiment 23, wherein $R^3$ has the structure -Alkyl-Phenyl-Alkyl- or -Phenyl-Alkyl-Phenyl-, wherein each alkyl group may be straight chain or branched, and wherein $R^3$ has up to 16 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 12 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 9 carbon atoms.

Additional Embodiment 27

The compound of additional embodiment 23, wherein the siloxane group has the structure of —(R′″)(R″)—Si—O—Si—(R″)(R′″)—, or —(R′″)(R″)—Si—[O—Si—(R″)(R′″)]$_h$ O—Si—(R″)(R′″)—, wherein R′″ and R″ are independently selected from C$_1$-C$_4$ alkyl, C$_6$ aryl, or H and wherein h ranges from 1 to 2000. In some embodiments, h ranges from 1 to 1500. In other embodiments, h ranges from 1 to 1000. In yet other embodiments, h ranges from 1 to 750. In further embodiments, h ranges from 1 to 500. In yet further embodiments, h ranges from 1 to 250.

Additional Embodiment 28

The compound of additional embodiment 23, wherein $R^3$ is 2,2,-dimethyl propane or sec-butane. In other embodiments, $R^3$ is derived from 2,2-diphenyl propane. In some embodiments, $R^3$ is derived from poly(dimethylsiloxane) having a molecular weight ranging from about 70 to about 100,000; or derived from poly(diarylsiloxane) having a molecular weight ranging from about 190 to about 100,000.

Additional Embodiment 29

The compound of additional embodiment 23, wherein $R^5$ is —C(O)—, —CH$_2$— or —C(H)(Ph)-. In some embodiments, $R^5$ is —CH$_2$—. In some embodiments, $R^5$ is —C(O)—.

Additional Embodiment 30

The compound of additional embodiment 23, wherein, $R^6$ is H. In other embodiments, $R^6$ is a $C_1$-$C_8$ straight chain or branched alkyl group. In other embodiments, $R^6$ is a $C_1$-$C_6$ straight chain or branched alkyl group. In yet other embodiments, $R^6$ is a $C_1$-$C_4$ straight chain or branched alkyl group. In further embodiments, $R^6$ is methyl.

Additional Embodiment 31

The compound of additional embodiment 23, wherein $R^{13}$ is —(CH$_2$)$_u$—, where u is 0 or an integer ranging from 1 to 5000; or a group —(C$_6$H$_4$—O—(C$_6$H$_4$—O)$_w$—C$_6$H$_4$—, where w is 0 or an integer ranging from 1 to 40.

Additional Embodiment 32

The resin composition of additional embodiment 1, comprising a component of the form Formula (IVA)

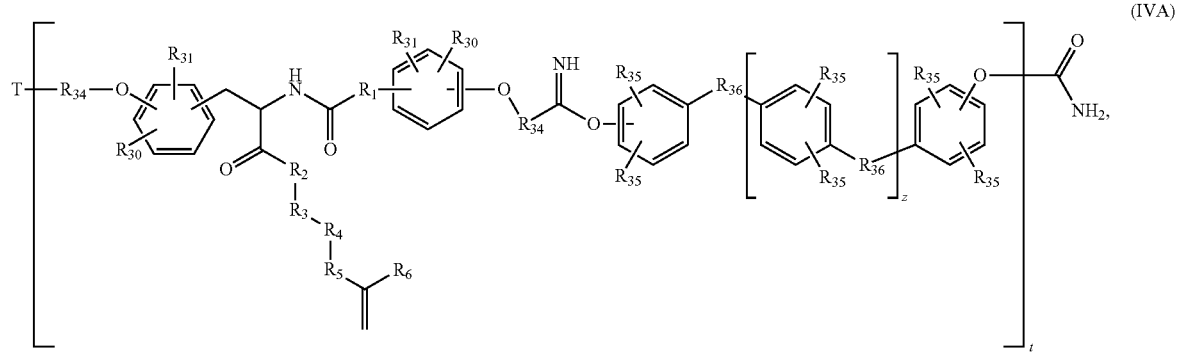

wherein
$R^1$ is —CH═CH— or (—CH$_2$-)$_n$;
$R^2$ is —O—, —NR$^s$—, where R$^s$ is H or a $C_1$-$C_4$ alkyl group, or —S—;
$R^3$ is a straight chain or branched alkyl group having up to 10 carbon atoms, a straight chain or branched alkylaryl group having up to 20 carbon atoms, or siloxane group;
$R^4$ is —O—, —NR$^s$—, where R$^s$ is H or a $C_1$-$C_4$ alkyl group, —S—, —CH$_2$—;
$R^5$ is C═O, —CH$_2$—, a benzyl group, or a substituted benzyl group;

$R^6$ is H or a straight chain or branched alkyl group having up to 18 carbons atoms; each of $R^{30}$ and $R^{31}$ is independently selected from I or H;
each $R^{34}$ is independently a bond, 4-hydroxybenzene, 3-iodo-4-hydroxybenzene, or 3,5-diiodo-4-hydroxybenzene;
each $R^{35}$ is independently an H, an aliphatic group having between 1 and 9 carbon atoms, an aromatic group having between 6 and 10 carbon atoms, an —OH group, or halogen;
each $R^{36}$ is $R^{14}$, a substituted or unsubstituted aromatic group having between 6 and 10 carbon atoms, CH$_2$, CH(CH$_3$), C(CH$_3$)$_2$, SO$_2$, O, or S;
and where $R^{14}$ is —CH(CH$_3$)—, —CH$_2$—, —C(CH$_3$)$_2$—, dicyclopentadiene or a functionalized dicyclopentadiene;
T is H;
t is an integer ranging from 1 to 1000;
n is 0 or an integer ranging from 1 to 8; and
z is 0 or an integer ranging from 1 to 100.

Additional Embodiment 33

The compound of additional embodiment 32, wherein $R^1$ is —CH═CH— or (—CH$_2$-)$_n$, wherein n ranges from 1 to 8. In some embodiments, n ranges from to 1 to 4. In other embodiments, $R^1$ is —CH$_2$CH$_2$CH$_2$CH$_2$—. In other embodiments, $R^1$ is —CH$_2$CH$_2$CH$_2$—. In yet other embodiments, $R^1$ is —CH$_2$CH$_2$—. In further embodiments, $R^1$ is —CH$_2$—.

Additional Embodiment 34

The compound of additional embodiment 32, wherein $R^3$ is a $C_1$-$C_8$ straight chain or branched alkyl group. In other embodiments, $R^3$ is a $C_1$-$C_6$ straight chain or branched alkyl group. In yet other embodiments, $R^3$ is a $C_1$-$C_4$ straight chain or branched alkyl group.

Additional Embodiment 35

The compound of additional embodiment 32, wherein $R^3$ has the structure -Alkyl-Phenyl-Alkyl- or -Phenyl-Alkyl-Phenyl-, wherein each alkyl group may be straight chain or branched, and wherein $R^3$ has up to 16 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 12 carbon atoms. In some embodiments, $R^3$ has the structure -Alkyl-Phenyl-Alkyl- or -Phenyl-Alkyl-Phenyl-, wherein each alkyl group may be straight chain or branched, and wherein $R^3$ has up to 9 carbon atoms.

Additional Embodiment 36

The compound of additional embodiment 32, wherein the siloxane group has the structure of —$(R''')(R'')$—Si—O—Si—$(R'')(R''')$—, or —$(R''')(R'')$—Si—[O—Si—$(R'')(R''')$]$_h$—O— Si—$(R'')(R''')$—, wherein $R'''$ and $R''$ are independently selected from $C_1$-$C_4$ alkyl, $C_6$ aryl, or H and herein h ranges from 1 to 2000. In some embodiments, h ranges from 1 to 1500. In other embodiments, h ranges from 1 to 1000. In yet other embodiments, h ranges from 1 to 750. In further embodiments, h ranges from 1 to 500. In yet further embodiments, h ranges from 1 to 250.

Additional Embodiment 37

The compound of additional embodiment 32, wherein $R^3$ is 2,2,-dimethyl propane or sec-butane. In other embodiments, $R^3$ is derived from 2,2-diphenyl propane. In some embodiments, $R^3$ is derived from poly(dimethylsiloxane) having a molecular weight ranging from about 70 to about 100,000; or derived from poly(diarylsiloxane) having a molecular weight ranging from about 190 to about 100,000.

Additional Embodiment 38

The compound of additional embodiment 32, wherein $R^5$ is —C(O)—, —CH$_2$— or —C(H)(Ph)-. In some embodiments, $R^5$ is —CH$_2$—. In some embodiments, $R^5$ is —C(O)—.

Additional Embodiment 39

The compound of additional embodiment 32, wherein $R^6$ is H. In other embodiments, $R^6$ is a $C_1$-$C_8$ straight chain or branched alkyl group. In other embodiments, $R^6$ is a $C_1$-$C_6$ straight chain or branched alkyl group. In yet other embodiments, $R^6$ is a $C_1$-$C_4$ straight chain or branched alkyl group. In further embodiments, $R^6$ is methyl.

Additional Embodiment 40

The compound of additional embodiment 32, wherein $R^{13}$ is —(CH$_2$)$_u$—, where u is 0 or an integer ranging from 1 to 5000; or a group —(C$_6$H$_4$—O—(C$_6$H$_4$—O)$_w$—C$_6$H$_4$—, where w is 0 or an integer ranging from 1 to 40.

Additional Embodiment 41

The compound of additional embodiment 32, wherein $R^{35}$ is OH and $R^{36}$ is —CH$_2$—, —CH(CH$_3$)— or —C(CH$_3$)$_2$.

Additional Embodiment 42

The resin composition of additional embodiment 1, comprising a component of the form Formula (VA)

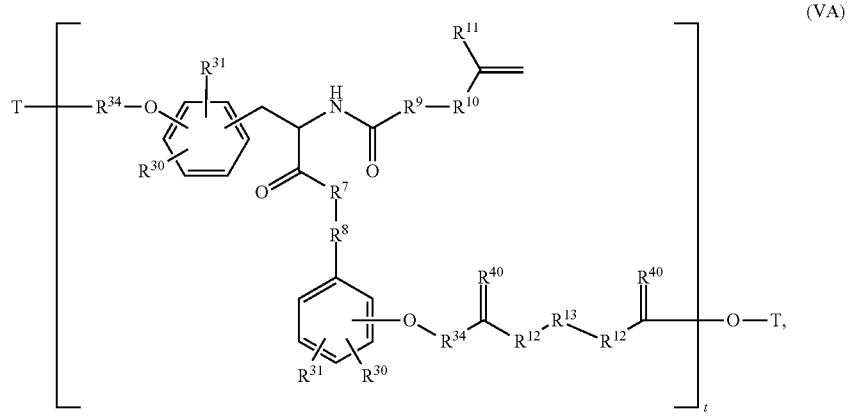

(VA)

wherein
$R^7$ is —O—, —NR$^s$—, where $R^s$ is H or a $C_1$-$C_4$ alkyl group, —S—, —CH$_2$—;
$R^8$ is a saturated or unsaturated, substituted or unsubstituted, straight chain or branched alkyl group having between 1 and 20 carbon atoms;
$R^9$ is a bond, —O—, —(CH$_2$)$_m$—;
$R^{10}$ is a bond; a straight chain or branched alkyl group having up to 10 carbon atoms; a straight chain or branched alkylaryl group having up to 20 carbon atoms; —(CR$^a$R$^b$—CR$^a$R$^b$O)$_o$—, —(CR$^a$R$^b$—CR$^a$R$^b$—O)$_o$—C(O)— wherein R$^a$ and R$^b$ are independently H or a $C_1$-$C_4$ alkyl group; or a siloxane group;
$R^{11}$ is H or a straight chain or branched alkyl group having up to 18 carbons;
each $R^{12}$ is independently a bond, —CH$_2$—, —O—, or —NR$^s$—, where R$^s$ is H or a $C_1$-$C_4$ alkyl group;
$R^{13}$ is a substituted or unsubstituted aliphatic group having between 1 and 5000 carbon atoms and optionally including one or more heteroatoms selected from O, N, or S; —(CH$_2$—O—(CH$_2$—O)$_V$—CH$_2$)—; or a substituted or unsubstituted aromatic group having between 6 and 280 carbon atoms;
each of $R^{30}$ and $R^{31}$ is independently selected from I or H;
each $R^{34}$ is independently a bond, 4-hydroxybenzene, 3-iodo-4-hydroxybenzene, or 3,5-diiodo-4-hydroxybenzene;

each $R^{40}$ is independently O or NH;
T is H;
m is 0 or an integer ranging from 1 to 8;
o is an integer ranging from 1 to 500; and
t is an integer ranging from 1 to 1000.

Additional Embodiment 43

The compound of additional embodiment 42, wherein o is an integer ranging from 1 to 400. In other embodiments, o is an integer ranging from 1 to 300. In yet other embodiments, o is an integer ranging from 1 to 200. In further embodiments, o is an integer ranging from 1 to 100. In yet further embodiments, o is an integer ranging from 1 to 50.

Additional Embodiment 44

The compound of additional embodiment 42, wherein, $R^8$ is —CH=CH— or $(—CH_2-)_n$, wherein n ranges from 1 to 20.

Additional Embodiment 45

The compound of additional embodiment 42, wherein n ranges from to 1 to 16.

Additional Embodiment 46

The compound of additional embodiment 42, wherein n ranges from to 1 to 16. In yet other embodiments, n ranges from to 1 to 12.

Additional Embodiment 47

The compound of additional embodiment 42, wherein n ranges from to 1 to 8.

Additional Embodiment 48

The compound of additional embodiment 42, wherein n ranges from to 1 to 6.

Additional Embodiment 49

The compound of additional embodiment 42, wherein $R^8$ is —$CH_2CH_2CH_2CH_2$—.

Additional Embodiment 50

The compound of additional embodiment 42, wherein $R^8$ is $CH_2CH_2CH_2$—.

Additional Embodiment 51

The compound of additional embodiment 42, wherein $R^8$ is —$CH_2$—.

Additional Embodiment 52

The compound of additional embodiment 42, wherein $R^{10}$ is —$(CH_2)—_p$, where p ranges from 1 to 12. In some embodiments, p ranges from 1 to 6. In other embodiments, p ranges from 1 to 4. In yet other embodiments, p is 1 or 2.

Additional Embodiment 53

The compound of additional embodiment 42, wherein $R^{10}$ is —$(CH_2CH_2O)_o$—, —$(CH_2CH_2O)_oC(O)$—, where o ranges from 1 to 250.

Additional Embodiment 54

The compound of additional embodiment 42, wherein $R^{10}$ is —$(CH_2CH_2O)_o$—, —$(CH_2CH_2O)_oC(O)$—, where o ranges from 1 to 100.

Additional Embodiment 55

The compound of additional embodiment 42, wherein $R^{10}$ is —$(CH_2CH_2O)_o$—, —$(CH_2CH_2O)_oC(O)$—, where o ranges from 1 to 50.

Additional Embodiment 56

The compound of additional embodiment 42, wherein $R^{10}$ is —$(CH_2CH_2O)_o$—, —$(CH_2CH_2O)_oC(O)$—, where o ranges from 1 to 10.

Additional Embodiment 57

The compound of additional embodiment 42, wherein $R^{10}$ is —$(CH_2CH_2O)_o$—, —$(CH_2CH_2O)_oC(O)$—, where o ranges from 1 to 6.

Additional Embodiment 58

The compound of additional embodiment 42, wherein $R^{11}$ is H. In other embodiments, $R^{11}$ is methyl.

Additional Embodiment 59

The resin composition of additional embodiment 1, comprising a component of the form Formula (VIA)

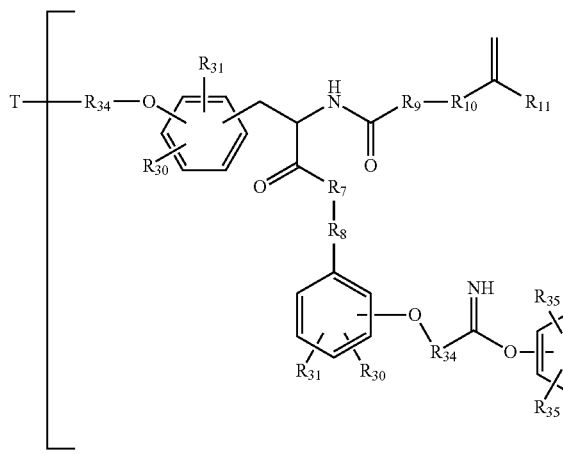
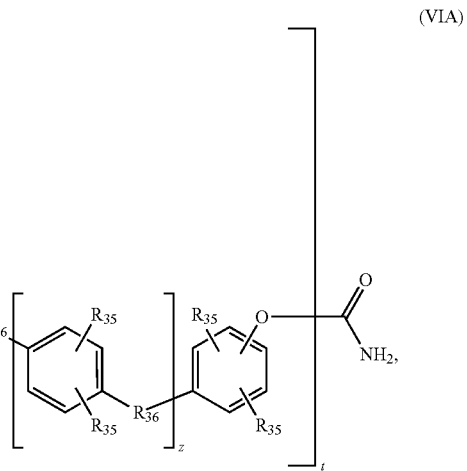

(VIA)

wherein
$R^7$ is —O—, —NR$^s$—, where $R^s$ is H or a $C_1$-$C_4$ alkyl group, —S—, —CH$_2$—;
$R^8$ is a saturated or unsaturated, substituted or unsubstituted, straight chain or branched alkyl group having between 1 and 20 carbon atoms;
$R^9$ is a bond, —O—, —(CH$_2$)$_m$—;
$R^{10}$ is a bond; a straight chain or branched alkyl group having up to 10 carbon atoms; a straight chain or branched alkylaryl group having up to 20 carbon atoms; —(CR$^a$R$^b$—CR$^a$R$^b$O)$_o$—, —(CR$^a$R$^b$—CR$^a$R$^b$—O)$_o$—C(O)— wherein R$^a$ and R$^b$ are independently H or a $C_1$-$C_4$ alkyl group; or a siloxane group;
$R^{11}$ is H or a straight chain or branched alkyl group having up to 18 carbons;
each of $R^{30}$ and $R^{31}$ is independently selected from I or H;
each $R^{34}$ is independently a bond, 4-hydroxybenzene, 3-iodo-4-hydroxybenzene, or 3,5-diiodo-4-hydroxybenzene;
each $R^{35}$ is independently an H, an aliphatic group having between 1 and 9 carbon atoms, an aromatic group having between 6 and 10 carbon atoms, an —OH group, or halogen;
each $R^{36}$ is $R^{14}$, a substituted or unsubstituted aromatic group having between 6 and 10 carbon atoms, —CH$_2$—, —CH(CH$_3$)—, —C(CH$_3$)$_2$—, SO$_2$, O, or S;
$R^{14}$ is —CH(CH$_3$)—, —CH$_2$—, —C(CH$_3$)$_2$—, dicyclopentadiene or a functionalized dicyclopentadiene;
T is H;
m is 0 or an integer ranging from 1 to 8;
o is an integer ranging from 1 to 500;
t is an integer ranging from 1 to 1000; and
z is 0 or an integer ranging from 1 to 100.

Additional Embodiment 60

The compound of additional embodiment 59, wherein o is an integer ranging from 1 to 400. In other embodiments, o is an integer ranging from 1 to 300. In yet other embodiments, o is an integer ranging from 1 to 200. In further embodiments, o is an integer ranging from 1 to 100. In yet further embodiments, o is an integer ranging from 1 to 50.

Additional Embodiment 61

The compound of additional embodiment 59, wherein $R^8$ is —CH═CH— or (—CH$_2$-)$_n$, wherein n ranges from 1 to 20. In some embodiments, n ranges from to 1 to 16. In other embodiments, n ranges from to 1 to 16. In yet other embodiments, n ranges from to 1 to 12. In further embodiments, n ranges from to 1 to 8. In even further embodiments, n ranges from to 1 to 6. In some embodiments, $R^8$ is —CH$_2$CH$_2$CH$_2$CH$_2$—. In other embodiments, $R^8$ is —CH$_2$CH$_2$CH$_2$—. In yet other embodiments, $R^8$ is —CH$_2$CH$_2$—. In further embodiments, $R^8$ is —CH$_2$—.

Additional Embodiment 62

The compound of additional embodiment 59, wherein $R^{10}$ is —(CH$_2$)—$_p$, where p ranges from 1 to 12. In some embodiments, p ranges from 1 to 6. In other embodiments, p ranges from 1 to 4. In yet other embodiments, p is 1 or 2.

Additional Embodiment 63

The compound of additional embodiment 59, wherein $R^{10}$ is —(CH$_2$CH$_2$O)$_o$—, —(CH$_2$CH$_2$O)$_o$C(O)—, where o ranges from 1 to 250.

Additional Embodiment 64

The compound of additional embodiment 59, wherein $R^{10}$ is —(CH$_2$CH$_2$O)$_o$—, —(CH$_2$CH$_2$O)$_o$C(O)—, where o ranges from 1 to 100.

Additional Embodiment 65

The compound of additional embodiment 59, wherein $R^{10}$ is —(CH$_2$CH$_2$O)$_o$—, —(CH$_2$CH$_2$O)$_o$C(O)—, where o ranges from 1 to 50.

Additional Embodiment 66

The compound of additional embodiment 59, wherein $R^{10}$ is —(CH$_2$CH$_2$O)$_o$—, —(CH$_2$CH$_2$O)$_o$C(O)—, where o ranges from 1 to 10.

Additional Embodiment 67

The compound of additional embodiment 59, wherein $R^{10}$ is —(CH$_2$CH$_2$O)$_o$—, —(CH$_2$CH$_2$O)$_o$C(O)—, where o ranges from 1 to 6.

Additional Embodiment 68

The compound of additional embodiment 59, wherein $R^{11}$ is H. In other embodiments, $R^{11}$ is methyl.

Additional Embodiment 69

The compound of additional embodiment 59, wherein $R^{35}$ is OH and $R^{36}$ is —$CH_2$—, —$CH(CH_3)$— or —$C(CH_3)_2$.

Additional Embodiment 70

The resin composition of additional embodiment 1, upon exposure to UV light, the compounds of additional embodiments 3, 14, 23, 32, 42, and 59 are converted into the highly cross-linked solid materials.

Additional Embodiment 71

The resin composition of additional embodiment 1 is comprised of a compound or mixture of compounds from additional embodiments 3, 14, 23, 32, 42, and 59, a co-monomer or solvent, and a photo-initiator and/or thermal catalyst.

Additional Embodiment 72

Co-monomers and solvents of additional embodiment 71 are selected from N,N-dimethylformamide, dichloromethane, tetrahydrofuran, 2-hydroxyethyl methacrylate, 2-hydroxyethyl acrylate, tert-butylaminoethyl methacrylate, any acrylated or methacrylated derivatives of erythritol such as (2R,3S)-2,3-dihydroxybutane-1,4-diyl bis(2-methylacrylate), polycaprolactone diol (average Mn from 200 to 50,000), acrylate- or methacrylate-terminated polycaprolactones such as polycaprolactone bismethacrylate, acrylated or methacrylated diols such as 3-hydroxypropyl methacrylate and propylene bismethacrylate, triols, and polyols consisting of vinyl, acrylate, methacrylate, and acrylonitrile.

Additional Embodiment 73

Photo-initiators of additional embodiment 71 are selected from a group consisting of 2-dimethoxy-2-phenylacetophenone, benzoyl formates, acyl-phosphine oxides, acyl phosphinates, alpha-amino alkyl-phenones, alpha-hydroxy alkylphenones, alpha-dialkoxy acetophenones, benzophenones/amines, thioxanthines/amines, bis(4-tert-butylphenyl) iodonium perfluoro-1-butanesulfonate, diphenyliodonium nitrate, camphorquinone, fluoresceins such as Eosin Y and Rose Bengal, Riboflavin, H-Nu 470, and lumichrome.

Additional Embodiment 74

The resin composition of additional embodiment 1, wherein the electromagnetic cure comprises ultraviolet radiation (UV) or cationic cure, electron beam (EB), Infrared (IR), and/or visible light.

Additional Embodiment 75

The resin composition of additional embodiment 1, wherein a second stage cure is a thermal post cure to finish curing the resin and can utilize addition cure, condensation reaction, peroxide cure or chemical additives.

Additional Embodiment 76

The compounds from additional embodiments 3, 14, 23, 32, 42, and 59 may be mixed with a blocked isocyanate, a chain-extender, and a photo-initiator to generate an electromagnetic-curable resin composition.

Additional Embodiment 77

The resin composition in additional embodiment 76 can be b-staged with electromagnetic radiation.

Additional Embodiment 78

The resin composition in additional embodiment 76 can be thermally cured to generate a solid polyurethane material.

Additional Embodiment 79

The polymerized materials of additional embodiment 71 can be used as medical devices, anti-bacterial envelopes, antiseptic coatings for breast implants, surgical mesh, drug delivery systems, Capsugel pill or capsule coatings.

Additional Embodiment 80

The materials of additional embodiment 71 can be used to manufacture perforated meshes, that may or may not be biodegradable.

Additional Embodiment 81

The resin composition of additional embodiment 1 can be used in additive manufacturing devices including stereolithographic apparatus's (SLA), selective laser Sintering (SLS), digital light processing (DLP), Stratasys Polyjet printers, 3-D Systems printers, multi-jet and continuous liquid interface production (CLIP-US).

Additional Embodiment 82

The compounds from additional embodiments 3, 14, 23, 32, 42, and 59 can be used in solid form or filament form for additive manufacturing devices including fused deposition modeling (FDM).

The invention claimed is:

1. A compound having the structure defined by Formula (VA):

(VA)

[structure of Formula (VA) showing T—$R^{34}$—O— group with $R^{31}$, $R^{30}$ substituents on a ring, connected to a chain with $R^9$—$R^{10}$, $R^{11}$, N—H, $R^7$, $R^8$, and another ring with $R^{31}$, $R^{30}$, O—$R^{34}$, $R^{40}$, $R^{13}$, $R^{12}$, $R^{12}$, $R^{40}$, O—T, subscript $t$]

wherein
$R^7$ is —O—, —$NR^s$—, —S—, or —$CH_2$—, where $R^s$ is H or a $C_1$-$C_4$ alkyl;
$R^8$ is a saturated or unsaturated, substituted or unsubstituted, straight chain or branched alkyl group having between 1 and 20 carbon atoms;
$R^9$ is a bond, —O—, or —$(CH_2)_m$—

R¹⁰ is a bond; a straight chain or branched alkyl group having up to 10 carbon atoms; a straight chain or branched alkylaryl group having up to 20 carbon atoms; —(CRᵃRᵇ—CRᵃRᵇO)ₒ—, —(CRᵃRᵇ—CRᵃRᵇ—O)ₒ—C(O)— wherein Rᵃ and Rᵇ are independently H or a C₁-C₄ alkyl group; or a siloxane group;

R¹¹ is H or a straight chain or branched alkyl group having up to 18 carbons;

each R¹² is independently a bond, —CH₂—, —O—, or —NRˢ—, where Rˢ is H or a C₁-C₄ alkyl group;

R¹³ is a substituted or unsubstituted aliphatic group having between 1 and 5000 carbon atoms and optionally including one or more heteroatoms selected from O, N, or S; —(CH₂—O—(CH₂—O)ᵥ—CH₂)—; or a substituted or unsubstituted aromatic group having between 6 and 280 carbon atoms;

each of R³⁰ and R³¹ is independently selected from I or H;

each R³⁴ is independently a bond, 4-hydroxybenzene, 3-iodo-4-hydroxybenzene, or 3,5-diiodo-4-hydroxybenzene;

each R⁴⁰ is independently O or NH;

T is H; and m is 0 or an integer ranging from 1 to 8;

o is an integer ranging from 1 to 500;

v is 0 or an integer ranging from 1 to 5000; and t is an integer ranging from 1 to 1000.

2. The compound of claim 1, wherein each of R³⁰ and R³¹ are H.

3. The compound of claim 2, wherein R¹¹ is a C₁-C₄ alkyl group.

4. The compound of claim 2, wherein R¹⁰ is —(CH₂)ₚ—, where p is an integer ranging from 1 to 8.

5. The compound of claim 2, wherein R⁷ is —NH—, and R⁸ is —(CH₂)ₙ—, where n is an integer ranging from 1 to 4.

6. The compound of claim 1, wherein R⁸ is —CH=CH— or (—CH₂-)ₙ, wherein n ranges from 1 to 20.

7. The compound of claim 1, wherein R¹⁰ is —(CH₂)ₚ—, where p ranges from 1 to 12.

8. The compound of claim 1, wherein R¹⁰ is —(CH₂CH₂O)ₒ—, —(CH₂CH₂O)ₒC(O)—, where o ranges from 1 to 250.

9. The compound of claim 1, wherein the compound has the structure as defined by Formula (VB):

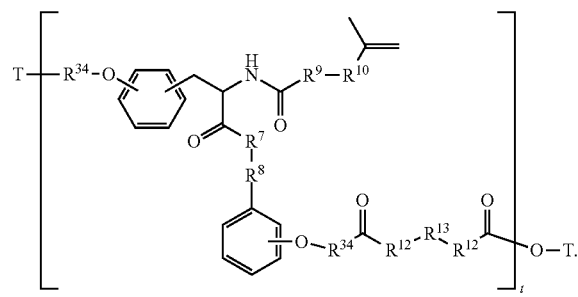

(VB)

10. The compound of claim 9, R⁷ is —NH—, R⁸ is —(CH₂)ₙ—, and at least one of R⁹ or R¹⁰ is a bond, where n is an integer ranging from 1 to 8.

11. The compound of claim 1, wherein the compound has the structure as defined by Formula (VC):

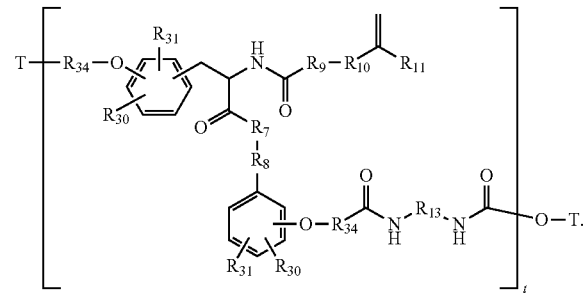

(VC)

12. The compound of claim 1, wherein the compound has the structure as defined by Formula (VD):

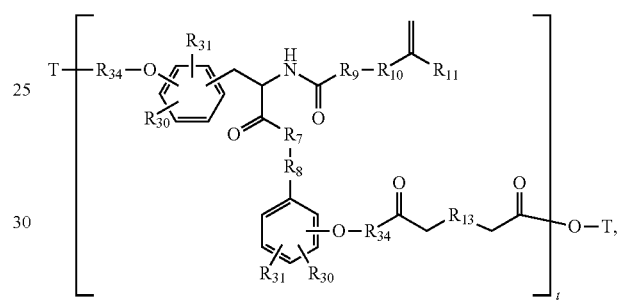

(VD)

wherein each of R³⁰ and R³¹ are H.

13. The compound of claim 1, wherein the compound has the structure as defined by Formula (VD):

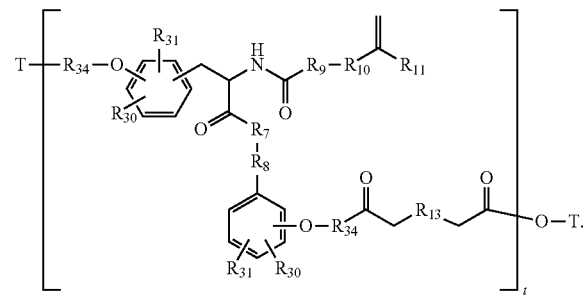

(VD)

14. The compound of claim 13, wherein R³⁴ is independently a bond.

15. The compound of claim 13, wherein R⁸ is —(CH₂)ₙ—, where n is an integer ranging from 1 to 8.

16. The compound of claim 15, wherein R⁷ is —NH—.

17. The compound of claim 15, wherein at least one of R⁹ or R¹⁰ is a bond.

18. The compound of claim 13, wherein both R⁹ and R¹⁰ are bonds.

19. The compound of claim 1, wherein the compound has the structure as defined by Formula (VE):

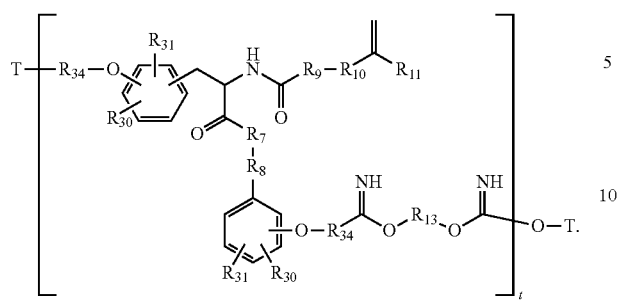
20. A compound is selected from the group consisting of:
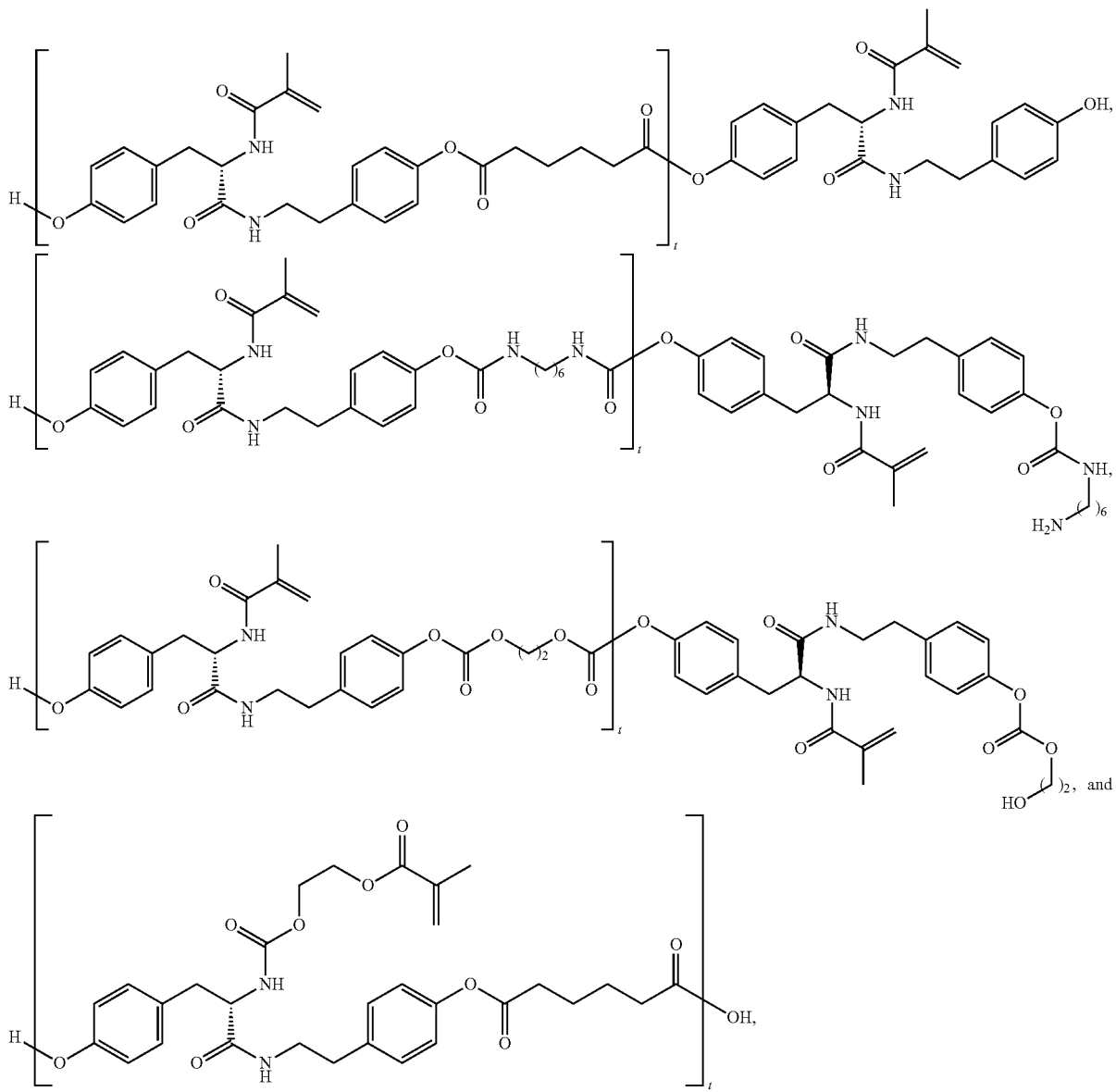
where t is an integer ranging from 1 to 1000.
* * * * *